United States Patent
Schenck et al.

(10) Patent No.: US 11,850,414 B2
(45) Date of Patent: Dec. 26, 2023

(54) FLUID HANDLING SYSTEM

(71) Applicant: TC1 LLC, St. Paul, MN (US)

(72) Inventors: Alan L. Schenck, Sunnyvale, CA (US); Paul F. Muller, San Carlos, CA (US); Keif M. Fitzgerald, San Jose, CA (US)

(73) Assignee: TC1 LLC, St. Paul, MN (US)

( * ) Notice: Subject to any disclaimer, the term of this patent is extended or adjusted under 35 U.S.C. 154(b) by 406 days.

(21) Appl. No.: 17/174,091

(22) Filed: Feb. 11, 2021

(65) Prior Publication Data
US 2021/0187270 A1    Jun. 24, 2021

Related U.S. Application Data

(60) Continuation of application No. 15/920,553, filed on Mar. 14, 2018, now Pat. No. 11,033,728, which is a
(Continued)

(51) Int. Cl.
*A61M 60/148* (2021.01)
*A61M 60/414* (2021.01)
(Continued)

(52) U.S. Cl.
CPC .......... *A61M 60/414* (2021.01); *A61M 1/155* (2022.05); *A61M 1/1524* (2022.05);
(Continued)

(58) Field of Classification Search
CPC .. A61M 60/122; A61M 60/13; A61M 60/216; A61M 1/101; A61M 1/122; A61M 1/125
See application file for complete search history.

(56) References Cited

U.S. PATENT DOCUMENTS

| 1,902,418 A | 3/1933 | Pilgrim |
| 2,356,659 A | 8/1944 | De Paiva |
| (Continued) | | |

FOREIGN PATENT DOCUMENTS

| CA | 2701810 A1 | 4/2009 |
| CA | 2701810 C | 4/2009 |
| (Continued) | | |

OTHER PUBLICATIONS

JP Notice of Allowance, dated Apr. 22, 2019 for related JP patent application No. 2016-500668.
(Continued)

*Primary Examiner* — Laura A Bouchelle
(74) *Attorney, Agent, or Firm* — Armstrong Teasdale LLP

(57) ABSTRACT

A fluid handling system includes a console configured to connect with a first electrical interface that is configured to connect to a plurality of components of the fluid handling system, the console including a second electrical interface configured to connect with the first electrical interface, a display, and one or more hardware processors. A control system includes the one or more hardware processors and a non-transitory memory storing instructions that, when executed, cause the control system to: detect an electrical signal from a first component of the plurality of components of the fluid handling system responsive to a caretaker performing a first instruction; determine a system state of the fluid handling system based at least in part on the electrical signal from the first component; compare the system state with a predetermined state condition corresponding to said first instruction; and output an indication on the display of the system state.

20 Claims, 46 Drawing Sheets

Related U.S. Application Data continuation of application No. PCT/US2016/051553, filed on Sep. 13, 2016, and a continuation-in-part of application No. 15/198,342, filed on Jun. 30, 2016, now Pat. No. 10,632,241, said application No. 15/198,342 is a division of application No. 14/203,978, filed on Mar. 11, 2014, now Pat. No. 9,381,288.

(60) Provisional application No. 62/220,040, filed on Sep. 17, 2015, provisional application No. 62/218,509, filed on Sep. 14, 2015, provisional application No. 62/218,508, filed on Sep. 14, 2015, provisional application No. 61/780,656, filed on Mar. 13, 2013.

(51) Int. Cl.

| | |
|---|---|
| *A61M 1/36* | (2006.01) |
| *A61M 5/172* | (2006.01) |
| *A61M 5/142* | (2006.01) |
| *A61M 1/00* | (2006.01) |
| *A61M 60/816* | (2021.01) |
| *A61M 60/808* | (2021.01) |
| *A61M 60/554* | (2021.01) |
| *A61M 60/523* | (2021.01) |
| *A61M 60/88* | (2021.01) |
| *A61M 60/878* | (2021.01) |
| *A61M 60/13* | (2021.01) |
| *A61M 60/237* | (2021.01) |
| *A61M 60/585* | (2021.01) |
| *A61M 60/538* | (2021.01) |
| *A61M 60/515* | (2021.01) |
| *A61M 1/14* | (2006.01) |

(52) U.S. Cl.
CPC ............ *A61M 1/3659* (2014.02); *A61M 1/77* (2021.05); *A61M 5/142* (2013.01); *A61M 5/172* (2013.01); *A61M 60/13* (2021.01); *A61M 60/148* (2021.01); *A61M 60/237* (2021.01); *A61M 60/515* (2021.01); *A61M 60/523* (2021.01); *A61M 60/538* (2021.01); *A61M 60/554* (2021.01); *A61M 60/585* (2021.01); *A61M 60/808* (2021.01); *A61M 60/816* (2021.01); *A61M 60/878* (2021.01); *A61M 60/88* (2021.01); *A61M 2205/04* (2013.01); *A61M 2205/12* (2013.01); *A61M 2205/3331* (2013.01); *A61M 2205/3368* (2013.01); *A61M 2205/502* (2013.01)

(56) References Cited

U.S. PATENT DOCUMENTS

| | | |
|---|---|---|
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,896,926 A | 7/1959 | Chapman |
| 2,935,068 A | 5/1960 | Shearman |
| 3,080,824 A | 3/1963 | Boyd |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,066,556 A | 1/1978 | Vaillancourt |
| 4,115,040 A | 9/1978 | Knorr |
| 4,129,129 A | 12/1978 | Amrine |
| 4,135,253 A | 1/1979 | Reich et al. |
| 4,143,425 A | 3/1979 | Runge |
| 4,149,535 A | 4/1979 | Volder |
| 4,304,524 A | 12/1981 | Coxon |
| D264,134 S | 4/1982 | Xanthopoulos |
| 4,382,199 A | 5/1983 | Isaacson |
| 4,392,836 A | 7/1983 | Sugawara |
| 4,458,366 A | 7/1984 | Macgregor et al. |
| 4,537,561 A | 8/1985 | Xanthopoulos |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett |
| 4,673,334 A | 6/1987 | Allington et al. |
| 4,686,982 A | 8/1987 | Nash |
| 4,696,667 A | 9/1987 | Masch |
| 4,704,121 A | 11/1987 | Moise |
| 4,728,319 A | 3/1988 | Masch |
| 4,753,221 A | 6/1988 | Kensey et al. |
| 4,769,006 A | 9/1988 | Papantonakos |
| 4,777,951 A | 10/1988 | Cribier et al. |
| 4,790,315 A | 12/1988 | Mueller, Jr. et al. |
| 4,817,586 A | 4/1989 | Wampler |
| 4,819,653 A | 4/1989 | Marks |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,341 A | 6/1990 | Euteneuer |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffmann et al. |
| 5,021,048 A | 6/1991 | Buckholtz |
| 5,044,902 A | 9/1991 | Malbec |
| 5,045,072 A | 9/1991 | Castillo et al. |
| 5,049,134 A | 9/1991 | Golding et al. |
| 5,059,174 A | 10/1991 | Vaillancourt |
| 5,061,256 A | 10/1991 | Wampler |
| 5,074,756 A | 12/1991 | Davis |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,292 A | 5/1992 | Hwang et al. |
| 5,112,349 A | 5/1992 | Summers et al. |
| 5,129,883 A | 7/1992 | Black |
| 5,142,155 A | 8/1992 | Mauze et al. |
| 5,147,186 A | 9/1992 | Buckholtz |
| 5,163,910 A | 11/1992 | Schwartz et al. |
| 5,171,212 A | 12/1992 | Buck et al. |
| 5,190,528 A | 3/1993 | Fonger et al. |
| 5,195,960 A | 3/1993 | Hossain et al. |
| 5,201,679 A | 4/1993 | Velte, Jr. et al. |
| 5,211,546 A | 5/1993 | Isaacson et al. |
| 5,221,270 A | 6/1993 | Parker |
| 5,234,407 A | 8/1993 | Teirstein et al. |
| 5,234,416 A | 8/1993 | Macaulay et al. |
| 5,282,787 A | 2/1994 | Wortrich |
| 5,290,227 A | 3/1994 | Pasque |
| 5,300,112 A | 4/1994 | Barr |
| 5,312,341 A | 5/1994 | Turi |
| 5,344,443 A | 9/1994 | Palma et al. |
| 5,346,458 A | 9/1994 | Affeld |
| 5,360,317 A | 11/1994 | Clausen et al. |
| 5,364,342 A | 11/1994 | Beuchat et al. |
| 5,376,114 A | 12/1994 | Jarvik |
| 5,393,197 A | 2/1995 | Lemont et al. |
| 5,393,207 A | 2/1995 | Maher et al. |
| 5,397,222 A | 3/1995 | Moss et al. |

(56) References Cited

U.S. PATENT DOCUMENTS

| | | |
|---|---|---|
| 5,405,341 A | 4/1995 | Martin |
| 5,405,383 A | 4/1995 | Barr |
| 5,437,541 A | 8/1995 | Vainrub |
| 5,449,342 A | 9/1995 | Hirose et al. |
| 5,458,459 A | 10/1995 | Hubbard et al. |
| 5,490,763 A | 2/1996 | Abrams et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,534,287 A | 7/1996 | Lukic |
| 5,586,868 A | 12/1996 | Lawless et al. |
| 5,588,812 A | 12/1996 | Taylor et al. |
| 5,601,420 A | 2/1997 | Warner et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,702,418 A | 12/1997 | Ravenscroft |
| 5,704,926 A | 1/1998 | Sutton |
| 5,707,218 A | 1/1998 | Maher et al. |
| 5,722,930 A | 3/1998 | Larson, Jr. et al. |
| 5,725,513 A | 3/1998 | Ju et al. |
| 5,725,570 A | 3/1998 | Heath |
| 5,730,628 A | 3/1998 | Hawkins |
| 5,735,897 A | 4/1998 | Buirge |
| 5,738,649 A | 4/1998 | Macoviak |
| 5,741,234 A | 4/1998 | Aboul-Hosn |
| 5,741,429 A | 4/1998 | Donadio, III et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,776,161 A | 7/1998 | Globerman |
| 5,776,190 A | 7/1998 | Jarvik |
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,859,482 A | 1/1999 | Crowell et al. |
| 5,868,702 A | 2/1999 | Stevens et al. |
| 5,868,703 A | 2/1999 | Bertolero et al. |
| 5,888,241 A | 3/1999 | Jarvik |
| 5,888,242 A | 3/1999 | Antaki et al. |
| 5,895,557 A | 4/1999 | Kronzer |
| 5,904,668 A | 5/1999 | Hlyman et al. |
| 5,911,685 A | 6/1999 | Siess et al. |
| 5,921,913 A | 7/1999 | Siess |
| 5,927,956 A | 7/1999 | Lim et al. |
| 5,941,813 A | 8/1999 | Sievers et al. |
| 5,951,263 A | 9/1999 | Taylor et al. |
| 5,957,941 A | 9/1999 | Ream |
| 5,964,694 A | 10/1999 | Siess et al. |
| 5,993,420 A | 11/1999 | Hyman et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,027,863 A | 2/2000 | Donadio, III |
| 6,053,705 A | 4/2000 | Schob et al. |
| 6,056,719 A | 5/2000 | Mickley |
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,106,494 A | 8/2000 | Saravia et al. |
| 6,109,895 A | 8/2000 | Ray et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,190,357 B1 | 2/2001 | Ferrari et al. |
| 6,200,260 B1 | 3/2001 | Bolling |
| 6,203,528 B1 | 3/2001 | Deckert et al. |
| 6,210,133 B1 | 4/2001 | Aboul-Hosn et al. |
| 6,210,318 B1 | 4/2001 | Lederman |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,228,063 B1 | 5/2001 | Aboul-Hosn |
| 6,234,960 B1 | 5/2001 | Aboul-Hosn et al. |
| 6,234,995 B1 | 5/2001 | Peacock, III |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,454,775 B1 | 9/2002 | Demarais et al. |
| 6,468,298 B1 | 10/2002 | Pelton |
| 6,494,694 B2 | 12/2002 | Lawless et al. |
| 6,503,224 B1 | 1/2003 | Forman et al. |
| 6,508,777 B1 | 1/2003 | Macoviak et al. |
| 6,508,787 B2 | 1/2003 | Reimund et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | Deblanc et al. |
| 6,565,598 B1 | 5/2003 | Lootz |
| 6,572,349 B2 | 6/2003 | Sorensen et al. |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,660,014 B2 | 12/2003 | Demarais et al. |
| 6,673,105 B1 | 1/2004 | Chen |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Frederik et al. |
| 6,794,784 B2 | 9/2004 | Takahashi et al. |
| 6,794,789 B2 | 9/2004 | Siess et al. |
| 6,814,713 B2 | 11/2004 | Aboul-Hosn et al. |
| 6,817,836 B2 | 11/2004 | Nose et al. |
| 6,818,001 B2 | 11/2004 | Wulfman et al. |
| 6,835,049 B2 | 12/2004 | Ray |

(56) References Cited

U.S. PATENT DOCUMENTS

| | | | |
|---|---|---|---|
| 6,860,713 B2 | 3/2005 | Hoover |
| 6,866,625 B1 | 3/2005 | Ayre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,901,289 B2 | 5/2005 | Dahl et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,962,488 B2 | 11/2005 | Davis et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,018,182 B2 | 3/2006 | O'Mahony et al. |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,214,038 B2 | 5/2007 | Saxer et al. |
| 7,229,258 B2 | 6/2007 | Wood et al. |
| 7,238,010 B2 | 7/2007 | Hershberger et al. |
| 7,241,257 B1 | 7/2007 | Ainsworth et al. |
| 7,262,531 B2 | 8/2007 | Li et al. |
| 7,264,606 B2 | 9/2007 | Jarvik et al. |
| 7,267,667 B2 | 9/2007 | Toude et al. |
| 7,284,956 B2 | 10/2007 | Nose et al. |
| 7,288,111 B1 | 10/2007 | Holloway et al. |
| 7,290,929 B2 | 11/2007 | Smith et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride et al. |
| 7,393,189 B2 | 7/2008 | Davis et al. |
| 7,469,716 B2 | 12/2008 | Parrino et al. |
| 7,478,999 B2 | 1/2009 | Limoges |
| 7,491,163 B2 | 2/2009 | Viole et al. |
| 7,534,258 B2 | 5/2009 | Gomez et al. |
| 7,547,200 B2 | 6/2009 | OMahony et al. |
| 7,605,298 B2 | 10/2009 | Bechert et al. |
| 7,619,560 B2 | 11/2009 | Penna et al. |
| 7,632,079 B2 | 12/2009 | Hershberger et al. |
| 7,633,193 B2 | 12/2009 | Masoudipour et al. |
| 7,645,225 B2 | 1/2010 | Medvedev et al. |
| 7,657,324 B2 | 2/2010 | Westlund et al. |
| 7,682,673 B2 | 3/2010 | Houston et al. |
| 7,722,568 B2 | 5/2010 | Lenker et al. |
| 7,731,675 B2 | 6/2010 | Aboul-Hosn et al. |
| 7,736,296 B2 | 6/2010 | Siess et al. |
| 7,744,566 B2 | 6/2010 | Pirovano et al. |
| 7,758,521 B2 | 7/2010 | Morris et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,811,279 B2 | 10/2010 | John |
| 7,819,833 B2 | 10/2010 | Ainsworth et al. |
| 7,820,205 B2 | 10/2010 | Takakusagi et al. |
| 7,828,710 B2 | 11/2010 | Shifflette |
| 7,841,976 B2 | 11/2010 | McBride et al. |
| 7,878,967 B1 | 2/2011 | Khanal |
| 7,927,068 B2 | 4/2011 | McBride et al. |
| 7,934,912 B2 | 5/2011 | Voltenburg, Jr. et al. |
| 7,935,102 B2 | 5/2011 | Breznock et al. |
| 7,942,804 B2 | 5/2011 | Khaw |
| 7,942,844 B2 | 5/2011 | Moberg et al. |
| 7,955,365 B2 | 6/2011 | Doty |
| 7,975,491 B2 * | 7/2011 | Smisson, III ........... A61M 5/36 165/185 |
| 7,993,259 B2 | 8/2011 | Kang et al. |
| 7,998,054 B2 | 8/2011 | Bolling |
| 7,998,190 B2 | 8/2011 | Gharib et al. |
| 8,012,079 B2 | 9/2011 | Delgado, III |
| 8,025,647 B2 | 9/2011 | Siess et al. |
| 8,052,399 B2 | 11/2011 | Stemple et al. |
| 8,062,008 B2 | 11/2011 | Voltenburg, Jr. et al. |
| 8,079,948 B2 | 12/2011 | Shifflette |
| 8,083,503 B2 | 12/2011 | Voltenburg, Jr. et al. |
| 8,110,267 B2 | 2/2012 | Houston et al. |
| 8,114,008 B2 | 2/2012 | Hidaka et al. |
| 8,123,669 B2 | 2/2012 | Siess et al. |
| 8,142,400 B2 | 3/2012 | Rotem et al. |
| 8,177,703 B2 | 5/2012 | Smith et al. |
| 8,206,350 B2 | 6/2012 | Mann et al. |
| 8,209,015 B2 | 6/2012 | Glenn |
| 8,216,122 B2 | 7/2012 | Kung |
| 8,235,943 B2 | 8/2012 | Breznock et al. |
| 8,236,040 B2 | 8/2012 | Mayberry et al. |
| 8,236,044 B2 | 8/2012 | Robaina |
| 8,255,050 B2 | 8/2012 | Mohl |
| 8,257,054 B2 | 9/2012 | Voltenburg, Jr. et al. |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,329,913 B2 | 12/2012 | Murata et al. |
| 8,333,687 B2 | 12/2012 | Arnan et al. |
| 8,348,991 B2 | 1/2013 | Weber et al. |
| 8,364,278 B2 | 1/2013 | Pianca et al. |
| 8,371,832 B2 | 2/2013 | Rotem et al. |
| 8,376,707 B2 | 2/2013 | McBride et al. |
| 8,382,818 B2 | 2/2013 | Davis et al. |
| 8,388,565 B2 | 3/2013 | Shifflette |
| 8,388,582 B2 | 3/2013 | Eubanks et al. |
| 8,409,128 B2 | 4/2013 | Ferrari |
| 8,439,859 B2 | 5/2013 | Pfeffer et al. |
| 8,449,443 B2 | 5/2013 | Rodefeld et al. |
| 8,485,961 B2 | 7/2013 | Campbell et al. |
| 8,489,190 B2 | 7/2013 | Pfeffer et al. |
| 8,491,285 B2 | 7/2013 | Haser et al. |
| 8,535,211 B2 | 9/2013 | Campbell et al. |
| 8,540,615 B2 | 9/2013 | Aboul-Hosn et al. |
| 8,545,379 B2 | 10/2013 | Marseille et al. |
| 8,545,380 B2 | 10/2013 | Farnan et al. |
| 8,579,858 B2 | 11/2013 | Reitan et al. |
| 8,585,572 B2 | 11/2013 | Mehmanesh |
| 8,591,393 B2 | 11/2013 | Walters et al. |
| 8,597,170 B2 | 12/2013 | Walters et al. |
| 8,617,239 B2 | 12/2013 | Reitan |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,784,441 B2 | 7/2014 | Rosenbluth et al. |
| 8,790,236 B2 | 7/2014 | LaRose et al. |
| 8,795,576 B2 | 8/2014 | Tao et al. |
| 8,801,590 B2 | 8/2014 | Mohl |
| 8,814,776 B2 | 8/2014 | Hastie et al. |
| 8,814,933 B2 | 8/2014 | Siess |
| 8,849,398 B2 | 9/2014 | Evans |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 9,089,634 B2 | 7/2015 | Schumacher et al. |
| 9,089,670 B2 | 7/2015 | Scheckel |
| 9,217,442 B2 | 12/2015 | Wiessler et al. |
| 9,308,302 B2 | 4/2016 | Zeng |
| 9,314,558 B2 | 4/2016 | Er |

(56) References Cited

U.S. PATENT DOCUMENTS

| | | | |
|---|---|---|---|
| 9,327,067 B2 | 5/2016 | Zeng et al. |
| 9,328,741 B2 | 5/2016 | Liebing |
| 9,358,330 B2 | 6/2016 | Schumacher |
| 2002/0010487 A1 | 1/2002 | Evans et al. |
| 2002/0047435 A1 | 4/2002 | Takahashi et al. |
| 2002/0094287 A1 | 7/2002 | Davis |
| 2003/0018380 A1 | 1/2003 | Craig et al. |
| 2003/0093086 A1 | 5/2003 | Briggs et al. |
| 2003/0205233 A1 | 11/2003 | Aboul-Hosn et al. |
| 2003/0208097 A1 | 11/2003 | Aboul-Hosn et al. |
| 2003/0225366 A1 | 12/2003 | Morgan et al. |
| 2003/0231959 A1 | 12/2003 | Snider |
| 2004/0010229 A1 | 1/2004 | Houde et al. |
| 2004/0116862 A1 | 6/2004 | Ray |
| 2004/0152944 A1 | 8/2004 | Medvedev et al. |
| 2004/0253129 A1 | 12/2004 | Sorensen et al. |
| 2005/0013698 A1 | 1/2005 | Davis |
| 2005/0027281 A1 | 2/2005 | Lennox |
| 2005/0049696 A1 | 3/2005 | Siess et al. |
| 2005/0085683 A1 | 4/2005 | Bolling et al. |
| 2005/0113631 A1 | 5/2005 | Bolling et al. |
| 2005/0137680 A1 | 6/2005 | Ortiz et al. |
| 2005/0165269 A9 | 7/2005 | Aboul-Hosn et al. |
| 2005/0218022 A1 | 10/2005 | Cervantes |
| 2005/0250975 A1 | 11/2005 | Carrier et al. |
| 2005/0277912 A1 | 12/2005 | John |
| 2006/0008349 A1 | 1/2006 | Khaw |
| 2006/0018943 A1 | 1/2006 | Bechert et al. |
| 2006/0058869 A1 | 3/2006 | Olson et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0167404 A1 | 7/2006 | Pirovano et al. |
| 2006/0264695 A1 | 11/2006 | Viole et al. |
| 2006/0270894 A1 | 11/2006 | Viole et al. |
| 2007/0100314 A1 | 5/2007 | Keren et al. |
| 2007/0142785 A1 | 6/2007 | Lundgaard et al. |
| 2007/0212240 A1 | 9/2007 | Voyeux et al. |
| 2007/0217932 A1 | 9/2007 | Voyeux et al. |
| 2007/0217933 A1 | 9/2007 | Haser et al. |
| 2007/0237739 A1 | 10/2007 | Doty |
| 2007/0248477 A1 | 10/2007 | Nazarifar et al. |
| 2008/0004645 A1 | 1/2008 | To et al. |
| 2008/0011640 A1 | 1/2008 | Cervantes |
| 2008/0015506 A1 | 1/2008 | Davis |
| 2008/0031953 A1 | 2/2008 | Takakusagi et al. |
| 2008/0103442 A1 | 5/2008 | Kesten et al. |
| 2008/0103516 A1 | 5/2008 | Wulfman et al. |
| 2008/0103591 A1 | 5/2008 | Siess |
| 2008/0114339 A1 | 5/2008 | McBride et al. |
| 2008/0119943 A1 | 5/2008 | Armstrong et al. |
| 2008/0132748 A1 | 6/2008 | Shifflette |
| 2008/0167679 A1 | 7/2008 | Papp |
| 2008/0200878 A1 | 8/2008 | Davis et al. |
| 2008/0275290 A1 | 11/2008 | Viole et al. |
| 2008/0306327 A1 | 12/2008 | Shifflette |
| 2009/0018567 A1 | 1/2009 | Escudero et al. |
| 2009/0024085 A1 | 1/2009 | To et al. |
| 2009/0053085 A1 | 2/2009 | Thompson et al. |
| 2009/0087325 A1 | 4/2009 | Voltenburg, Jr. et al. |
| 2009/0099638 A1 | 4/2009 | Grewe |
| 2009/0112312 A1 | 4/2009 | Larose et al. |
| 2009/0118567 A1 | 5/2009 | Siess |
| 2009/0163864 A1 | 6/2009 | Breznock et al. |
| 2009/0171137 A1 | 7/2009 | Farnan et al. |
| 2009/0182188 A1 | 7/2009 | Marseille et al. |
| 2009/0234378 A1 | 9/2009 | Escudero et al. |
| 2009/0306588 A1 | 12/2009 | Nguyen et al. |
| 2010/0004595 A1 | 1/2010 | Nguyen et al. |
| 2010/0030161 A1 | 2/2010 | Duffy |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0087773 A1 | 4/2010 | Ferrari |
| 2010/0094089 A1 | 4/2010 | Litscher et al. |
| 2010/0127871 A1 | 5/2010 | Pontin |
| 2010/0137802 A1 | 6/2010 | Yodfat et al. |
| 2010/0174239 A1 | 7/2010 | Yodfat et al. |
| 2010/0191035 A1 | 7/2010 | Kang et al. |
| 2010/0197994 A1 | 8/2010 | Mehmanesh |
| 2010/0210895 A1 | 8/2010 | Aboul-Hosn et al. |
| 2010/0268017 A1 | 10/2010 | Siess et al. |
| 2010/0274330 A1 | 10/2010 | Burwell et al. |
| 2010/0286210 A1 | 11/2010 | Murata et al. |
| 2010/0286791 A1 | 11/2010 | Goldsmith |
| 2011/0004046 A1 | 1/2011 | Campbell et al. |
| 2011/0004291 A1 | 1/2011 | Davis et al. |
| 2011/0009687 A1 | 1/2011 | Mohl |
| 2011/0015610 A1 | 1/2011 | Plahey et al. |
| 2011/0071338 A1 | 3/2011 | McBride et al. |
| 2011/0076439 A1 | 3/2011 | Zeilon |
| 2011/0106004 A1 | 5/2011 | Eubanks et al. |
| 2011/0152906 A1 | 6/2011 | Escudero et al. |
| 2011/0152907 A1 | 6/2011 | Escudero et al. |
| 2011/0218516 A1 | 9/2011 | Grigorov |
| 2011/0237863 A1 | 9/2011 | Ricci et al. |
| 2011/0300010 A1 | 12/2011 | Jarnagin et al. |
| 2012/0004495 A1 | 1/2012 | Bolling et al. |
| 2012/0029265 A1 | 2/2012 | LaRose et al. |
| 2012/0048407 A1* | 3/2012 | Paden ............... A61M 60/546 137/565.01 |
| 2012/0059213 A1 | 3/2012 | Spence et al. |
| 2012/0083740 A1 | 4/2012 | Chebator et al. |
| 2012/0142994 A1 | 6/2012 | Toellner |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2012/0184803 A1 | 7/2012 | Simon et al. |
| 2012/0220854 A1 | 8/2012 | Messerly et al. |
| 2012/0224970 A1 | 9/2012 | Schumacher et al. |
| 2012/0226097 A1 | 9/2012 | Smith et al. |
| 2012/0234411 A1 | 9/2012 | Scheckel et al. |
| 2012/0237357 A1 | 9/2012 | Schumacher et al. |
| 2012/0245404 A1 | 9/2012 | Smith et al. |
| 2012/0265002 A1 | 10/2012 | Roehn et al. |
| 2013/0041202 A1 | 2/2013 | Toellner et al. |
| 2013/0053622 A1 | 2/2013 | Corbett |
| 2013/0053623 A1 | 2/2013 | Evans et al. |
| 2013/0053693 A1 | 2/2013 | Breznock et al. |
| 2013/0066140 A1 | 3/2013 | McBride et al. |
| 2013/0085318 A1 | 4/2013 | Toellner et al. |
| 2013/0085319 A1 | 4/2013 | Evans et al. |
| 2013/0096364 A1 | 4/2013 | Reichenbach et al. |
| 2013/0103063 A1 | 4/2013 | Escudero et al. |
| 2013/0106212 A1 | 5/2013 | Nakazumi et al. |
| 2013/0129503 A1 | 5/2013 | McBride et al. |
| 2013/0138205 A1 | 5/2013 | Kushwaha et al. |
| 2013/0204362 A1 | 8/2013 | Toellner et al. |
| 2013/0209292 A1 | 8/2013 | Baykut et al. |
| 2013/0237744 A1 | 9/2013 | Pfeffer et al. |
| 2013/0245360 A1 | 9/2013 | Schumacher et al. |
| 2013/0303831 A1 | 11/2013 | Evans et al. |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2013/0345492 A1 | 12/2013 | Pfeffer et al. |
| 2014/0005467 A1 | 1/2014 | Farnan et al. |
| 2014/0010686 A1 | 1/2014 | Tanner et al. |
| 2014/0012065 A1 | 1/2014 | Fitzgerald et al. |
| 2014/0039465 A1 | 2/2014 | Heike et al. |
| 2014/0051908 A1 | 2/2014 | Khanal et al. |
| 2014/0067057 A1 | 3/2014 | Callaway et al. |
| 2014/0088455 A1 | 3/2014 | Christensen et al. |
| 2014/0148638 A1 | 5/2014 | LaRose et al. |
| 2014/0163664 A1 | 6/2014 | Goldsmith |
| 2014/0275725 A1 | 7/2014 | Govari et al. |
| 2014/0188086 A1 | 9/2014 | Schenck et al. |
| 2014/0255176 A1 | 9/2014 | Bredenbreuker et al. |
| 2014/0275726 A1 | 9/2014 | Zeng |
| 2014/0301822 A1 | 10/2014 | Scheckel |
| 2014/0303596 A1 | 10/2014 | Schumacher et al. |
| 2015/0025558 A1 | 1/2015 | Wulfman et al. |

(56) References Cited

U.S. PATENT DOCUMENTS

| | | |
|---|---|---|
| 2015/0031936 A1 | 1/2015 | Larose et al. |
| 2015/0051435 A1 | 2/2015 | Siess et al. |
| 2015/0051436 A1 | 2/2015 | Spanier et al. |
| 2015/0080743 A1 | 3/2015 | Siess et al. |
| 2015/0087890 A1 | 3/2015 | Spanier et al. |
| 2015/0141738 A1 | 5/2015 | Toellner et al. |
| 2015/0141739 A1 | 5/2015 | Hsu et al. |
| 2015/0151032 A1 | 6/2015 | Voskoboynikov et al. |
| 2015/0209498 A1 | 7/2015 | Franano et al. |
| 2015/0250935 A1 | 9/2015 | Anderson et al. |
| 2015/0290372 A1 | 10/2015 | Muller et al. |
| 2015/0343179 A1 | 12/2015 | Schumacher et al. |
| 2016/0184500 A1 | 6/2016 | Zeng |
| 2016/0250399 A1 | 9/2016 | Tiller et al. |
| 2016/0250400 A1 | 9/2016 | Schumacher |
| 2016/0256620 A1 | 9/2016 | Scheckel et al. |

FOREIGN PATENT DOCUMENTS

| | | |
|---|---|---|
| CN | 101820933 A | 9/2010 |
| EP | 0453234 A1 | 10/1991 |
| EP | 0533432 A1 | 3/1993 |
| EP | 1393762 A1 | 3/2004 |
| EP | 1591079 A1 | 11/2005 |
| EP | 1591079 B1 | 2/2008 |
| EP | 2263732 A2 | 12/2010 |
| EP | 2298374 A1 | 3/2011 |
| EP | 1207934 B1 | 8/2014 |
| EP | 2298374 B1 | 5/2016 |
| FR | 2267800 A1 | 11/1975 |
| FR | 2267800 B1 | 12/1976 |
| GB | 2239675 | 7/1991 |
| JP | H06114101 A | 4/1994 |
| JP | 10099447 A | 4/1998 |
| JP | H1099440 A | 4/1998 |
| JP | 2001079093 A | 3/2001 |
| JP | 2005514085 A | 5/2005 |
| JP | 2007252960 A | 10/2007 |
| JP | 2011000620 A | 1/2011 |
| JP | 2016515000 A | 5/2016 |
| JP | 6114101 B2 | 4/2017 |
| TW | 500877 B2 | 9/2002 |
| WO | 1989005164 A1 | 6/1989 |
| WO | 9526695 A2 | 10/1995 |
| WO | 1995026695 A2 | 10/1995 |
| WO | 9715228 A1 | 5/1997 |
| WO | 1997015228 A1 | 5/1997 |
| WO | 1997037697 A1 | 10/1997 |
| WO | 2000012148 A2 | 3/2000 |
| WO | 0019097 A1 | 4/2000 |
| WO | 2000019097 A1 | 4/2000 |
| WO | 0043062 A1 | 7/2000 |
| WO | 0069489 A1 | 11/2000 |
| WO | 2000069489 A1 | 11/2000 |
| WO | 2001017581 A2 | 3/2001 |
| WO | 0124867 A1 | 4/2001 |
| WO | 2001024867 A1 | 4/2001 |
| WO | 02070039 A2 | 9/2002 |
| WO | 2002070039 A2 | 9/2002 |
| WO | 03103745 A2 | 12/2003 |
| WO | 2005089674 A1 | 9/2005 |
| WO | 2005123158 A1 | 12/2005 |
| WO | 2009073037 A1 | 6/2009 |
| WO | 2009076460 A2 | 6/2009 |
| WO | 2010127871 A1 | 11/2010 |
| WO | 2010133567 A1 | 11/2010 |
| WO | 2010149393 A1 | 12/2010 |
| WO | 2011035926 A1 | 3/2011 |
| WO | 2011035929 A2 | 3/2011 |
| WO | 2011039091 A1 | 4/2011 |
| WO | 2011076439 A1 | 6/2011 |
| WO | 2011089022 A1 | 7/2011 |
| WO | 2011126895 A2 | 10/2011 |
| WO | 2012007140 A1 | 1/2012 |
| WO | 2012007141 A1 | 1/2012 |
| WO | 2012094534 A2 | 7/2012 |
| WO | 2013148697 A1 | 10/2013 |
| WO | 2013160407 A1 | 10/2013 |
| WO | 2014019274 A1 | 2/2014 |
| WO | 2015063277 A2 | 5/2015 |

OTHER PUBLICATIONS

Non-Final Office Action, dated Dec. 16, 2019 for related U.S. Appl. No. 15/920,553.

Final Office Action, dated Aug. 18, 2020 for related U.S. Appl. No. 15/920,553.

Non-Final Office Action, dated Aug. 18, 2020 for related U.S. Appl. No. 15/920,553.

Final Office Action, dated Feb. 2, 2021 for related U.S. Appl. No. 15/920,553.

EP Search Report and preliminary opinion for related EP Patent Application No. 21156867.0, dated Jun. 10, 2021, 6 pages.

Abiomed, "Impella 5.0 with the Impella Console, Circulatory Support System, Instructions for Use & Clinical Reference Manual," Jun. 2010, in 122 pages.

Abiomed—Recovering Hearts. Saving Lives., Impella 2.5 System, Instructions for Use, Jul. 2007, in 86 sheets.

Aboul-Hosn et al., "The Hemopump: Clinical Results and Future Applications", Assisted Circulation 4, 1995, in 14 pages.

Barras et al., "Nitinol—Its Use in Vascular Surgery and Other Applications," Eur. J. Vasc. Endovasc. Surg., 2000, pp. 564-569; vol. 19.

Biscarini et al., "Enhanced Nitinol Properties for Biomedical Applications," Recent Patents on Biomedical Engineering, 2008, pp. 180-196, vol. 1(3).

Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.

Compendium of Technical and Scientific Information for the HEMOPUMP Temporary Cardiac Assist System, Johnson & Johnson Interventional Systems, 1988, in 15 pages.

Dekker et al., "Efficacy of a New Intraaortic Propeller Pump vs the Intraaortic Balloon Pump*, An Animal Study", Chest, Jun. 2003, vol. 123, No. 6, pp. 2089-2095.

Duerig et al., "An Overview of Nitinol Medical Applications," Materials Science Engineering, 1999, pp. 149-160; vol. A273.

European Search Report received in European Patent Application No. 05799883.3, dated May 10, 2011, in 4 pages.

Extended European Search Report received in European Patent Application No. 07753903.9, dated Oct. 8, 2012, in 7 pages.

Extended European Search Report received in European Patent Application No. 13813687.4, dated Feb. 24, 2016, in 6 pages.

Extended European Search Report received in European Patent Application No. 14779928.2, dated Oct. 7, 2016, in 6 pages.

Grech, "Percutaneous Coronary Intervention. I: History and Development," BMJ., May 17, 2003, pp. 1080-1082, vol. 326.

Hsu et al., "Review of Recent Patents on Foldable Ventricular Assist Devices," Recent Patents on Biomedical Engineering, 2012, pp. 208-222, vol. 5.

Impella CPR®—Instructions for Use & Clinical Reference Manual (United States only), Abiomed, Inc., Jul. 2014, 148 pages, www.abiomed.com.

Impella LDR with the Impella® Controller—Circulatory Support System—Instructions for Use & Clinical Reference Manual (United States only), Abiomed, Inc., Sep. 2010, 132 pages, www.abiomed.com.

JOMED Reitan Catheter Pump RCP, Percutaneous Circulatory Support, in 10 pages, believed to be published prior to Oct. 15, 2003.

JOMED Reitan Catheter Pump RCP, Feb. 18, 2003, in 4 pages.

Krishnamani et al., "Emerging Ventricular Assist Devices for Long-Term Cardiac Support," National Review, Cardiology, Feb. 2010, pp. 71-76, vol. 7.

Kunst et al., "Integrated unit for programmable control of the 21F Hemopump and registration of physiological signals," Medical & Biological Engineering & Computing, Nov. 1994, pp. 694-696.

(56) References Cited

OTHER PUBLICATIONS

Mihaylov et al., "Development of a New Introduction Technique for the Pulsatile Catheter Pump," Artificial Organs, 1997, pp. 425-427; vol. 21(5).
Mihaylov et al., "Evaluation of the Optimal Driving Mode During Left Ventricular Assist with Pulsatile Catheter Pump in Calves," Artificial Organs, 1999, pp. 1117-1122; vol. 23(12).
Minimally Invasive Cardiac Assist JOMED Catheter PumpTM, in 6 pages, believed to be published prior to Jun. 16, 1999.
Morgan, "Medical Shape Memory Alloy Applications—The Market and its Products," Materials Science and Engineering, 2004, pp. 16-23, vol. A 378.
Morsink et al., "Numerical Modelling of Blood Flow Behaviour in the Valved Catheter of the PUCA-Pump, a LVAD," The International Journal of Artificial Organs, 1997, pp. 277-284; vol. 20(5).
Nishimura et al., "The Enabler Cannula Pump: A Novel Circulatory Support System," The International Journal of Artificial Organs, 1999, pp. 317-323; vol. 22(5).
Nullity Action against the owner of the German part DE 50 2007 005 015.6 of European patent EP 2 047 872 B1, dated Jul. 13, 2015, in 61 pages.
Petrini et al., "Biomedical Applications of Shape Memory Alloys," Journal of Metallurgy, 2011, pp. 1-15.
Raess et al., "Impella 2.5," J. Cardiovasc. Transl. Res., 2009, pp. 168-172, vol. 2(2).
Rakhorst et al., "In Vitro Evaluation of the Influence of Pulsatile Intraventricular Pumping on Ventricular Pressure Patterns," Artificial Organs, 1994, pp. 494-499, vol. 18(7).
Reitan, Evaluation of a New Percutaneous Cardiac Assist Device, Department of Cardiology, Faculty of Medicine, Lund University, Sweden, 2002, in 172 pages.
Reitan et al., "Hemodynamic Effects of a New Percutaneous Circulatory Support Device in a Left Ventricular Failure Model," ASAIO Journal, 2003, pp. 731-736, vol. 49.
Rothman, "The Reitan Catheter Pump: A New Versatile Approach for Hemodynamic Support", London Chest Hospital Barts & The London NHS Trust, Oct. 22-27, 2006 (TCT 2006: Transcatheter Cardiovascular Therapeutics 18th Annual Scientific Symposium, Final Program), in 48 pages.
Schmitz-Rode et al., "An Expandable Percutaneous Catheter Pump for Left Ventricular Support," Journal of the American College of Cardiology, 2005, pp. 1856-1861, vol. 45(11).
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
Sharony et al., "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).
Sharony et al., "Right Heart Support During Off-Pump Coronary Artery Surgery—A Multi-Center Study," The Heart Surgery Forum, 2002, pp. 13-16, vol. 5(1).
Sieβ et al., "Hydraulic refinement of an intraarterial microaxial blood pump", The International Journal of Artificial Organs, 1995, vol. 18, No. 5, pp. 273-285.
Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.
Smith et al., "First-In-Man Study of the Reitan Catheter Pump for Circulatory Support in Patients Undergoing High-Risk Percutaneous Coronary Intervention," Catheterization and Cardiovascular Interventions, 2009, pp. 859-865, vol. 73(7).
Sokolowski et al., "Medical Applications of Shape Memory Polymers," Biomed. Mater. 2007, pp. S23-S27, vol. 2.
"Statistical Analysis and Clinical Experience with the Recover® Pump Systems", Impella CardioSystems GmbH, Sep. 2005, 2 sheets.

Stoeckel et al., "Self-Expanding Nitinol Stents—Material and Design Considerations," European Radiology, 2003, in 13 sheets.
Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.
Verkerke et al., "Numerical Simulation of the PUCA Pump, A Left Ventricular Assist Device," Abstracts of the XIXth ESAO Congress, The International Journal of Artificial Organs, 1992, p. 543, vol. 15(9).
Wampler et al., "The Sternotomy Hemopump, A Second Generation Intraarterial Ventricular Assist Device," ASAIO Journal, 1993, pp. M218-M223, vol. 39.
Weber et al., "Principles of Impella Cardiac Support," Supplemental to Cardiac Interventions Today, Aug./Sep. 2009.
Extended European Search Report received in European Patent Application No. 13813867.2, dated Feb. 26, 2016, in 6 pages (THOR.092EP).
Extended European Search Report received in European Patent Application No. 13813687.4, dated Feb. 24, 2016, in 6 pages (THOR.093EP).
Ide et al., "Evaluation of the Pulsatility of a New Pulsatile Left Ventricular Assist Device—the Integrated Cardioassist Catheter—in Dogs," J. of Thorac and Cardiovasc Sur, Feb. 1994, pp. 569-0575, vol. 107(2).
Siess et al., "Systemanalyse und Entwicklung intravasaler Rotationspumpen zur Herzunterstutzung", Helmholtz-Institut fur Blomedixinische Technik an der RWTH Aachen, Jun. 24, 1998, in 105 pages.
Siess et al., "Basic design criteria for rotary blood pumps," H. Masuda, Rotary Blood Pumps, Springer, Japan, 2000, pp. 69-83.
Siess et al., "From a lab type to a product: A retrospective view on Impella's assist technology," Artificial Organs, 2001, pp. 414-421, vol. 25, No. 5, Blackwell Science, Inc., International Society for Artificial Organs.
Siess et al., "System analysis and development of intravascular rotation pumps for cardiac assist," Dissertation, Shaker Verlag, Aachen, 1999, 39 pages.
Stolinski et al., "The heart-pump interaction: effects of a microaxial blood pump," International Journal of Artificial Organs, 2002, pp. 1082-1088, vol. 25, Issue 11.
Supplemental European Search Report received from the European Patent Office in EP Application No. EP 05799883 dated Mar. 19, 2010, 3 pages.
Takagaki et al., "A Novel Miniature Ventricular Assist Device for Hemodynamic Support," ASAIO Journal, 2001, pp. 112-416; vol. 47.
Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).
Verkerke et al., "Numerical Simulation of the Pulsating Catheter Pump: A Left Ventricular Assist Device," Artificial Organs, 1999, pp. 924-931, vol. 23(10).
Verkerke et al., "The PUCA Pump: A Left Ventricular Assist Device," Artificial Organs, 1993, pp. 365-368, vol. 17(5).
Written Opinion received in International Patent Application No. PCT/US2003/04853, dated Feb. 25, 2004, 5 pages.
Extended European Search Report received in European Patent Application No. 14764392.8, dated Oct. 27, 2016, in 7 pages (THOR.097EP).
Federal and Drug Administration 510(k) Summary for Predicate Device IMPELLA 2.5 (K112892), prepared Sep. 5, 2012.
Extended European Search Report for European Patent Application No. 21156867.0, dated Jun. 10, 2021, 6 pages.
Nullity Action against the owner of the German part DE 50 2007 005 015.6 of European patent EP 2 04 7 872 81, dated Jul. 13, 2015, in 61 pages.
International Preliminary Examination Report received in International Patent Application No. PCT/US2003/04401, dated May 18, 2004, in 4 pages.

(56) References Cited

OTHER PUBLICATIONS

International Preliminary Examination Report received in International Patent Application No. PCT/US2003/04853, dated Jul. 26, 2004, in 5 pages.
International Preliminary Report on Patentability and Written Opinion of the International Searching Authority received in International Patent Application No. PCT/US2005/033416, dated Mar. 20, 2007, in 7 pages.
International Preliminary Report on Patentability and Written Opinion of the International Searching Authority received in International Patent Application No. PCT/US2007/007313, dated Sep. 23, 2008, in 6 pages.
International Preliminary Report on Patentability and Written Opinion received in International Patent Application No. PCT/US2014/020878, dated Sep. 15, 2015, in 8 pages.
International Search Report and Written Opinion received in International Patent Application No. PCT/US2015/026013, dated Jul. 8, 2015, in 12 pages.
International Search Report and Written Opinion received in International Patent Application No. PCT/US2005/033416, dated Dec. 11, 2006, in 8 pages.
International Search Report and Written Opinion received in International Patent Application No. PCT/US2007/007313, dated Mar. 4, 2008, in 6 pages.
International Search Report and Written Opinion received in International Patent Application No. PCT/US2012/020369, dated Jul. 30, 2012, in 10 pages.
International Search Report and Written Opinion received in International Patent Application No. PCT/US2012/020382, dated Jul. 31, 2012, in 11 pages.
International Search Report and Written Opinion received in International Patent Application No. PCT/US2012/020383, dated Aug. 17, 2012; in 9 pages.
International Search Report and Written Opinion received in International Patent Application No. PCT/US2012/020553, dated Aug. 17, 2012, in 8 pages.
International Search Report and Written Opinion received in International Patent Application No. PCT/US2013/040798, dated Aug. 21, 2013, in 16 pages.
International Search Report and Written Opinion received in International Patent Application No. PCT/US2013/040799, dated Aug. 21, 2013, in 19 pages.
International Search Report and Written Opinion received in International Patent Application No. PCT/US2013/040809, dated Sep. 2, 2013, in 25 pages.
International Search Report and Written Opinion received in International Patent Application No. PCT/US2013/048332, dated Oct. 16, 2013, in 17 pages.
International Search Report and Written Opinion received in International Patent Application No. PCT/US2013/048343, dated Oct. 11, 2013, in 15 pages.
International Search Report and Written Opinion received in International Patent Application No. PCT/US2014/020790, dated Aug. 6, 2014, in 11 pages.
International Search Report and Written Opinion received in International Patent Application No. PCT/US2014/020878, dated May 7, 2014, in 13 pages.
International Search Report and Written Opinion received in International Patent Application No. PCT/US2015/025959, dated Aug. 28, 2015, in 16 pages.
International Search Report and Written Opinion received in International Patent Application No. PCT/US2015/025960, dated Sep. 3, 2015, in 15 pages.
International Search Report and Written Opinion received in International Patent Application No. PCT/US2015/026014, dated Jul. 15, 2015, in 13 pages.
International Search Report and Written Opinion received in International Patent Application No. PCT/US2015/026025, dated Jul. 20, 2015, in 12 pages.
International Search Report and Written Opinion received in International Patent Application No. PCT/US2015/045370, dated Nov. 18, 2015, in 12 pages.
International Search Report and Written Opinion received in International Patent Application No. PCT/US2016/014371, dated May 2, 2016, in 18 pages (THOR.127WO).
International Search Report and Written Opinion received in International Patent Application No. PCT/US2016/014379, dated Jul. 25, 2016, in 19 pages (THOR.128WO).
International Search Report and Written Opinion received in International Patent Application No. PCT/US2016/014391, dated May 2, 2016, in 17 pages (THOR.130WO).
International Search Report and Written Opinion received in International Patent Application No. PCT/US2016/051553, dated Feb. 8, 2017, in 15 pages (THOR.134W0).
International Search Report received in International Patent Application No. PCT/US2003/004401, dated Nov. 10, 2003, in 9 pages.
International Search Report received in International Patent Application No. PCT/US2003/004853, dated Jul. 3, 2003, in 3 pages.
International Search Report Written Opinion received in International Patent Application No. PCT/US2010/040847, dated Dec. 14, 2010, in 17 pages.
Schmitz-Rode et al., "Axial flow catheter pump for circulatory support," Biomedizinische Technik, 2002, Band 47, Erganzungsband 1, Teil 1, pp. 142-143.
Ide et al., "Hemodynamic Evaluation of a New Left Ventricular Assist Device: An Integrated Cardioassist Catheter as a Pulsatile Left Ventricle—Femoral Artery Bypass," Blackwell Scientific Publications, Inc., 1992, pp. 286-290, vol. 16(3).
Extended European Search Report received in European Patent Application No. 14779928.2, dated Oct. 7, 2016, in 6 pages (THOR. 084EP).
Reitan et al., "Hydrodynamic Properties of a New Percutaneous Intra-Aortic Axial Flow Pump," ASAIO Journal 2000, pp. 323-328.

\* cited by examiner

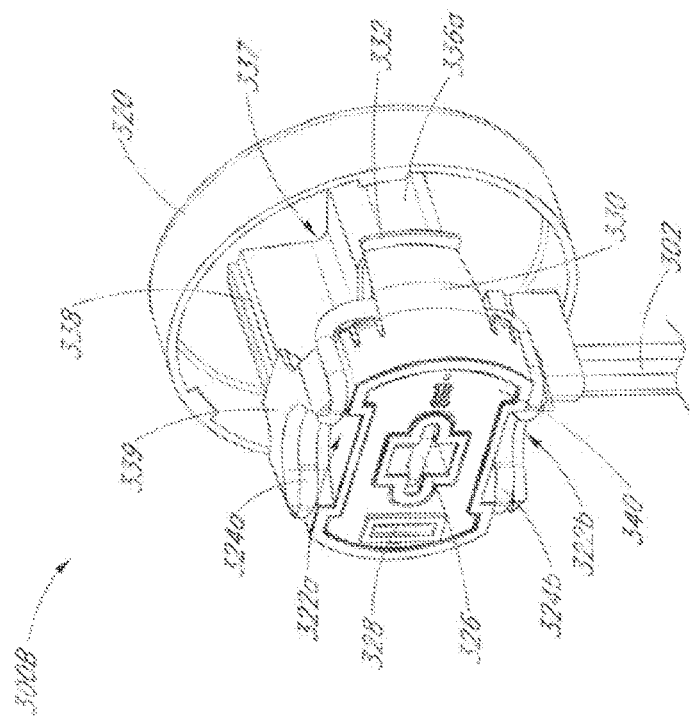
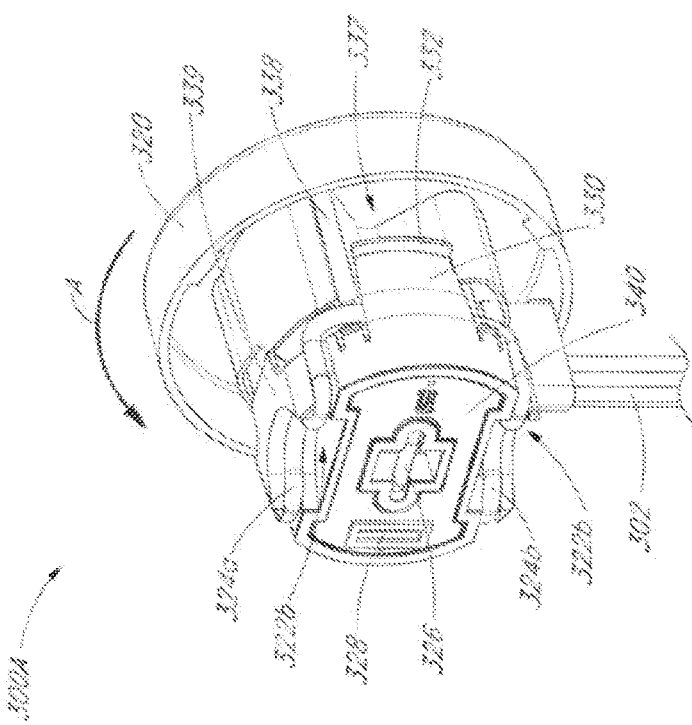

FIG. 31

FLUID HANDLING SYSTEM

CROSS REFERENCE TO RELATED APPLICATIONS

This application is a continuation of U.S. patent application Ser. No. 15/920,553, filed Mar. 14, 2018, which is a continuation of International Application No. PCT/US2016/051553, filed Sep. 13, 2016, which claims priority to U.S. Provisional Patent Application Nos. 62/218,508, filed Sep. 14, 2015, Provisional Patent Application No. 62/218,509, filed Sep. 14, 2015, U.S. Provisional Patent Application No. 62/220,040, filed Sep. 17, 2015, and is a Continuation in Part Application of U.S. application Ser. No. 15/198,342, filed Jun. 30, 2016, which claims priority to U.S. application Ser. No. 14/203,978, filed Mar. 11, 2014, which claims priority to U.S. Provisional Patent Application No. 61/780,656, filed Mar. 13, 2013, the entire contents of each of which are incorporated by reference herein in their entireties for all purposes.

BACKGROUND OF THE INVENTION

Field of the Invention

This application is directed to pumps for mechanical circulatory support of a heart. In particular, this application is directed to a console and controller for a catheter pump and a fluid handling system configured to convey and remove fluids to and from the catheter pump.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently, minimally-invasive rotary blood pumps have been developed in an attempt to increase the level of potential support (i.e., higher flow). A rotary blood pump is typically inserted into the body and connected to the cardiovascular system, for example, to the left ventricle and the ascending aorta to assist the pumping function of the heart. Other known applications pumping venous blood from the right ventricle to the pulmonary artery for support of the right side of the heart. An aim of acute circulatory support devices is to reduce the load on the heart muscle for a period of time, to stabilize the patient prior to heart transplant or for continuing support.

There is a need for improved mechanical circulatory support devices for treating acute heart failure. Fixed cross-section ventricular assist devices designed to provide near full heart flow rate are either too large to be advanced percutaneously (e.g., through the femoral artery without a cutdown) or provide insufficient flow.

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events. In one aspect, there is a need for a heart pump that can be placed minimally-invasively, for example, through a 15FR or 12FR incision. In one aspect, there is a need for a heart pump that can provide an average flow rate of 4 Lpm or more during operation, for example, at 62 mmHg of head pressure. While the flow rate of a rotary pump can be increased by rotating the impeller faster, higher rotational speeds are known to increase the risk of hemolysis, which can lead to adverse outcomes and in some cases death. Accordingly, in one aspect, there is a need for a pump that can provide sufficient flow at significantly reduced rotational speeds. These and other problems are overcome by the inventions described herein.

Furthermore, in various catheter pump systems, it can be important to provide fluids to an operative device of a catheter assembly (e.g., for lubrication of moving parts and/or treatment fluids to be delivered to the patient), and to remove waste fluids from the patient's body. A controller may be provided to control the flow into and out of the catheter assembly. It can be advantageous to provide improved mechanisms for engaging the catheter assembly with the controller, which may be housed in a console.

Additionally, there is a need to reduce the time to implantation and treatment. In the case of therapy for acute heart failure in particular, the time it takes to start therapy can be critical to survival and good outcomes. For example, a difference of several minutes can be the difference between recovery and permanent brain damage for patients suffering myocardial infarction or cardiogenic shock. Accordingly, a continuing need exists to provide pump systems that can be set up, primed, and inserted faster, easier, and more effectively.

It can be challenging to prepare the catheter pump system for a treatment procedure, and to automatically control the treatment procedure. For example, there may be an increased risk of user error and/or longer treatment preparation times. Conventional catheter pumps may provide the user or clinician with unclear guidance on how to proceed at various points during the procedure. Moreover, in conventional systems, it may take the user or clinician a considerable amount of time to prepare the system for use, which may unduly delay the treatment procedure. Furthermore, it can be challenging to prepare and/or operate the catheter pump system in arrangements that utilize an expandable impeller and/or an expandable cannula in which the impeller is disposed. For example, it can be challenging to account for expandable volume of the cannula during system preparation and/or operation. Furthermore, the parameters of the catheter pump system may deviate from norms in some instances and the deviation may not be easily identified by the user.

These and other problems are overcome by the inventions described herein.

SUMMARY

There is an urgent need for a pumping device that can be inserted percutaneously and also provide full cardiac rate flows of the left, right, or both the left and right sides of the heart when called for.

In one embodiment, a fluid handling system includes a console configured to connect with a first electrical interface that is configured to connect to a plurality of components of the fluid handling system, the console including a second electrical interface configured to connect with the first electrical interface, a display, and one or more hardware processors. A control system includes the one or more hardware processors and a non-transitory memory storing instructions that, when executed, cause the control system to: detect an electrical signal from a first component of the plurality of components of the fluid handling system responsive to a caretaker performing a first instruction; determine a system state of the fluid handling system based at least in part on the electrical signal from the first component; compare the system state with a predetermined state condition corresponding to said first instruction; and output an indication on the display of the system state.

In another embodiment, a removable interface member for a fluid handling system is disclosed. The interface member can include an interface body sized and shaped to be inserted into an interface aperture of a console housing. An electrical component can be disposed on the interface body. Furthermore, an occlusion bed can be disposed on the interface body. A tube segment can be disposed on the interface body near the occlusion bed. The interface body can be dimensioned such that when the interface body is inserted into the interface aperture of the console housing, a pump in the console housing is operably engaged with the tube segment and the occlusion bed, and an electrical interconnect in the console housing is electrically coupled with the electrical component on the interface body.

In yet another embodiment, a method for operably coupling an infusion system to a console housing is disclosed. The method can comprise positioning an interface body of the infusion system in an interface aperture of the console housing. The interface body can comprise an occlusion bed, a tube segment mounted on the interface body near the occlusion bed, and an electrical component. The method can further comprise inserting the interface body through the interface aperture until a pump roller of the console housing compresses the tube segment against the occlusion bed and until an electrical interconnect of the console housing is electrically coupled to the electrical component of the interface body.

In another embodiment, a method for priming a catheter assembly is disclosed. The catheter assembly can include an elongate body and an operative device. The method can comprise inserting the operative device of the catheter assembly into a priming vessel. The method can further comprise securing a proximal portion of the priming vessel to a distal portion of the elongate body, such that the elongate body is in fluid communication with the priming vessel. Fluid can be delivered through the elongate body and the priming vessel to expel air within the catheter assembly.

In certain embodiments, a control system for controlling priming of a catheter assembly is disclosed. The control system can include one or more hardware processors. The one or more hardware processors can be programmed to generate a first user interface including a first instruction corresponding to priming of a catheter assembly to remove gas from the catheter assembly prior to a treatment procedure. The one or more hardware processors can be further configured to monitor one or more sensors of a fluid handling system, the fluid handling system configured to prime the catheter assembly to remove the gas. The one or more hardware processors can determine a system condition based in part on the monitoring of the one or more sensors. Further, the one or more hardware processors can control an operation of a component of the fluid handling system based on the determined system condition. In an embodiment, the operation includes directing fluid distally through the catheter assembly to remove the gas.

In certain embodiments, a control system for controlling priming of a catheter assembly can include one or more hardware processors. The one or more hardware processors can be programmed to generate a first user interface including a first instruction corresponding to priming of a catheter assembly to remove gas from the catheter assembly prior to a treatment procedure. The one or more hardware processors can be further configured to monitor one or more sensors of a fluid handling system, the fluid handling system configured to prime the catheter assembly to remove the gas. The one or more hardware processors can determine a system condition based in part on the monitoring of the one or more sensors. Further, the one or more hardware processors can generate an alarm based on the determined system condition. In an embodiment, the one or more hardware processors can also control an operation of a component of the fluid handling system based on the determined system condition and/or the alarm.

The control system of the preceding two paragraphs can have any sub-combination of the following features: wherein the determination of the system condition includes determining the first instruction was completed; wherein the determination of the system condition further includes determining the first instruction was completed based on a user input; wherein the determination of the system condition further includes determining operating parameters of a motor; wherein the motor can drive a pump that directs fluid distally through the catheter assembly to remove the gas; wherein the system condition includes gas in pressurized saline supply line or reduced saline flow to a lumen of the catheter assembly; wherein the system condition includes temperature of a motor over a threshold temperature; wherein the system condition includes a flow rate below a threshold; wherein the system condition includes connection state of at least one of a plurality of components of the fluid handling system; wherein the one or more hardware processors can determine the connection state based on a flow of current across two electrical terminals; wherein at least one of the plurality of components comprise a cassette, wherein the cassette can include a puck; wherein the one or more hardware processors can additionally control operation of an impeller to pump blood based on the determined system condition; wherein the one or more hardware processors can further control operation of an impeller motor that imparts rotation to the impeller to pump the blood; determine a current drawn by the impeller motor; compare the drawn current with a current threshold; shut down the impeller motor based on the comparison; determine a flow rate generated by the impeller motor; determine a speed of the impeller motor; control operation of the impeller motor based on at least two of the following: the determined flow rate, the speed, and the drawn current; wherein the system condition includes volume of saline in a saline bag; wherein the system condition includes at least one of: blockage in outer sheath and reduced pressure in the outer sheath; wherein the system condition includes a volume of waste bag over a threshold; wherein the system condition includes an amount time of cannula in the patient over a threshold; wherein the system condition includes a battery status; wherein the system condition includes a position of a cannula; wherein the component includes power electronics and wherein the one or more hardware processors can transmit a drive signal to the power electronics, the drive signal can to increase or decrease power transmitted by the power electronics; wherein the component includes a display and wherein the one or more hardware processors can generate a second user interface and transmit the second user interface to the display responsive to the determined system condition; wherein the component includes an alarm that can provide an indication to a user; wherein the one or more sensors comprise one or more pressure sensors; wherein the one or more sensors include one or more Hall sensors; wherein the one or more sensors include one or more temperature sensors; wherein the one or more sensors include one or more bubble detector sensors; wherein the one or more sensors include at least one of the following electrical circuit components: a resistor, a constant current source, and a constant voltage source; wherein the one or more hardware processors can detect connection state between a cassette and a console of the fluid handling system, send instructions to begin priming based on the detected connection state between the cassette and the console and the determined system state; wherein the detection of the connection state includes measuring a flow of current or voltage across two electrical terminals; wherein the component includes an impeller motor that can rotate an impeller to pump blood; wherein the one or more hardware processors can generate an alarm based on the determined system condition.

In certain embodiments, a method controlling priming of a catheter assembly can include generating a first user interface including a first instruction corresponding to priming of a catheter assembly to remove gas from the catheter assembly prior to a treatment procedure. The method can further include monitoring one or more sensors of a fluid handling system, the fluid handling system configured to prime the catheter assembly to remove the gas. The method can additional include the step of determining a system condition based in part on the monitoring of the one or more sensors. In some embodiment, the method can further include controlling an operation of a component of the fluid handling system based on the determined system condition. In an embodiment, the operation includes directing fluid distally through the catheter assembly to remove the gas.

The method of the preceding paragraph can have any sub-combination of the following features: wherein the detection of the connection state comprises measuring a flow of current or voltage across two electrical terminals wherein the sending instructions comprises sending a drive signal to a motor configured to drive a pump that directs fluid distally through the catheter assembly to remove the gas. The method of the preceding paragraph can also include any of the features described in paragraph 19 above.

In some embodiments, a control system can control operation of a catheter assembly. The control system can include one or more hardware processors. The one or more hardware processors can transmit a drive signal to an impeller motor configured to impart rotation to an impeller to pump blood. The one or more hardware processors can receive electrical signals from at least one of the following: a plurality of sensors, a cassette connector, and the impeller motor. The one or more hardware processors can determine one or more motor parameters from the received electrical signals. The one or more hardware processors can also change operating parameters of the impeller motor based on the determined one or more motor parameters, thereby controlling pumping of blood.

The control system of the preceding paragraph can have any sub-combination of the following features: wherein the one or more motor parameters include a current drawn by the impeller motor; wherein the one or more hardware processors can compare the current drawn by the impeller motor to a threshold current; the threshold current includes a value greater than 1 ampere; wherein the one or more motor parameters include a flow rate generated by the impeller motor; wherein the one or more motor parameters include a temperature of the impeller motor; wherein the one or more motor parameters include a motor speed; wherein the changing of operating parameters of the impeller motor based on the determined motor parameters includes comparing the determined one or more motor parameters to one or more predetermined thresholds. In an embodiment, the control system of the preceding paragraph can use any of the features described in paragraph 19.

In an embodiment, a fluid handling system can include a console that can connect with a first electrical interface of a cassette which can connect to a plurality of components of the fluid handling system. The console can further include a second electrical interface that can connect with the first electrical interface, a display, and one or more hardware processors. The fluid handling system can include a control system that includes the one or more hardware processors. The control system can detect an electrical signal from a first component of the plurality of components of the fluid handling system responsive to a caretaker performing a first instruction. The control system can determine a system state of the fluid handling system based at least in part on the electrical signal from the first component. The control system can compare the system state with a predetermined state condition corresponding to said first instruction.

The fluid handling system of the preceding paragraph can have any sub-combination of the following features: wherein the control system can generate a first user interface including a visual indication of the first instruction; generate a second user interface including a visual indication of a second instruction based at least on the comparison indicating that the system state is within predetermined state condition and the first instruction is completed; generate an alarm based at least on said comparison indicating that the system state is not within predetermined state condition; detect connection state between the cassette and the console; send instructions to begin priming based on the detected connection state between the cassette and the console and the determined system state; determine a temperature of an impeller moto that rotates the impeller to pump blood and shut off the impeller motor responsive to the determination of the temperature of the impeller motor; to determine a current drawn by the impeller motor and shut off the impeller motor responsive to the determination of the current drawn by the impeller motor; to determine blockage of fluid in a catheter and trigger an alarm based on the determination of blockage. The control system of the fluid handling system of the preceding paragraph can also utilize any of the features of paragraph 19.

In some embodiments, a computer storage system including a non-transitory storage device can include stored executable program instructions. The program instructions can direct a computer system to generate a first user interface including a first instruction corresponding to priming of a catheter assembly to remove gas from the catheter assembly prior to a treatment procedure. The program instructions can further direct the computer system to monitor one or more sensors of a fluid handling system, the fluid handling system configured to prime the catheter assembly to remove the gas. The program instructions can further direct the computer system determine a system condition based in part on the monitoring of the one or more sensors. Further, the program instructions can direct the computer system to control an operation of a component of the fluid handling system based on the determined system condition. In an embodiment, the operation includes directing fluid distally through the catheter assembly to remove the gas. The program instruction can also direct the computer system to generate an alarm based on the determined system conditions. In some embodiment, the program instructions can direct the computer system to use or execute any of the features of paragraph 19.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 5B is a three-dimensional perspective view of an interface member in an unlocked configuration.

FIG. 5C is a three-dimensional perspective view of an interface member in a locked configuration.

FIG. 21 illustrates a user interface corresponding to hanging waste bag on hook, according to one embodiment.

FIG. 22 illustrates user interface generated by the control system for instructions corresponding to the sixth step in the prepping process, according to one embodiment.

FIG. 23 illustrates a user interface generated by the control system including instruction to unclamp the line connecting to the pressurized saline bag, according to one embodiment.

FIG. 24 illustrates a user interface generated by the control system including instructions to insert cassette into the console, according to one embodiment.

FIG. 31 illustrates a user interface generated by the control system based on a detection of temperature of the handle, according to one embodiment.

Figure 1:
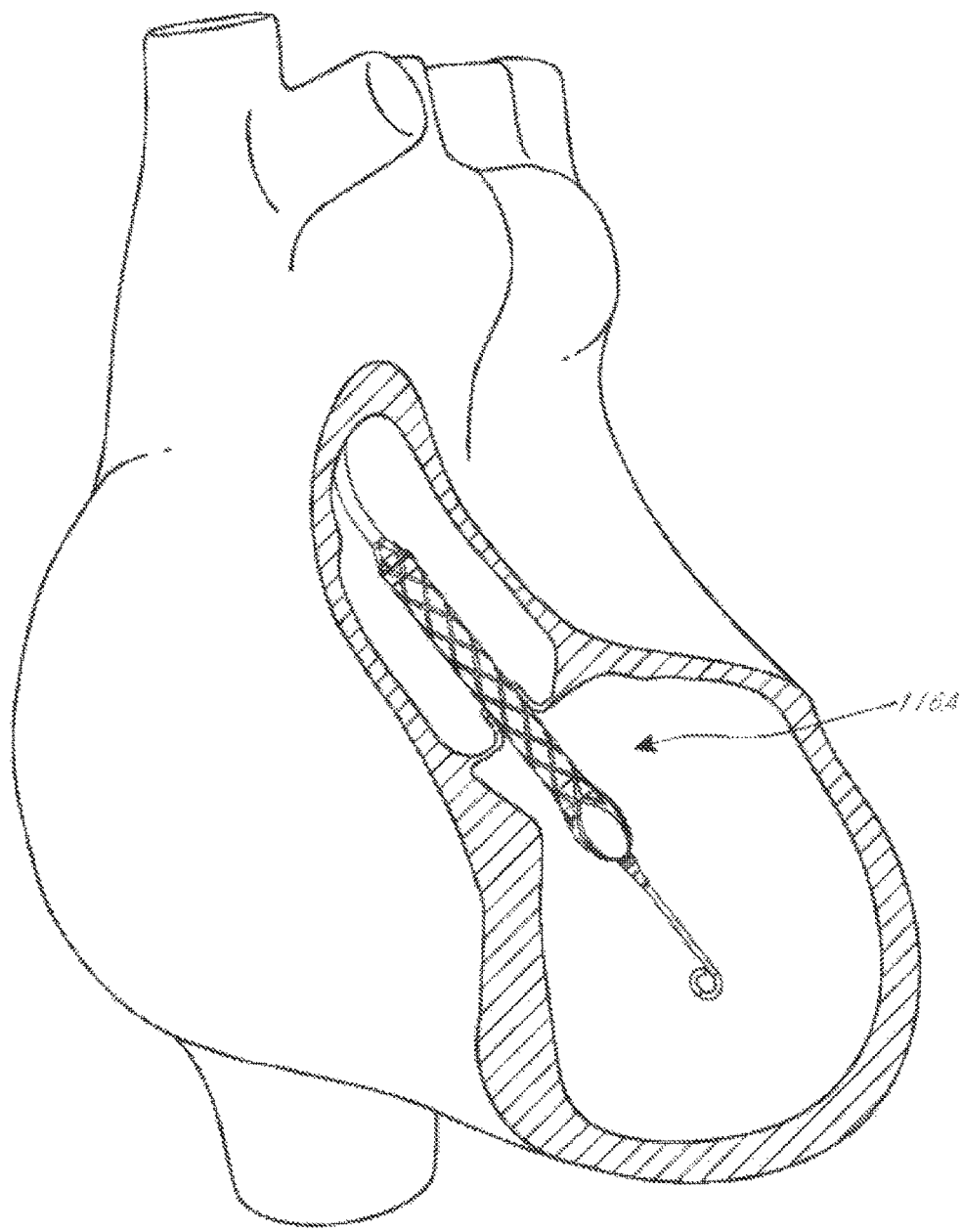
FIG. 1 is a schematic view of an operative device of a catheter assembly in position within the anatomy for assisting the left ventricle.

More detailed descriptions of various embodiments of components for heart pumps useful to treat patients experiencing cardiac stress, including acute heart failure, are set forth below.

DETAILED DESCRIPTION

This application is directed to fluid handling systems that are configured to control and/or manage fluid and electrical pathways in a catheter assembly, such as a catheter assembly of a percutaneous heart pump system. In particular, the disclosed percutaneous heart pump systems may include a catheter assembly and a console that includes a controller configured to control the fluid and electrical pathways that pass through the catheter assembly. Some of the disclosed embodiments generally relate to various configurations for coupling and engaging the catheter assembly with the console. For example, the console may be configured to control the flow rate of the pump and to monitor various physiological parameters and pump performance through the various electrical and fluid pathways of the catheter assembly. In some arrangements, the catheter assembly may be disposable, such that the catheter assembly can be discarded after use, while the console and controller are reusable. In embodiments with a reusable console and a disposable catheter assembly (or, indeed, in any embodiments where consoles and catheter assemblies may be coupled), it can be desirable to provide an effective interface between the catheter assembly and the console that completes the various fluid and electrical connections between the catheter assembly and the console.

In particular, it can be advantageous to provide an interface member at a proximal portion of the catheter assembly that is removably engageable with the console. Furthermore, to enhance usability and to minimize mistakes in making the connections, it can be important to make the interface easy to use so that users can easily connect the catheter assembly to the console before use and easily remove the catheter assembly from the console after use. Moreover, it can be important that the interface provides a secure connection between the interface member of the catheter assembly and an interface region of the console to ensure that the catheter assembly remains connected to the console uninterrupted during treatment.

As explained herein, one example of a catheter assembly is used in a percutaneous heart pump system having an operative device (e.g., an impeller assembly) that is configured to assist the patient's heart in pumping blood. The heart pump system may be configured to at least temporarily support the workload of the left ventricle in some embodiments. The exemplary heart pump can be designed for percutaneous entry through the femoral artery to a patient's heart. In particular, the exemplary impeller assembly can include a collapsible impeller and cannula, which can be inserted into the patient's vasculature at a catheter size of less than 13 FR, for example, about 12.5 FR in some arrangements. During insertion through the patient's vascular system to the heart, a sheath may maintain the impeller and cannula assembly in a stored configuration. When the impeller assembly is positioned in the left ventricle (or another chamber of a patient's heart), the impeller and cannula can expand to a larger diameter, for example to a catheter size of about 24 FR when the sheath is removed from the impeller assembly. The expanded diameter of the impeller and cannula may allow for the generation of higher flow rates, according to some embodiments.

For example, FIG. 1 illustrates one use of the disclosed catheter pump system. A distal portion of the pump, which can include an impeller assembly 116A, is placed in the left ventricle (LV) of the heart to pump blood from the LV into the aorta. The pump can be used in this way to treat patients with a wide range of conditions, including cardiogenic shock, myocardial infarction, and other cardiac conditions, and also to support a patient during a procedure such as percutaneous coronary intervention. One convenient manner of placement of the distal portion of the pump in the heart is by percutaneous access and delivery using the Seldinger technique, or other methods familiar to cardiologists. These approaches enable the pump to be used in emergency medicine, a catheter lab and in other non-surgical settings. Modifications can also enable the pump 10 to support the right side of the heart. Example modifications that could be used for right side support include providing delivery features and/or shaping a distal portion that is to be placed through at least one heart valve from the venous side, such as is discussed in U.S. Pat. Nos. 6,544,216; 7,070,555; and US 2012-0203056A1, all of which are hereby incorporated by reference herein in their entirety for all purposes.

Figure 2:
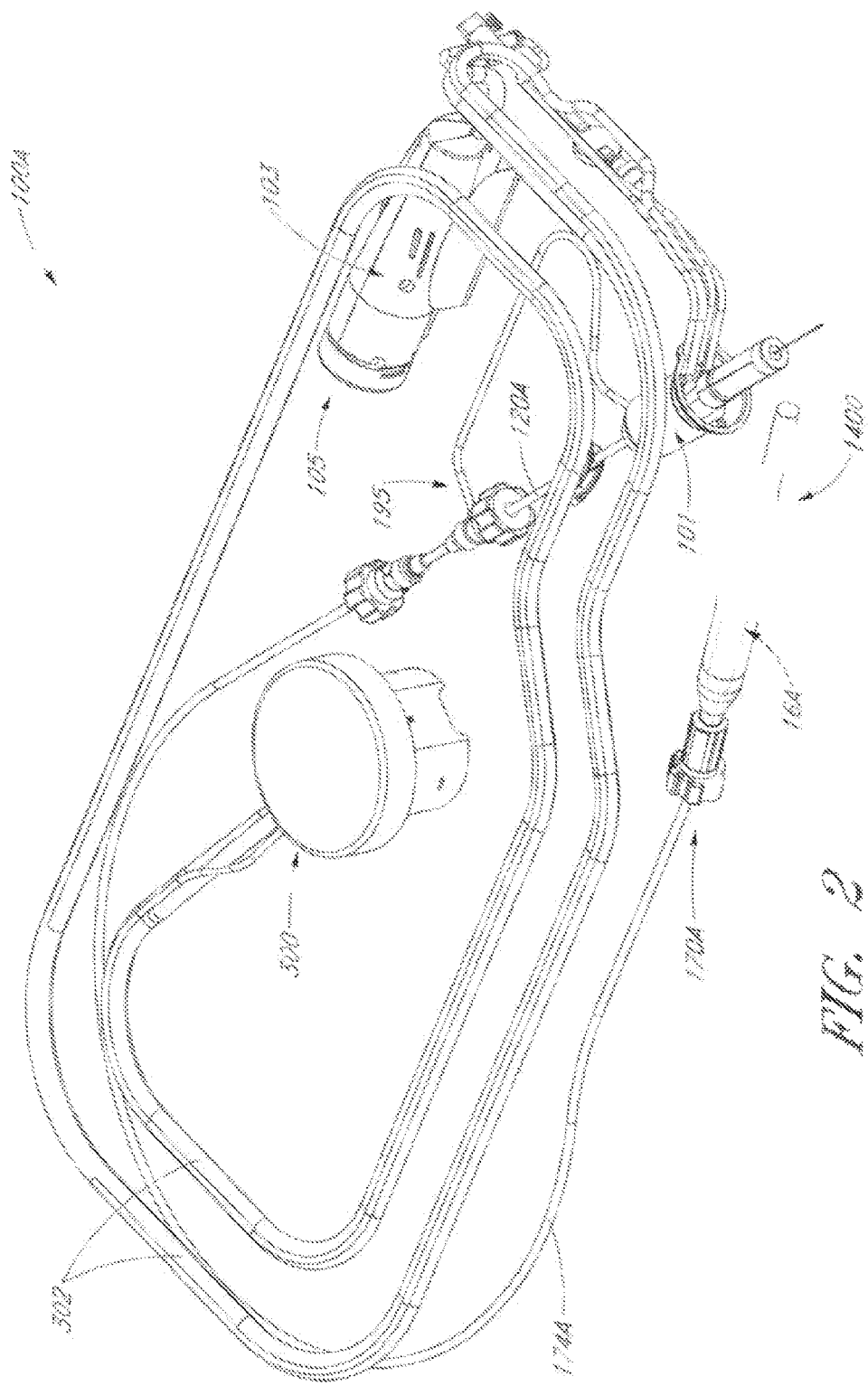
FIG. 2 is a three-dimensional perspective view of a catheter assembly, according to some embodiments.

Turning to FIG. 2, a three-dimensional perspective view of a catheter assembly 100A is disclosed. The catheter assembly 100A may correspond to the disposable portion of the heart pump systems described herein. For example, the catheter assembly 100A may include the impeller assembly 116A near a distal portion of the catheter assembly 100A, an elongate body 174A extending proximally from the impeller assembly 116A, an infusion system 195 configured to supply infusate to the catheter assembly 100A, a motor assembly comprising a driven assembly 101 and a drive assembly 103, one or more conduits 302 (e.g., electrical and/or fluid conduits) extending proximally from the motor assembly, and an interface member 300 coupled at a proximal portion of the conduits 302.

Moving from the distal end of the catheter assembly 100A of FIG. 2 to the proximal end, the impeller assembly 116A may be disposed at a distal portion of the catheter assembly 100A. As explained above, the impeller assembly 116A can include an expandable cannula or housing and an impeller with one or more blades. As the impeller rotates, blood can be pumped proximally (or distally in some implementations) to function as a cardiac assist device. A priming apparatus 1400 can be disposed over the impeller assembly 116A. As explained herein with reference to FIGS. 7-8, the priming apparatus 1400 can be configured to expedite a process of expelling air from the catheter assembly 100A before insertion of the operative device of the catheter assembly into the patient.

With continued reference to FIG. 2, the elongate body 174A extends proximally from the impeller assembly 116A to an infusion system 195 configured to allow infusate to enter the catheter assembly 100A and waste fluid to leave the catheter assembly 100A. A catheter body 120A (which also passes through the elongate body 174A) can extend proximally and couple to the driven assembly 101 of the motor assembly. The catheter body 120A can pass within the elongate body 174A, such that the elongate body 174A can axially translate relative to the catheter body 120A. Axial translation of the elongate body 174A relative to the catheter body 120A can enable the expansion and collapse of the impeller assembly 116A. For example, the impeller assembly 116A, coupled to a distal portion of the catheter body 120A, may expand into an expanded state by moving the elongate body 174A proximally relative to the impeller assembly 116A. The impeller assembly 116A may self-expand into the expanded state in some embodiments. In the expanded state, the impeller assembly 116A is able to pump blood at high flow rates. After the treatment procedure, the impeller assembly 116A may be compressed into a collapsed state by advancing a distal portion 170A of the elongate body 174A distally over the impeller assembly 116A to cause the impeller assembly 116A to collapse.

As explained above, the catheter body 120A can couple to the driven assembly 101 of the motor assembly. The driven assembly 101 can be configured to receive torque applied by the drive assembly 103, which is shown as being decoupled from the driven assembly 101 and the catheter assembly 100A in FIG. 2. The drive assembly 103 can be coupled to the driven assembly 101 by engaging a proximal portion of the driven assembly 101 with the drive assembly, e.g., by inserting the proximal portion of the driven assembly 101 into an aperture 105 of the drive assembly 103.

Although not shown in FIG. 2, a drive shaft can extend from the driven assembly 101 through the catheter body 120A to couple to an impeller shaft at or proximal to the impeller assembly 116A. The drive assembly 103 can electrically communicate with a controller in a console (see, e.g., FIGS. 3A-3B), which can be configured to control the operation of the motor assembly and the infusion system 195 that supplies a flow of infusate in the catheter assembly 100A. The impeller of the impeller assembly 116A may thus be rotated remotely by the motor assembly during operation of the catheter pump in various embodiments. For example, the motor assembly can be disposed outside the patient. In some embodiments, the motor assembly is separate from the controller or console, e.g., to be placed closer to the patient. In other embodiments, the motor assembly is part of the controller. In still other embodiments, the motor assembly is miniaturized to be insertable into the patient. Such embodiments allow the drive shaft to be much shorter, e.g., shorter than the distance from the aortic valve to the aortic arch (about 5 cm or less). Some examples of miniaturized motors catheter pumps and related components and methods are discussed in U.S. Pat. Nos. 5,964,694; 6,007,478; 6,178,922; and 6,176,848, all of which are hereby incorporated by reference herein in their entirety for all purposes.

As shown in FIG. 2, the motor assembly (e.g., the drive assembly 103 and the driven assembly 101) is in electrical communication with the controller and console by way of the conduits 302, which may include electrical wires. In particular, as shown in FIG. 2, the electrical wires may extend from the motor assembly proximally to the interface member 300. To enable the controller in the console to electrically communicate with the motor assembly and/or other sensors in the catheter assembly 100A (such as pressure sensors, flow sensors, temperature sensors, bubble detectors, etc.), it can be advantageous to provide a reliable electrical connection between the interface member 300 and the console. In various embodiments disclosed herein, therefore, the removable interface member 300 may include electrical components configured to couple to one or more electrical contacts (sometimes referred to herein as interconnections) in the console. The electrical connections may be achieved in a simple, user-friendly manner. In various embodiments disclosed herein, for example, the electrical connections may be made substantially at the same time, e.g., substantially simultaneously, as fluid connections are made between the interface member 300 and console. These and other structures incorporated to reduce the complexity of operating the pump system are provided to reduce the chance of errors in set-up and delays, which for the emergency conditions in which the pump may be implemented could be life-threatening.

The mechanical components rotatably supporting the impeller within the impeller assembly 116A permit high rotational speeds while controlling heat and particle generation that can come with high speeds. The infusion system 195 may deliver a cooling and lubricating solution to the distal portion of the catheter assembly 100A for these purposes. As shown in FIG. 2, the infusion system 195 may be in fluid communication with the interface member 300 by way of the conduits 302, which may also include fluid conduits or tubes. Because the catheter assembly 100A may be disposable and/or removable from a console, it can be important to securely couple interface member 300 to the console. Furthermore, it can be important to provide an easy-to-use interface such that users can easily complete fluid connections that remain secure during a treatment procedure. Maintaining security of the connection is important because the fluids and signals carried by the conduits 302 enable the impeller to operate in a continuous manner. Stoppage of the pump system may require the catheter assembly 100A to be removed from the patient and replaced in certain circumstances, which may be life-threatening or extremely inconvenient at a minimum.

When activated, the catheter pump system can effectively increase the flow of blood out of the heart and through the patient's vascular system. In various embodiments disclosed herein, the pump can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump can be configured to produce an average flow rate at 62 mmHg pressure head of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

Various aspects of the pump and associated components are similar to those disclosed in U.S. Pat. Nos. 7,393,181; 8,376,707; 7,841,976; 7,022,100; and 7,998,054, and in U.S. Pub. Nos. 2011/0004046; 2012/0178986; 2012/0172655; 2012/0178985; and 2012/0004495, the entire contents of each of which are incorporated herein for all purposes by reference. In addition, this application incorporates by reference in its entirety and for all purposes the subject matter disclosed in each of the following concurrently filed applications: application Ser. No. 13/802,556, entitled "DISTAL BEARING SUPPORT," filed on Mar. 13, 2013; application Ser. No. 13/801,833, entitled "SHEATH SYSTEM FOR CATHETER PUMP," filed on Mar. 13, 2013; application Ser. No. 13/802,570, entitled "IMPELLER FOR CATHETER PUMP," filed on Mar. 13, 2013; application Ser. No. 13/801,528, entitled "CATHETER PUMP," filed on Mar. 13, 2013; and application Ser. No. 13/802,468, entitled "MOTOR ASSEMBLY FOR CATHETER PUMP," filed on Mar. 13, 2013.

Fluid Handling System

Figure 3B:
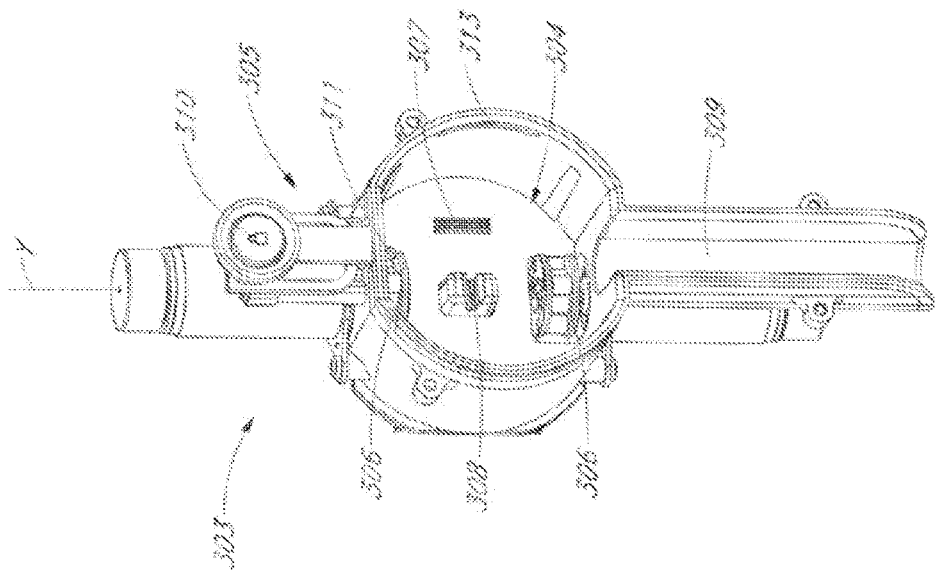
FIG. 3B is a three-dimensional perspective view of an interface region of the console shown in FIG. 3A.
Figure 3A:
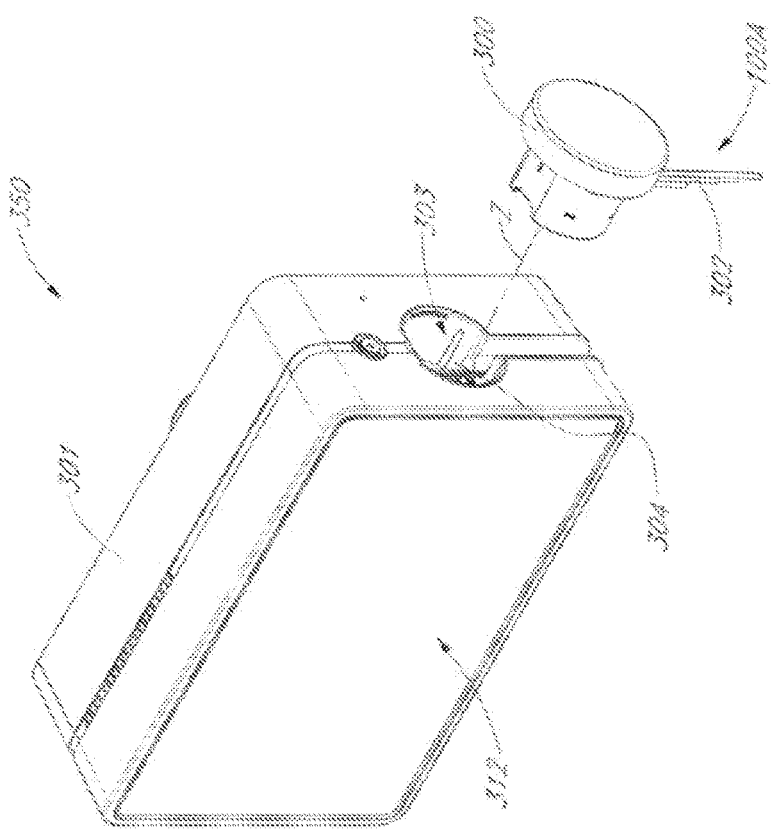
FIG. 3A is a three-dimensional perspective view of a fluid handling system that includes a console and catheter assembly.

FIG. 3A is a three-dimensional perspective view of a fluid handling system 350 that includes a console 301 and the catheter assembly 100A of FIG. 2. The console 301 can provide electrical power, control signals, medical fluids (e.g., saline) for infusion, and fluid waste extraction to the catheter assembly 100A by way of its interface with the interface member 300. In this manner, a plurality of fluid connections can advantageously be made with a single interface. As illustrated in FIG. 2, for example, the removable interface member 300 may be disposed at a proximal portion of the catheter assembly 100A and may be configured to couple to the console 301 at an interface region 303.

In some embodiments, the fluid handling system 350 can be configured to deliver fluids to and/or remove fluids from the catheter assembly 100A. As discussed above and in the incorporated patent references, saline and/or other medical solutions can lubricate and/or cool component between the motor assembly and the operative device. If desired, waste fluids can be removed from the catheter assembly 100A using the fluid handling system 350. In some embodiments, the fluid handling system 350 can include a multilumen catheter body having a proximal end and a distal end. The catheter body can include one or more lumens through which medical solutions (e.g., saline), waste fluids, and/or blood can flow. To drive fluid through the catheter assembly 100A (e.g., into and/or out of the catheter assembly 100A), the console 301 may include one or more pump(s) configured to apply positive or negative pressure to the catheter assembly 100A when the catheter assembly 100A is coupled to the console 301 and engages the pump(s).

In addition, the fluid handling system 350 may also be configured to provide electrical communication between the console 301 and the catheter assembly 100A. For example, the console can include a controller (e.g., a processor) that is programmed to control and/or manage the operation of the motor assembly. The console 301 may also include electrical interfaces configured to supply power to the motor assembly and/or other components that are driven by electrical power when the interface member 300 is coupled to the console 301. Moreover, one or more electrical or electronic sensors may be provided in the catheter assembly 100A and may electrically couple to the console 301 by way of the fluid handling system 350. The embodiments disclosed herein may thereby provide fluid and electrical connections between the catheter assembly 100A and the console 301.

As explained above, the fluid handling system 350 may provide a removable interface between the catheter assembly 100A and the console 301, which may include various components, including, e.g., one or more pump(s), processors (e.g., the controller), electrical interconnections, etc. For example, to activate one or more pumps in the console 301 and/or to engage one or more electrical connections between the console 301 and the interface member 300, a user may simply insert a distal portion of the interface member 300 (e.g., including a closure member) along the illustrated Z-direction into an aperture 304 of the interface region 303 until the pump(s) are engaged and the electrical connection(s) are formed. In some aspects, the insertion of the interface member along the Z-direction may engage the pump(s) and complete the electrical connection(s) substantially simultaneously.

In some embodiments, the interface member 300 may be secured to the console 301 by engaging a locking device between the interface region 303 and the interface member 300. One convenient way to engage a locking device is by rotating a portion of the interface member 300 relative to another portion of the interface member or relative to the console 301, as explained herein. For example, rotation of an outermost structure (opposite the direction Z), sometimes referred to herein as a "cap" relative to the console may engage a locking mechanism configured to mechanically secure the interface member 300 to the console 301 to prevent the interface member 300 from being accidentally disengaged during a treatment procedure.

The console 301 may also include a user interface 312, which may comprise a display device and/or a touch-screen display. The user may operate the percutaneous heart pump system by interacting with the user interface 312 to select, e.g., desired flow rates and other treatment parameters. The user may also monitor properties of the procedure on the user interface 312.

FIG. 3B is a three-dimensional perspective view of the interface region 303 of the console 301 shown in FIG. 3A. The interface region 303 can include the aperture 304 configured to receive the distal portion of the interface member 303. The aperture 304 may include a generally circular cavity shaped and sized to receive a portion of the interface member 300. A bubble detector 308 (e.g., an optical sensor in some embodiments) can be positioned at a back wall of the aperture 304. The bubble detector 308 may include a recess portion defined by two walls sized and shaped to receive a segment of tubing. When fluid flows through the tubing (see, e.g., bubble detector tube segment 326 in FIG. 4), the bubble detector 308 may monitor the fluid to determine whether or not the fluid includes unwanted matter, e.g., bubbles of air or other gas. In some embodiments, the bubble detector 308 may measure the amount (number or volume) of bubbles in the fluid passing though the tube segment. It should be appreciated that it can be important to detect bubbles in the treatment fluid to avoid inducing embolisms in the patient. The bubble detector 308 may electrically communicate with the controller in the console 301 and can indicate the amount of bubbles in the treatment fluid. The console 301, in turn, can alert the user if there are bubbles in the treatment fluid.

The interface region 303 can also include one or more pumps, e.g., peristaltic pumps in some embodiments. The peristaltic pumps can be used to pump fluid into or out of the catheter assembly 100A to deliver medical fluids and to remove waste fluids, respectively. Such pumps may employ one or more rollers 306 to control delivery of a fluid within a respective tube (see, e.g., pump tube segments 324a, 324b of FIG. 4). For example, the one or more pump rollers 306 can be housed within the console 301. As shown, two pump rollers 306 are mounted about their rotational axes (e.g., the Y-direction illustrated in FIG. 3B) at the back wall of the aperture 304. The pump rollers 306 can be rotated by a peristaltic pump motor within the console (not shown in FIGS. 3A-3B). As explained in more detail herein with respect to FIG. 4 below, the rollers 306 can engage pump tube segments 324a, 324b to pump fluid into or out of the catheter assembly 100A. The pump rollers 306 may be configured to be received within occlusion bed regions of the interface member 300 (see, e.g., occlusion beds 322a and 322b of FIG. 4) to pump fluid through the catheter assembly 100A.

An electrical interconnect 307 can also be provided in the back wall of the aperture 304. The electrical interconnect 307 can be configured to provide power to the motor assembly and/or electrical signals or instructions to control the operation of the motor assembly. The electrical interconnect 307 can also be configured to receive electrical signals indicative of sensor readings for monitoring pressure, flow rates, and/or temperature of one or more components in the catheter assembly 100A. A recessed channel 309 can extend from the bottom of the aperture 304 along the side to the lower edge of the console 301. The recessed channel 309 can be shaped and sized to receive one or more of the conduits 302 (e.g., electrical and/or fluid conduits) extending between the interface member 300 and the motor assembly. In one embodiment, all of the conduits 302 can be received within the channel 309 providing a flush side surface when the interface member 300 is disposed in the interface aperture 304.

In addition, it can be important to ensure that the interface member 300 is controllably secured within the console 301 such that it is engaged and disengaged only when the user desires to engage or disengage the interface member 300 from the console 301. For example, as explained in more detail herein relative to FIGS. 5A-5C, the interface region 303 can include a groove 313 sized and shaped to receive a locking mechanism (e.g., a tab or flange projecting in the X direction) on the interface member 300. In one embodiment, a disengaging member 305 includes a spring-loaded release mechanism 310 provided above the aperture 304 and a pin 311 that can be inserted into a hole in the interface member 300 (see, e.g., FIGS. 5A-5C and the accompanying disclosure below). As explained below with respect to FIGS. 5A-5C, the pin 311 can assist in releasing the interface member 300 relative to the console 301. The spring-loaded release mechanism 310 can be pressed to release the pin 311 and unlock the interface member 300 from the console 301. As explained herein, the spring-loaded release mechanism 310 can therefore act as a further safety mechanism to ensure that the cassette is not accidentally disengaged by the user.

Removable Interface Member

Figure 4:
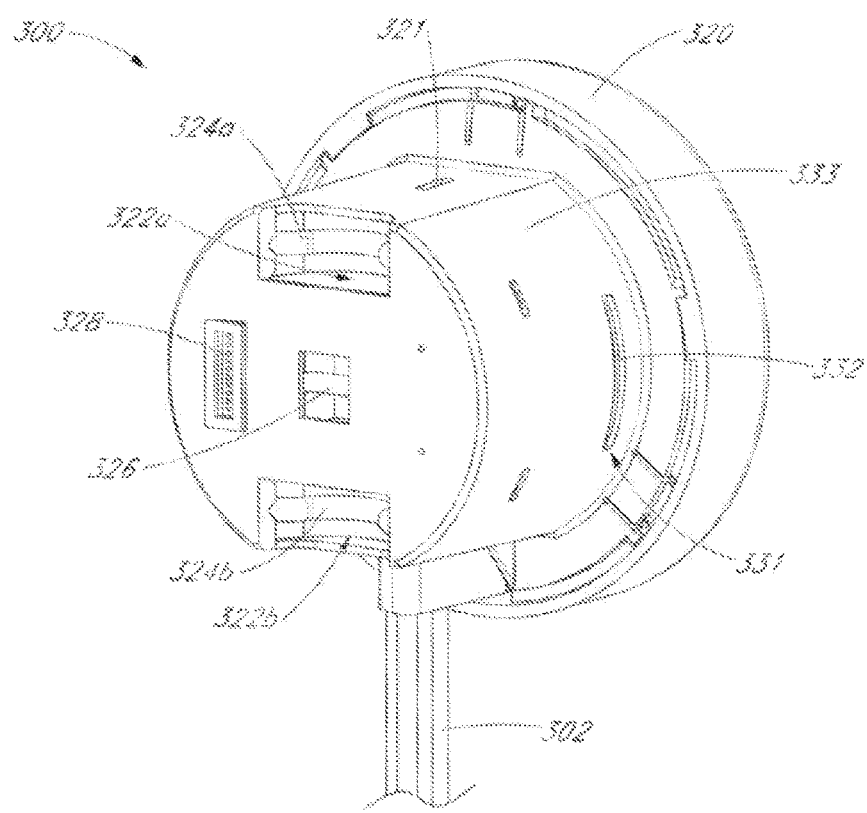
FIG. 4 is a three-dimensional perspective view of an interface member, according to one embodiment.

FIG. 4 is a three-dimensional perspective view of the interface member 300, according to one embodiment. The interface member 300 can comprise a body that is shaped and sized to fit into the interface region 303 of the console 301. As shown in FIG. 4, the interface member 300 can have a substantially circular profile, and is sometimes referred to as a puck. In some embodiments, the interface member 300 can include an outer body 333 operably coupled to a manual interface 320, sometimes referred to as a cap. The manual interface 320 is generally palm-sized so that a user can receive it in their hand and operate it comfortably, e.g., with finger pressure on the outer rim of the cap. One or more occlusion beds can be formed or provided at the interface between the interface member 300 and the console 301, e.g., in or on the interface member 300. For example, first and second occlusion beds 322a and 322b may be formed in the interface member 300. As shown in FIG. 4, for example, the occlusion beds 322a, 322b, can include arcuate recessed regions formed in the interface member 300.

The interface member 300 can further include first and second pump tube segments 324a, 324b positioned along the occlusion beds 322a, 322b formed in the interface member 300. When the interface member 300 is inserted into the console 301, the pump rollers 306 can engage with the interface member 300 and compress the tube segment(s) 324a, 324b against the occlusion bed(s) 322a, 322b, respectively. As the pump motor(s) in the console 301 rotate the rollers 306, fluid flows into uncompressed portions of the tube segment(s) 324a, 324b and continues flowing throughout the catheter assembly 100A. For example, by compressing the tube segments 324a, 324b, the fluid may be pumped into or out of the catheter assembly 100A by way of the conduits 302 extending from the interface member 300 to the motor assembly and distally beyond the motor assembly.

Because the tolerances for the peristaltic pump can be rather tight, the body of the interface member 300 (e.g., the outer body 333 and/or an inner body, such as inner body 339 illustrated in FIGS. 5B-5C) can be formed with precise tolerances (e.g., molded from a unitary structure in some implementations) such that when the interface member 300 is inserted into the console 301, the pump rollers 306 precisely and automatically engage with the tube segments 324a, 324b and occlusion beds 322a, 322b to reliably occlude the tube segments 324a, 324b and pump fluids through the catheter assembly 100A. Thus, when the interface member 300 is inserted sufficiently far into the interface region 303, the pump in the console 301 can automatically engage the interface member 300.

For example, the gap between the rollers 306 and the occlusion beds 322a, 322b can be less than about two wall thicknesses of the tube segments 324a, 324b in some arrangements, such that the tubes 324a, 324b can be effectively occluded. Due to the precise tolerances of the interface member 300, the pump can be engaged by simply inserting the interface member 300 into the console 301. There is no need to separately activate the pump in some embodiments. The dimensions of the interface member 300 may be selected such that the occlusion bed(s) 322a, 322b automatically engages the respective pump rollers 306 upon insertion of the interface member 300 into the console 301.

The above configuration provides several advantages. As one of skill in the art will appreciate from the description herein, the interface member 300 and interface region 303 provide an easy-to-use, quick connection of the tubing segments to one or more respective rollers 306. Moreover, the components can be manufactured easily and cost-effectively because only certain components require tight tolerances and the interface of member 300 to region 303 is essentially self-aligning. The interface also eliminates any need to engage the pump through a second mechanism or operator step, streamlining operation of the heart pump and simplifying the engagement of the catheter assembly 100A to the console 301. Also, in implementations where the console 301 is mounted on an IV pole with rollers, or another type of lightweight cart, for example, the simplified engagement mechanisms disclosed herein can be advantageous because there is only a minimal applied force against the pole, which prevents the pole from rolling or tipping when the pump is engaged.

The pump tube segments 324a, 324b can be mounted on the interface body 300 near or in the respective occlusion beds 322a, 322b. As illustrated, the first and second pump tube segments 324a, 324b can be configured to engage with the pump rollers 306 in the console 301, as explained above. The first and second pump tube segments 324a, 324b can have an arcuate shape (which may be pre-formed in various arrangements) that generally conforms to the curved shape of each respective occlusion bed 322a, 322b. The pump rollers 306 within the console 301 can thereby be positioned within the occlusion beds 322a, 322b to compress the tube segments 324a, 324b against the wall of the occlusion beds 322a, 322b. In addition, a bubble detector tube segment 326 can also be mounted in or on the interface member 300 and can be configured to engage with or be positioned adjacent to the bubble detector 308 illustrated in FIG. 3B. The bubble detector tube segment 326 can be any suitable shape. As illustrated, the bubble detector tube segment can be substantially straight and can be sized and shaped to be received by the bubble detector 308 within the console 301. As explained above with respect to FIGS. 3A-3B, the bubble detector 308 (which may be an optical sensor) can be used to detect air bubbles in the treatment or lubricating fluid being supplied to the patient.

The tube segments can be fluidly connected to the remainder of the catheter assembly 100A, including, e.g., one or more lumens of the catheter body, by way of the conduits 302. In operation, therefore, the removable interface member 300 may allow fluid to be pumped into and out of the patient within a controlled system, e.g., such that the fluids within the catheter assembly 100A can be pumped while maintaining a sterile environment for the fluids. Depending on the implementation, the volume of medical solution into the catheter body can be equal to, or can exceed by a minimum amount, the volume of medical solution out of the catheter body to assure that blood does not enter a blood-free portion of the heart pump.

In addition, one or more electrical contacts 328 can be provided in the interface member 300. The electrical contacts 328 can be any suitable electrical interface configured to transmit electrical signals between the console 301 and the catheter assembly 100A (e.g., the motor assembly and/or any suitable sensors). For example, the electrical contacts 328 can be configured to electrically couple to the electrical interconnect 307 disposed in the console 301. Electrical control signals and/or power may be transmitted between the console 301 and the catheter assembly 100A by way of the electrical connection between the electrical contacts 328 and the electrical interconnect 307. Advantageously, the electrical connection between the electrical contacts 328 and the electrical interconnect 307 may be formed or completed when the interface member 300 is inserted into the interface region 303 of the console 301. For example, in some embodiments, the electrical connection between the electrical contacts 328 and the electrical interconnect 307 may be formed substantially simultaneously with the fluid connection (e.g., the engagement of the pump) when the interface member 300 is inserted into the interface region 303. In some aspects, for example, the electrical connection can be formed by inserting electrical pins from the electrical contacts 328 into corresponding holes of the electrical interconnect 307 of the console 301, or vice versa.

Further, as shown in FIG. 4, the manual interface 320 can be mechanically coupled to a proximal portion of the outer body 333 and may be configured to rotate relative to the outer body 333 in a constrained manner, as explained below relative to FIGS. 5A-5C. For example, the outer body 333 can include one or more locking apertures 331 configured to receive locking tabs 332 that are configured to lock the manual interface 320 relative to the console 301. Moreover, as explained below relative to FIGS. 5A-5C, the outer body 333 may include a pin hole 321 sized and shaped to receive the pin 311 illustrated in FIG. 3B to releasably couple the removable interface member 300 relative to the console 301.

One will appreciate from the description herein that the configuration of the pump rollers, occlusion bed, and tubing can be modified depending on the application in accordance with the present inventions. For example, the configuration may be modified to provide easier access for service and repair. In various embodiments, the pump rollers may be disposed external to the console. In various embodiments, the pump rollers and occlusion bed may be both disposed within the cassette. In various embodiments, the console includes a mechanism to actuate the pump rollers in the cassette. In various embodiments, the rollers may be fixed. In various embodiments, the rollers may be configured to rotate, translate, or both. The rollers and/or the occlusion bed may be positioned on a base that is configured to move. In some embodiments, the console-cassette interface can include a positive pressure interface to pump fluid (e.g., saline) into the patient's vasculature and a negative pressure interface to pump fluid (e.g., waste fluid) out of the patient's vasculature.

Locking Mechanism

As discussed above, the interface member 300 advantageously can be fully engaged with the console 301 by simply inserting it into a correspondingly shaped aperture 304 in the housing of the console 301. When interface member 300 is brought into adjacency with a back wall of the interface region 303 of the console, e.g., when the interface member 300 is inserted into the aperture 304, the fluid handling and electrical connections are made, and the system 350 is operational. A locking mechanism in the interface member 300 can be provided for additional security, which can be particularly useful for patient transport and other more dynamic settings. For example, it is desirable to ensure that the catheter assembly 100A is secured to the console 301 during the entire procedure to ensure that the procedure is not disrupted due to accidental disengagement of the interface member 300 from the console 301.

In one embodiment, the locking mechanism can be disposed between the console 301 and the interface member 300 and can be configured to be engaged by a minimal movement of an actuator. For example, the manual interface 320 can be provided to cause engagement of a locking device by a small rotational turn of the manual interface 320 relative to the console 301.

Figure 5A:
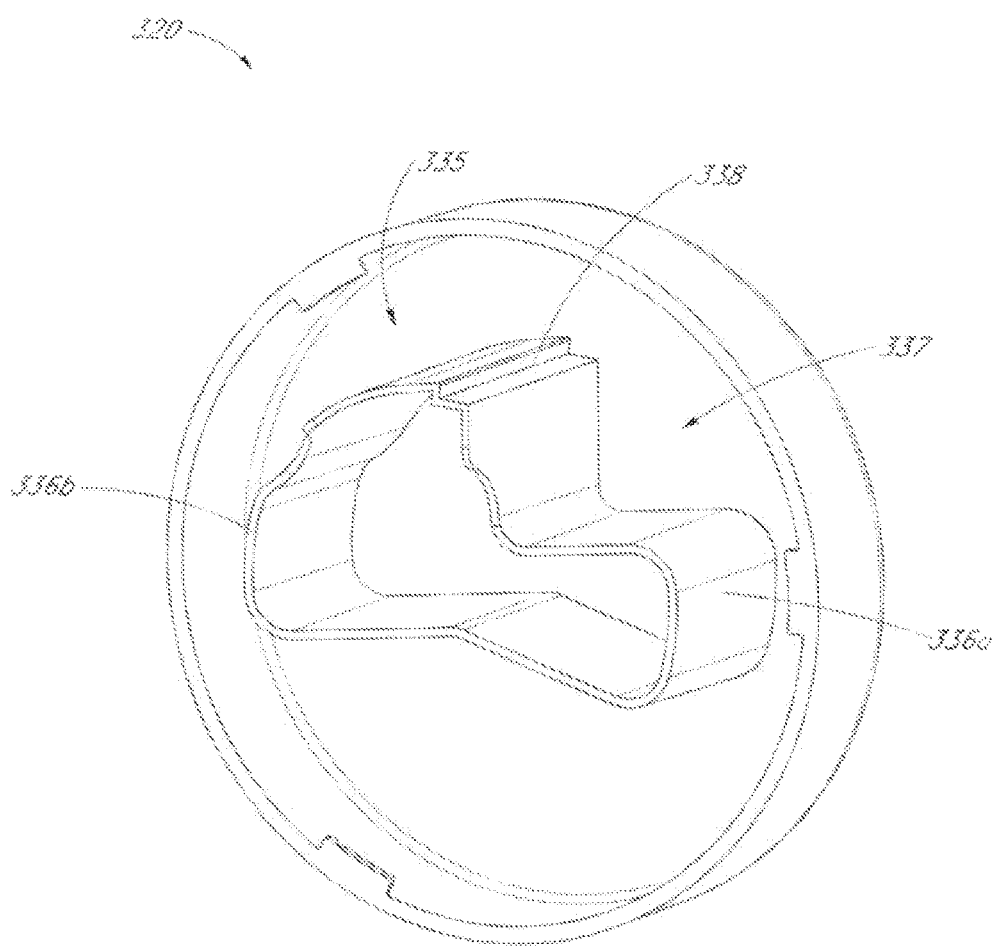
FIG. 5A is a three-dimensional perspective view of a cap.

FIG. 5A is a three-dimensional perspective view of the manual interface 320. As shown in FIG. 5A, the manual interface 320 can include or be coupled with an internal cam 335. The cam 335 can include one or more protruding lobes, such as lobes 336a and 336b. Further, the cam 335 can include a recessed region 337 recessed inwardly relative to the lobes 336a, 336b. The cam 335 can also include a stepped region 338 which can enable the interface member 300 to be locked and unlocked relative to the console 301, as explained herein.

FIG. 5B is a three-dimensional perspective view of an interface member 300A in an unlocked configuration, and FIG. 5C is a three-dimensional perspective view of an interface member 300B in a locked configuration. It should be appreciated that the interface members 300A, 300B of FIGS. 5B and 5C are illustrated without the outer body 333, which has been hidden in FIGS. 5B and 5C for purposes of illustration. Unless otherwise noted, the components of FIGS. 5B and 5C are the same as or similar to the components illustrated with respect to FIG. 4. As shown in FIGS. 5B and 5C, the interface members 300A, 300B can include an inner body 339 that can be disposed within the outer body 333 shown in FIG. 4. The occlusion beds 322a, 322b can be formed in the inner body 339 of the interface member 300A, 300B, as shown in FIGS. 5B-5C; however, in other arrangements, the occlusion beds 322a, 322b may be formed in the outer body 333 or other portions of the interface member 300A, 300B. In addition, as shown in FIGS. 5A and 5B, an electrical component 340 can be disposed in a recess or other portion of the inner body 339. Additional details regarding the electrical component 340 are explained below with respect to FIGS. 6A-6B.

The inner body 339 of the interface member 300A, 300B can further include a protrusion 330 that includes the tab 332 at a distal portion of the protrusion 330. When the interface member 300A is in the unlocked configuration, the protrusion 330 can be disposed in or near the recess 337 of the cam 335 in the manual interface 320. The cam 335 may therefore not contact or apply a force against the protrusion 330 when the interface member 300A is in the unlocked configuration, as shown in FIG. 5B.

However, once the interface member 300 is inserted into the console 301, the interface member 300 can be locked into place by rotating the manual interface 320 relative to the inner body 339 and the console 301, e.g., rotated in the A-direction illustrated in FIG. 5B. When the manual interface 320 is rotated, the internal cam 335 is also rotated within the interface member 300A, 300B. Once the cam is rotated, the lobes 336a, 336b of the cam 335 can engage with the one or more protrusions 330 of the inner body 339 and can push the protrusions 330 outwardly relative to the inner body 339. In one embodiment, the tabs 332 may extend outwardly through the locking apertures 331 formed on the outer body 333. When the tab(s) 332 are pushed through the locking aperture(s) 331, the tabs 332 project laterally outward from the outer body 333. In this position, in some embodiments, each of the tabs 332 can lock into the groove(s) 313 in the console 301 (see FIG. 3B) to secure the interface member 300B to the console 301. Thus, in the unlocked position, the tab 332 can be substantially flush with the outer surface of the interface member 300A, and in the locked position, the tab 332 can extend through the locking aperture 331 and lock into the grooves 313 in the console 301.

In some embodiments, the protrusion 330 can be a cantilevered protrusion from the inner body 339. As mentioned above, it can be important to maintain tight tolerances between the occlusion beds 322a, 322b, which is also formed in the interface member, and the pump rollers 306 when the interface member 300 engages with the console 301. Because the occlusion beds 322a, 322b may be formed in the same body as the cantilevered protrusions 330, conventional manufacturing processes, such as molding processes, can be used to manufacture the interface member 300 (e.g., the outer body 333 and/or the inner body 339) according to precise dimensions. Thus, the protrusion(s) 330, tab(s) 332 and the occlusion bed(s) 322a, 322b can be made within tight dimensional tolerances, and the tab(s) 332 and/or protrusion(s) 330 can be positioned relative to the occlusion bed(s) 322a, 322b with very high precision such that when the interface member 300 is engaged with the console 301, the tube segments 324a, 324b are optimally occluded. Moreover, because the interface member 300 can be locked by rotating the manual interface 320 on the interface member 300, only minimal forces are applied to the console 301. This enhances the advantages of minimizing disruption of a mobile cart or IV pole to which the system may be coupled.

Disengagement Mechanism

It can also be important to provide a disengagement mechanism configured to decouple the interface member 300 from the console 301. With reference to FIGS. 3B, 4, 5B, and 5C, the disengaging member 305 of the console 301 can be configured to disengage and unlock the interface member 300 from the console 301. For example, the pin 311 may be spring-loaded such that when the interface member 300A is in the unlocked configuration, the pin 311 extends through the pin hole 321 of the outer body 333 but only contacts a side surface of one of the lobes 336b of the cam 335. Thus, in the unlocked configuration of the interface member 300A, the pin 311 may simply slide along the cam surface, permitting rotation of the manual interface 320 relative to the pin 311 and the console 301.

As shown in FIGS. 3B and 5C, however, when the interface member 300B is rotated into a locked configuration, the pin 311 can engage with the stepped region 338 of the internal cam 335, e.g., the spring-biased pin 311 can extend into the stepped region 338 or shoulder of the cam 335. By engaging the stepped region 338, the pin 311 prevents the cam 335 from rotating from the locked configuration to the unlocked configuration. A user can disengage the cassette by pressing the spring-loaded release mechanism 310 to release the spring and remove the pin 311 from the stepped region 338. The pin 311 can thereby be disengaged from the stepped region 338, and the internal cam 335 can rotate back into the unlocked position. When the cam 335 is moved back into the unlocked position, the tab 332 can be withdrawn from the groove 313 in the console 301 to unlock the interface member 300.

Electrical Interconnections, Components, and Cables

Figure 6A:
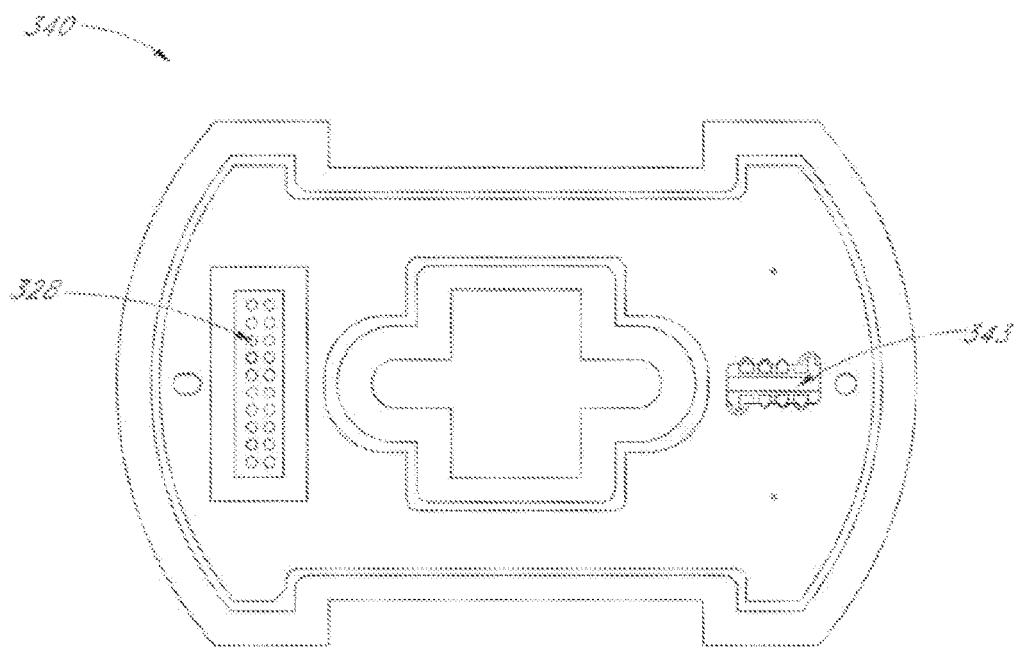
FIG. 6A is a three-dimensional perspective view of a first side of an electrical component, according to one embodiment.
Figure 6B:
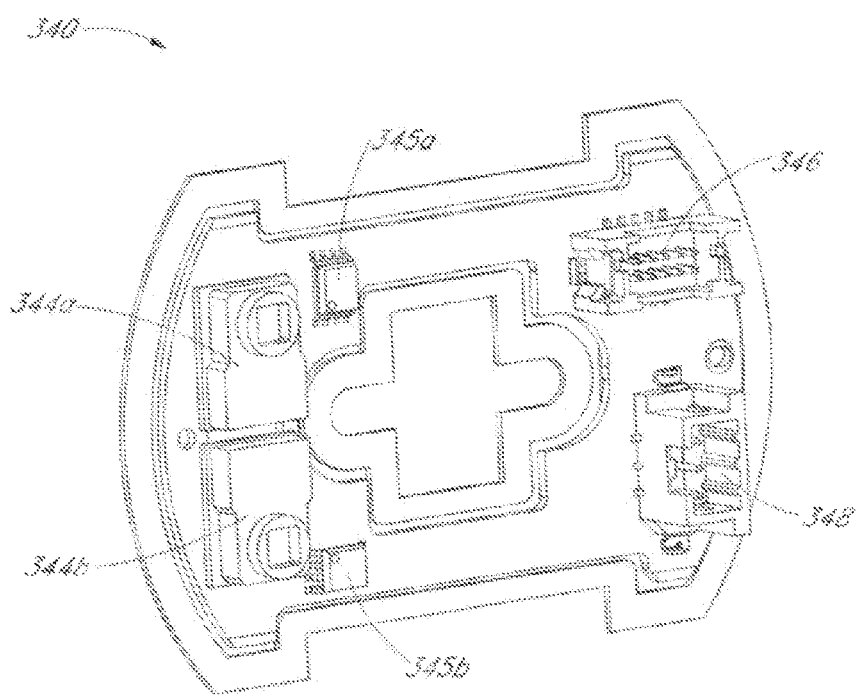
FIG. 6B is a three-dimensional perspective view of a second, opposite side of the electrical component of FIG. 6A.

FIG. 6A is a three-dimensional perspective view of a first side of the electrical component 340 illustrated in FIG. 4. FIG. 6B is a three-dimensional perspective view of a second, opposite side of the electrical component 340 of FIG. 6A. As shown in FIGS. 5B-5C, the electrical component 340 may be disposed in a recess of the interface member 300. The electrical component 340 can be any suitable electrical or electronic component, including, e.g., a printed circuit board (PCB) configured to provide an electrical interface between various components in the catheter assembly 100A and the console 301. As explained herein, the electrical component 340 can form an electrical interface between the interface member 300 and the console 301 to provide electrical communication between the console 301 and the catheter assembly 100A (such as the motor assembly and/or various sensors).

For example, the electrical component 340 of the interface member 300 can include the one or more electrical contacts 328 configured to mate with the corresponding electrical interconnect 307 in the console 301. The electrical contacts 328 and/or the electrical interconnect 307 can be, for example, nine-pin electrical interconnects, although any suitable interconnect can be used. The motor assembly that drives the operative device (e.g., impeller) of the catheter pump can be electrically connected to the interface member 300 by way of one or more electrical cables, e.g., the conduits 302. In turn, the console 301 can be coupled to a power source, which can drive the catheter pump motor assembly by way of the interface member's contacts 328 and the electrical conduits 302 connecting the interface member 300 to the motor assembly. The electrical component 340 can also include communications interconnects configured to relay electrical signals between the console 301 and the catheter pump motor assembly or other portions of the catheter assembly 100A. For example, a controller within the console 301 (or interface member) can send instructions to the catheter pump motor assembly via the electrical component 340 between the console 301 and the interface member 300. In some embodiments, the electrical component 340 can include interconnects for sensors (such as pressure or temperature sensors) within the catheter assembly 100A, including sensors at the operative device. The sensors may be used to measure a characteristic of the fluid in one or more of the tubes (e.g., saline pressure). The sensors may be used to measure an operational parameter of the system (e.g., ventricular or aortic pressure). The sensors may be provided as part of an adjunctive therapy.

The electrical component 340 within the interface member 300 can be used to electrically couple the cable (and the motor assembly, sensors, etc.) with the corresponding interconnects 307 in the console 301. For example, one or more internal connectors 346 and 348 on the second side of the electrical component 340 may provide electrical communication between the contacts 328 (configured to couple to the interconnects 307 of the console 301) and the catheter assembly 100. For example, electrical cables (e.g., the conduits 302) can couple to a first internal connector 346 and a second internal connector 348. The internal connectors 346, 348 may electrically communicate with the contacts 328 on the first side of the electrical component 340, which in turn communicate with the interconnects 307 of the console 301.

In various embodiments, the electrical component 340 is fluidly sealed to prevent the internal electronics from getting wet. This may be advantageous in wet and/or sterile environments. This may also advantageously protect the electronics in the event one of the fluid tubes leaks or bursts, which is a potential risk in high pressure applications.

In addition, the electrical component 340 (e.g., PCB) can include various electrical or electronic components mounted thereon. As shown in FIG. 6B, for example, two pressure sensors 344a, 344b can be mounted on the electrical component 340 to detect the pressure in the pump tube segments 324a, 324b. The pressure sensors 344a, 344b may be used to monitor the flow of fluids in the tube segments 324a, 324b to confirm proper operation of the heart pump, for example, confirming a proper balance of medical solution into the catheter body and waste out of the catheter body. Various other components, such as a processor, memory, or an Application-Specific Integrated Circuit (ASIC), can be provided on the circuit board. For example, respective pressure sensor ASICs 345a, 345b can be coupled to the pressure sensors 344a, 344b to process the signals detected by the pressure sensors 344a, 344b. The processed signals may be transmitted from the ASICs 345a, 345b to the console 301 by way of internal traces (not shown) in the PCB and the contacts 328.

Priming and Infusate System and Apparatus

Figure 7:
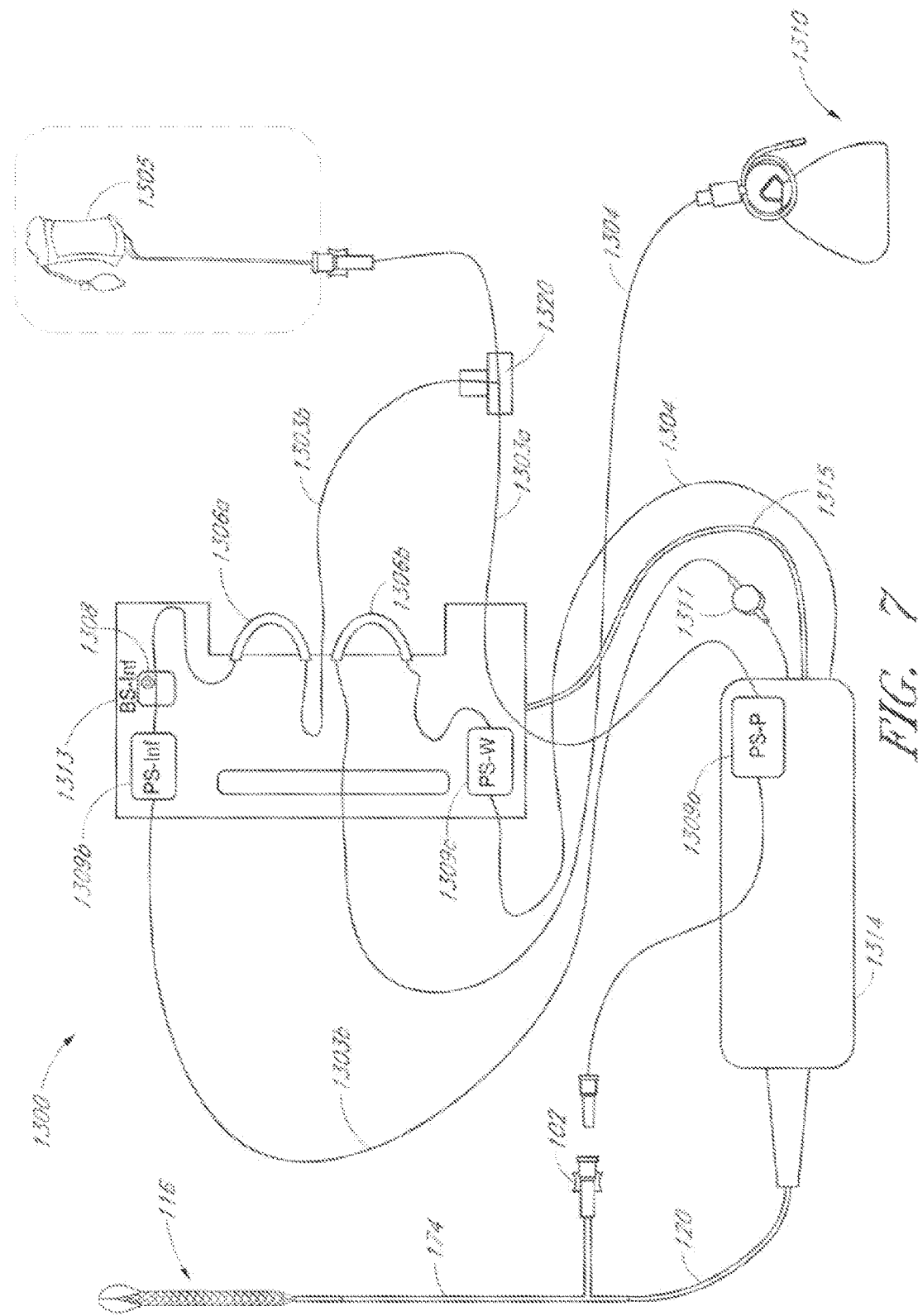
FIG. 7 is a schematic diagram of an infusate system, according to one embodiment.

One embodiment of an infusate system 1300 is illustrated in FIG. 7. Various components described herein can be understood in more detail by referencing the patent applications incorporated by reference herein. The infusate system 1300 can be configured to supply treatment and/or lubricating fluids to the operative device of the catheter assembly (e.g., an impeller assembly 116), and to remove waste fluid from the assembly. Furthermore, as explained herein, an elongate body 174 can be slidably disposed over a catheter body 120, such that there may be gaps or channels between the outer surface of the catheter body 120 and the inner surface of the elongate body 174. Such gaps or channels can contain air pockets harmful to the patient during a medical procedure. In addition, the lumen or lumens extending within the catheter body 120 also can contain air pockets harmful to the patient. Thus, it is desirable to expel air from both the lumens within catheter body 120 and the gaps or channels disposed between the elongate body 174 and the catheter body 120 before conducting a treatment procedure.

The system 1300 of FIG. 7 may be configured to supply fluid to the catheter assembly during treatment, to remove waste fluid during treatment, and/or to expel air from the elongate body 174, e.g., between the inner surface of the elongate body 174 and the outer surface of the catheter body 120 before treatment. In this embodiment, an interface member 1313 (similar to or the same as the interface member 300 described herein, in some aspects) may be provided to connect various components of the catheter assembly, as discussed herein. An outer sheath tubing 1303a can extend from a fluid reservoir 1305 to a luer 102 configured to be coupled to an infusate device. As shown in FIG. 7, the outer sheath tubing 1303a can be configured to deliver fluid to the outer sheath, e.g., the space between the elongate body 174 and the catheter body 120. The fluid reservoir 1305 may optionally include a pressure cuff to urge fluid through the outer sheath tubing 1303a. Pressure cuffs may be particularly useful in fluid delivery embodiments using gravity-induced fluid flow. The luer 102 can be configured to deliver infusate or other priming fluid to the elongate body 174 to expel air from the elongate body 174 as described herein in order to "prime" the system 1300. In addition, a pressure sensor 1309a, which may be disposed on a motor housing 1314, can be coupled to the outer sheath tubing 1303a to measure the pressure of the infusate or priming fluid flowing through the outer sheath tubing 1303a and into the luer 102. The motor housing 1314 illustrated in FIG. 7 may be the same as or similar to the motor assembly described above with reference to FIG. 2, for example, when the drive assembly 103 is coupled to the driven assembly 101.

As illustrated in the embodiment of FIG. 7, inner catheter tubing 1303b can extend between the motor housing 1314 and the fluid reservoir 1305, by way of a T-junction 1320. The inner catheter tubing 1303b can be configured to deliver fluid to the lumen or lumens within catheter body 120 during treatment and/or to expel air from the catheter 120 and prime the system 1300. A pumping mechanism 1306a, such as a roller pump for example, can be provided along inner catheter tubing 1303b to assist in pumping the infusate or priming fluid through the system 1300. As explained herein, the roller pump can be a peristaltic pump in some arrangements. In addition, an air detector 1308 can be coupled to the inner catheter tubing 1303b and can be configured to detect any air or bubbles introduced into the system 1300. In some embodiments, a pressure sensor 1309b can couple to inner catheter tubing 1303b to detect the pressure of the fluid within the tubing. Additionally, a filter 1311 can be employed to remove debris and other undesirable particles from the infusate or priming fluid before the catheter body 120 is infused or primed with liquid. In some embodiments, the air detector 1308, the pressure sensor 1309b, and the pumping mechanism 1306a can be coupled to the interface member 1313 described above (such as the interface member 300). One or more electrical lines 1315 can connect the motor housing 1314 with the cassette 1313. The electrical lines 1315 can provide electrical signals for energizing a motor or for powering the sensor 1309a or for other components. To expel air from the catheter body 120, infusate or priming fluid can be introduced at the proximal end of the catheter assembly. The fluid can be driven distally to drive air out of the catheter body 120 to prime the system.

In some aspects, a waste fluid line 1304 can fluidly connect the catheter body 120 with a waste reservoir 1310. A pressure sensor 1309c, which may be disposed on or coupled to the interface member 1313, can measure the pressure of the fluid within the waste fluid line 1304. A pumping mechanism 1306b, such as a roller pump, for example, can be coupled to the interface member 1313 and can pump the waste fluid through the waste fluid line 1304 to the waste reservoir 1310.

Figure 8:
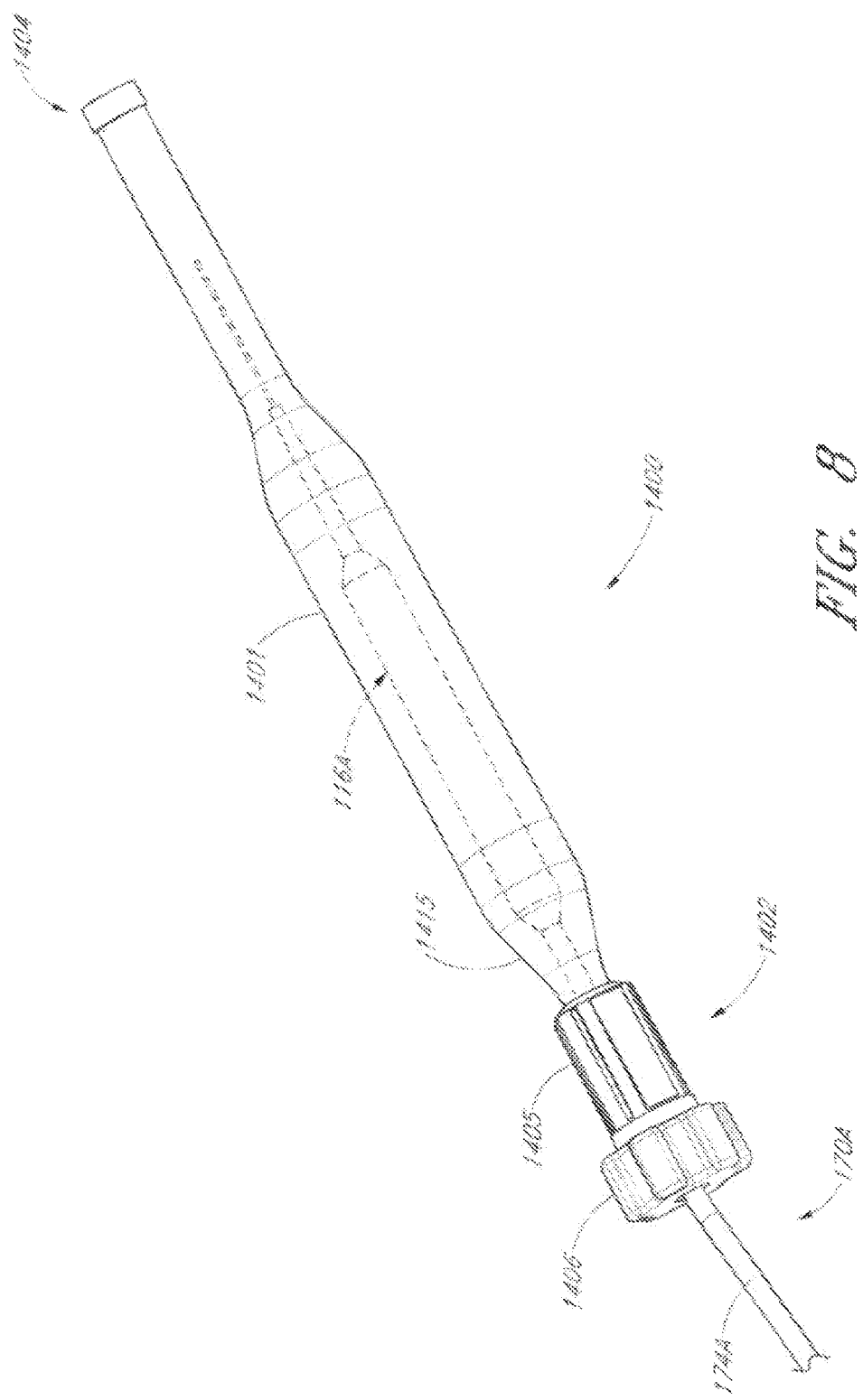
FIG. 8 is an enlarged view of a priming apparatus shown in FIG. 2.

FIG. 8 is an enlarged view of the priming apparatus 1400 shown in FIG. 2. As explained above, the priming apparatus 1400 may be disposed over the impeller assembly 116A near the distal end 170A of the elongate body 174A. The priming apparatus 1400 can be used in connection with a procedure to expel air from the impeller assembly 116A, e.g., any air that is trapped within the housing or that remains within the elongate body 174A near the distal end 170A. For example, the priming procedure may be performed before the pump is inserted into the patient's vascular system, so that air bubbles are not allowed to enter and/or injure the patient. The priming apparatus 1400 can include a primer housing 1401 configured to be disposed around both the elongate body 174A and the impeller assembly 116A. A sealing cap 1406 can be applied to the proximal end 1402 of the primer housing 1401 to substantially seal the priming apparatus 1400 for priming, i.e., so that air does not proximally enter the elongate body 174A and also so that priming fluid does not flow out of the proximal end of the housing 1401. The sealing cap 1406 can couple to the primer housing 1401 in any way known to a skilled artisan. However, in some embodiments, the sealing cap 1406 is threaded onto the primer housing by way of a threaded connector 1405 located at the proximal end 1402 of the primer housing 1401. The sealing cap 1406 can include a sealing recess disposed at the distal end of the sealing cap 1406. The sealing recess can be configured to allow the elongate body 174A to pass through the sealing cap 1406.

The priming operation can proceed by introducing fluid into the sealed priming apparatus 1400 to expel air from the impeller assembly 116A and the elongate body 174A. Fluid can be introduced into the priming apparatus 1400 in a variety of ways. For example, fluid can be introduced distally through the elongate body 174A into the priming apparatus 1400. In other embodiments, an inlet, such as a luer, can optionally be formed on a side of the primer housing 1401 to allow for introduction of fluid into the priming apparatus 1400.

A gas permeable membrane can be disposed on a distal end 1404 of the primer housing 1401. The gas permeable membrane can permit air to escape from the primer housing 1401 during priming.

The priming apparatus 1400 also can advantageously be configured to collapse an expandable portion of the catheter assembly 100A. The primer housing 1401 can include a funnel 1415 where the inner diameter of the housing decreases from distal to proximal. The funnel may be gently curved such that relative proximal movement of the impeller housing causes the impeller housing to be collapsed by the funnel 1415. During or after the impeller housing has been fully collapsed, the distal end 170A of the elongate body 174A can be moved distally relative to the collapsed housing. After the impeller housing is fully collapsed and retracted into the elongate body 174A of the sheath assembly, the catheter assembly 100A can be removed from the priming housing 1400 before a percutaneous heart procedure is performed, e.g., before the pump is activated to pump blood. The embodiments disclosed herein may be implemented such that the total time for infusing the system is minimized or reduced. For example, in some implementations, the time to fully infuse the system can be about six minutes or less. In other implementations, the infusate time can be less than 5 minutes, less than 4 minutes, or less than 3 minutes. In yet other implementations, the total time to infuse the system can be about 45 seconds or less. It should be appreciated that lower infusate times can be advantageous for use with cardiovascular patients.

Preparing a Percutaneous Heart Pump for Insertion into the Vasculature

As discussed herein and in the incorporated patent applications, in various embodiments the heart pump is inserted in a less invasive manner, e.g., using techniques that can be employed in a catheter lab.

Prior to insertion of the catheter assembly 100A of the heart pump, various techniques can be used to prepare the system for insertion. For example, as discussed in connection with FIG. 8, the catheter assembly 100A can be primed to remove gas that could be contained therein prior to any method being performed on the patient. This priming technique can be performed by placing a distal portion of the catheter assembly 100A in a priming vessel, such as the apparatus 1400. Thereafter, a media is delivered into the catheter assembly 100A under pressure to displace any potentially harmful matter, e.g., air or other gas, out of the catheter assembly 100A. In one technique, the apparatus 1400 is filled with a biocompatible liquid such as saline. Thereafter, a biocompatible liquid such as saline is caused to flow distally through the catheter assembly 100 to displace air in any of the cavities formed therein, as discussed above. A pressure or flow rate for priming can be provided that is suitable for priming, e.g., a pressure or flow rate that is lower than the operational pressure or flow rate.

In one technique, the biocompatible liquid is pushed under positive pressure from the proximal end through the catheter assembly 100A until all gas is removed from voids therein. One technique for confirming that all gas has been removed is to observe the back-pressure or the current draw of the pump. As discussed above, the priming apparatus 1400 can be configured to permit gas to escape while preventing saline or other biocompatible liquid from escaping. As such, the back-pressure or current draw to maintain a pre-selected flow will change dramatically once all gas has been evacuated.

In another technique, the priming apparatus 1400 can include a source of negative pressure for drawing a biocompatible liquid into the proximal end of the catheter assembly 100A. Applying a negative pressure to the priming apparatus 1400 can have the advantage of permitting the catheter assembly 100A to be primed separate from the pumps that are used during operation of the heart pump. As a result, the priming can be done in parallel with other medical procedures on the patient by an operator that is not directly working on the patient.

In another approach, a positive pressure pump separate from the pump that operates the heart pump can be used to prime under positive pressure applied to the proximal end. Various priming methods may also be expedited by providing a separate inlet for faster filling of the enclosed volume of the priming apparatus 1400.

Collapsing an Expandable Housing of a Fully Primed Catheter Assembly

A further aspect of certain methods of preparing the catheter assembly 100A for insertion into a patient can involve collapsing the impeller housing 116A. The collapsed state of the impeller housing 116A reduces the size, e.g., the crossing profile, of the distal end of the system. This enables a patient to have right, left or right and left side support through a small vessel that is close to the surface of the skin, e.g., using catheter lab-type procedures. As discussed above, in one technique the priming apparatus 1400 has a funnel configuration that has a large diameter at a distal end and a smaller diameter at a proximal end. The funnel gently transitions from the large to the small diameter. The small diameter is close to the collapsed size of the impeller housing 116A and the large diameter is close to or larger than the expanded size of the impeller housing 116A. In one method, after the catheter assembly 100A has been primed, the impeller housing 116A can be collapsed by providing relative movement between the priming apparatus 1400 and the impeller housing 116A. For example, the priming housing 1400 can be held in a fixed position, e.g., by hand, and the catheter assembly 100A can be withdrawn until at least a portion of the impeller assembly 116A is disposed in the small diameter segment of the priming apparatus 1400. Thereafter, the elongate body 174A of the sheath assembly can be advanced over the collapsed impeller assembly 116A.

In another technique, the catheter assembly 100A is held still and the priming apparatus 1400 is slid distally over the impeller assembly 116A to cause the impeller assembly 116A to collapse. Thereafter, relative movement between the elongate body 174A and the impeller assembly 116A can position the distal end 170A of the elongate body 174A over the impeller assembly 116A after the catheter assembly 100A has been fully primed.

Control System

Various embodiments disclosed herein enable the control and management of the catheter pump system during, e.g., preparation of the system and operation of the system to pump blood through a patient. As explained above, conventional systems may provide the user or clinician with unclear guidance on how to proceed at various points during the procedure. For example, the instructions provided with the packaged system may ask the user to verify various system states visually or manually (e.g., instructing the clinician to verify that the cassette has been inserted correctly, that the pump is ready to be primed, that the pump is ready to be used to pump blood, to manually verify a desired pressure, etc.). The potential for unclear user instructions and guidance may cause the user to make mistakes that can be harmful to patient outcomes. Moreover, in conventional systems, it may take the user or clinician a considerable amount of time to prepare the system for use, which may unduly delay the treatment procedure. In addition, in other systems, the user may not understand the priming process described above, and/or may not be trained to recognize that the system is ready to be primed or the status of a priming procedure.

Beneficially, the embodiments disclosed herein can address these problems by providing a control system that receives sensor data and automatically controls the preparation and/or operation of the catheter pump system based on that sensor data. For example, in various embodiments, the control system can automatically control the priming processes disclosed herein. The control system can instruct the user how to insert the cassette into the console, and, in response, the control system can automatically determine whether or not the cassette has been inserted correctly. The control system may monitor additional sensor data as well, such as pressure sensor data and/or bubble sensor data, to determine that the cassette is correctly receiving (and/or sending) electronic data and/or fluid from (and/or to) the console. Once the control system determines that the cassette has been correctly inserted, and that the cassette is in mechanical, fluidic, and/or electrical communication with the console, the control system can instruct a motor to drive a pump to deliver fluid distally through the catheter assembly to drive gases from the catheter assembly.

Thus, the embodiments disclosed herein can advantageously manage the priming processes described herein, based at least on sensor data from one or more sensors. The mechanical arrangement of the cassette (e.g., interface member or puck) and console described above can enable automatic mechanical, fluid, and electrical connection between the cassette and console once the system detects proper insertion of the cassette into the console. Control of the priming and other preparatory processes can beneficially reduce user errors, reduce preparation and priming time, and improve controllability to avoid adverse events and improve treatment outcomes.

Further, the control system can automatically determine whether preparation and priming is complete, and can begin operation to pump blood based on sensor feedback and/or instructions provided by the user through a user interface. The control system can monitor the sensors to determine problems that may arise and can initiate an alarm to indicate any problems. For example, in some embodiments, the motor may draw excessive current that exceeds a predetermined threshold, which may indicate a problem with the impeller (such as a bind). The control system can recognize such an overcurrent condition and can initiate an alarm to alert the clinician. In some embodiments, the control system can automatically shut off the motor in the event of such an overcurrent condition. Moreover, the control system can control the supply of fluid to the patient and the removal of fluid (e.g., waste fluid) from the patient. The control system can collect and analyze sensor data representative of problems with fluid supply and/or waste withdrawal, such as clogged lines, etc. The system can initiate an alarm to the user based on these conditions. Thus, the embodiments disclosed herein can also enable automatic control of the operation of the catheter pump to pump blood.

Figure 9:
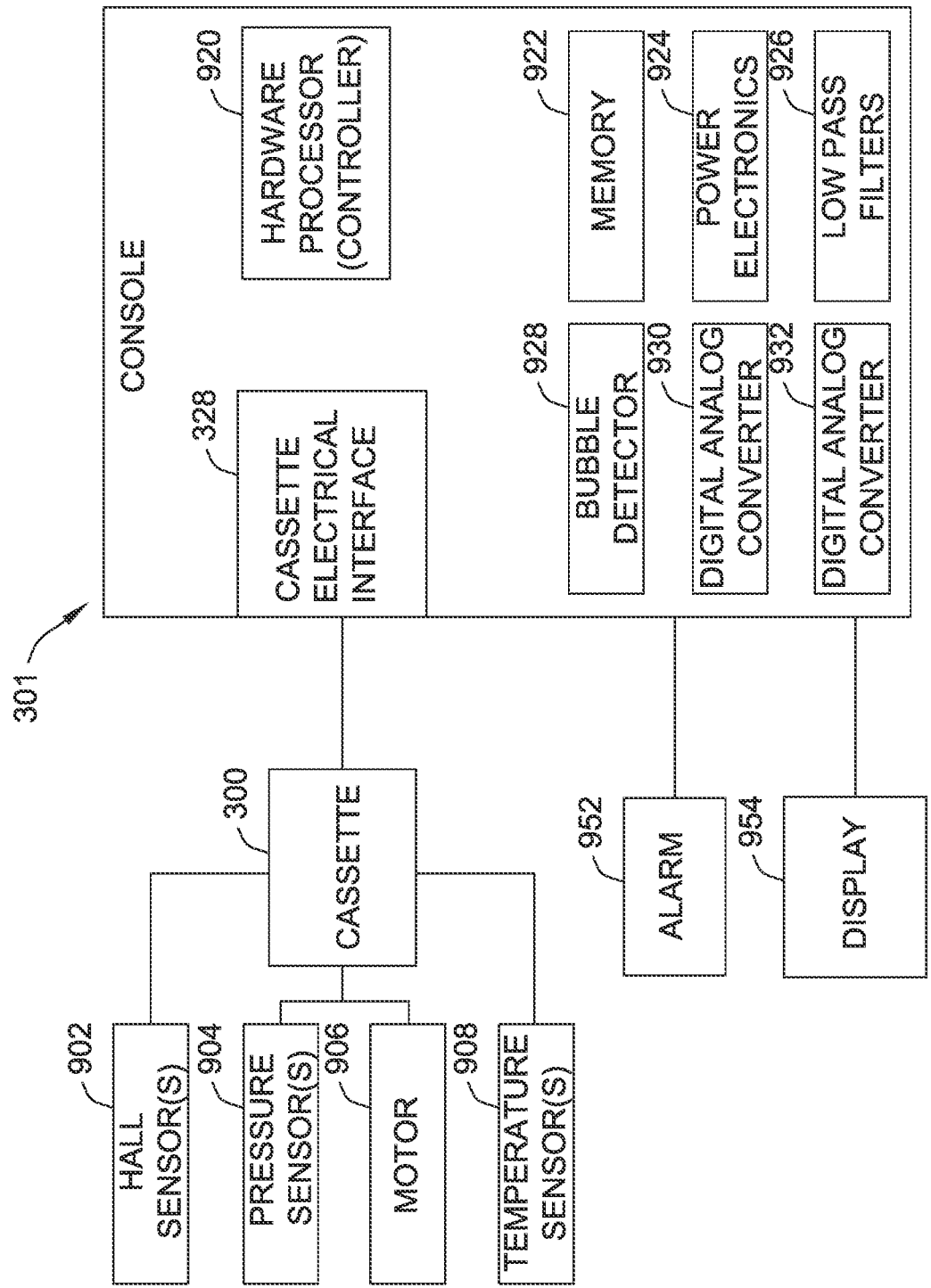
FIG. 9 illustrates a block diagram of a console and the electrical connections between the console and the various components of the fluid handling system, according to one embodiment.

FIG. 9 illustrates a block diagram showing electrical connections between an embodiment of the console 301 and the cassette 300, which may be further connected to one or more Hall sensor(s) 902, one or more pressure sensors 904, a motor 906, and one or more temperature sensors 908. Examples of pressures sensors 904 include pressure sensors 344a, and 344b discussed above with respect to the detecting pressure in the pump tube segments. The console 901 can also include a display 954. In some embodiments, the console 901 includes a separate alarm module 952. The alarm module can include an additional display and/or a speaker. The alarm module 952 can also be integrated with the display 954.

The console 301 can include a hardware processor or controller 920 as discussed above. In an embodiment, the console 301 includes multiple hardware processors. For example, a separate hardware processor can control the display 954. In some embodiments, the hardware processors include ASICs as discussed above. In some embodiments, the console 301 may be connected to a network for transferring data to a remote system. The console 301 can also include a memory 922 for storing system conditions including parameters or thresholds for alarms or controlling other operations of the console 301. The console 301 can include a digital to analog converters 930 and 932. In an embodiment, the digital to analog converter 932 is implemented entirely in hardware. The converters 930 and 932 can also operate as analog to digital converters. These converters can be used by the console 301 to communicate with external devices such as the motor 906, alarm 952 or the sensors discussed above. The console 301 can also include additional circuitry such as power electronics 924 and the low pass filters 926. The power electronics 924 can for example provide power to motor 906. The filter 926 may be used by the console 301 to selectively remove noise or select a particular band of interest.

The console 301 can also include an electrical interface 328 for receiving and sending signals from the console 301 to various components of the fluid handling system via the cassette or puck 300. The cassette 300 may be the same as or similar to the interface member 300 illustrated and described in detail above. The cassette 300 can electrically connect with multiple sensors and motors.

Figure 10:
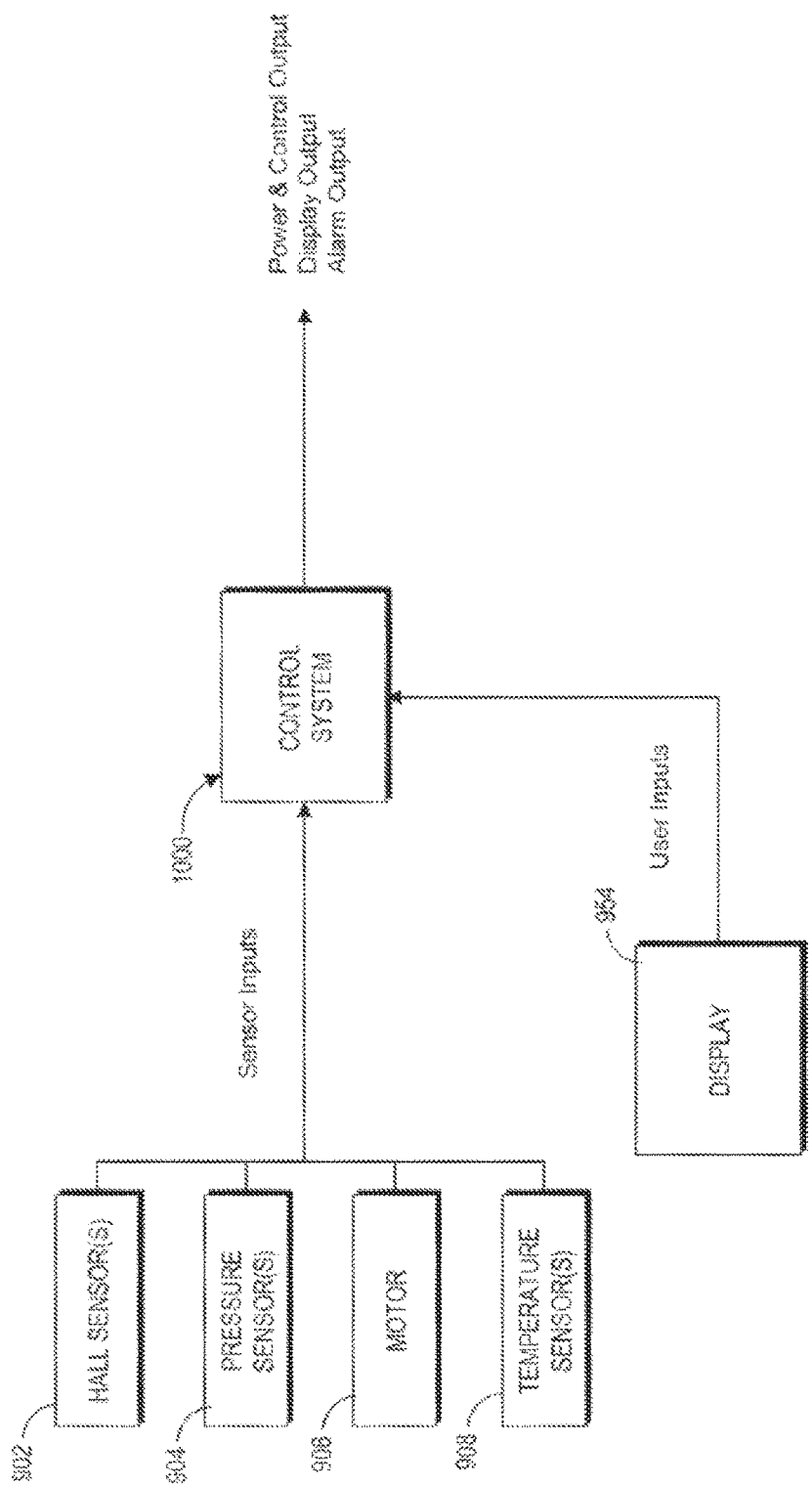
FIG. 10 illustrates a block diagram of the inputs and outputs of a control system, according to one embodiment.

FIG. 10 illustrates an embodiment of a control system 1000 for receiving inputs and controlling operation of the fluid handling system based on the received inputs. The control system 1000 can also receive user inputs via the display 954 or other user input controls (not shown). The control system 1000 can be implemented using the hardware processor 920. The control system 1000 can include programming instructions to implement some or all of the processes or functions described herein including controlling operations of priming, providing instructions and support to caregivers, and improving the automated functionality. The programming instructions of the control system 1000 can be saved in the memory 922. Some or all of the portions of the control system 1000 can also be implemented in application-specific circuitry (e.g. ASICs or FPGAs) of the console 301.

Figure 11:
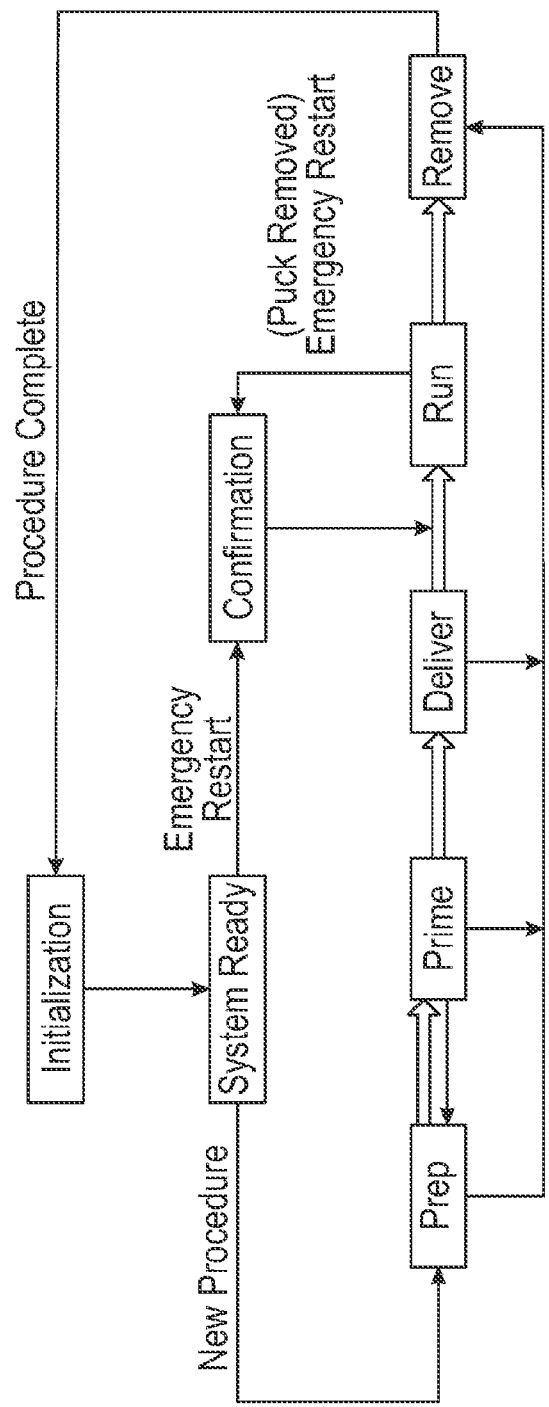
FIG. 11 illustrates a flow chart of a process 1100 that can be managed using the control system, according to one embodiment.

FIG. 11 illustrates an embodiment of a process 1100 that can be managed using the control system 1000. In an embodiment, the control system 1000 automatically controls all aspects of the process 1000. For example, the control system 1000 can receive inputs from the sensors discussed above and perform operations based on a determination that the parameters are in an operating range. The control system 1000 can also dynamically adapt based on detected parameters. In some embodiments, the control system 1000 can operate semi-automatically in conjunction with operations performed by a caregiver. The control system 1000 can guide operations, perform checks, and provide instructions dynamically based on detected problems, such as for example, a detection of bubbles. Accordingly, the control system 1000 can advantageously improve the operations of the console 301 and the catheter pump system.

As discussed above, the control system 1000 can assist users in the priming operation of the catheter pump system. In some embodiments, it may be advantageous to have at least some or all of the aspects of the priming operation automated using the control system 1000. The control system 1000 can also provide feedback to the users to guide them in successfully completing the priming process. The control system 1000 can use the sensor inputs to determine parameters of the system. Based on the determined parameters, the control system 1000 can provide audio or visual output. In an embodiment, the control system 1000 can generate user interfaces for output to the display 954. The user interfaces can include feedback from the determined system parameters.

Figure 12:
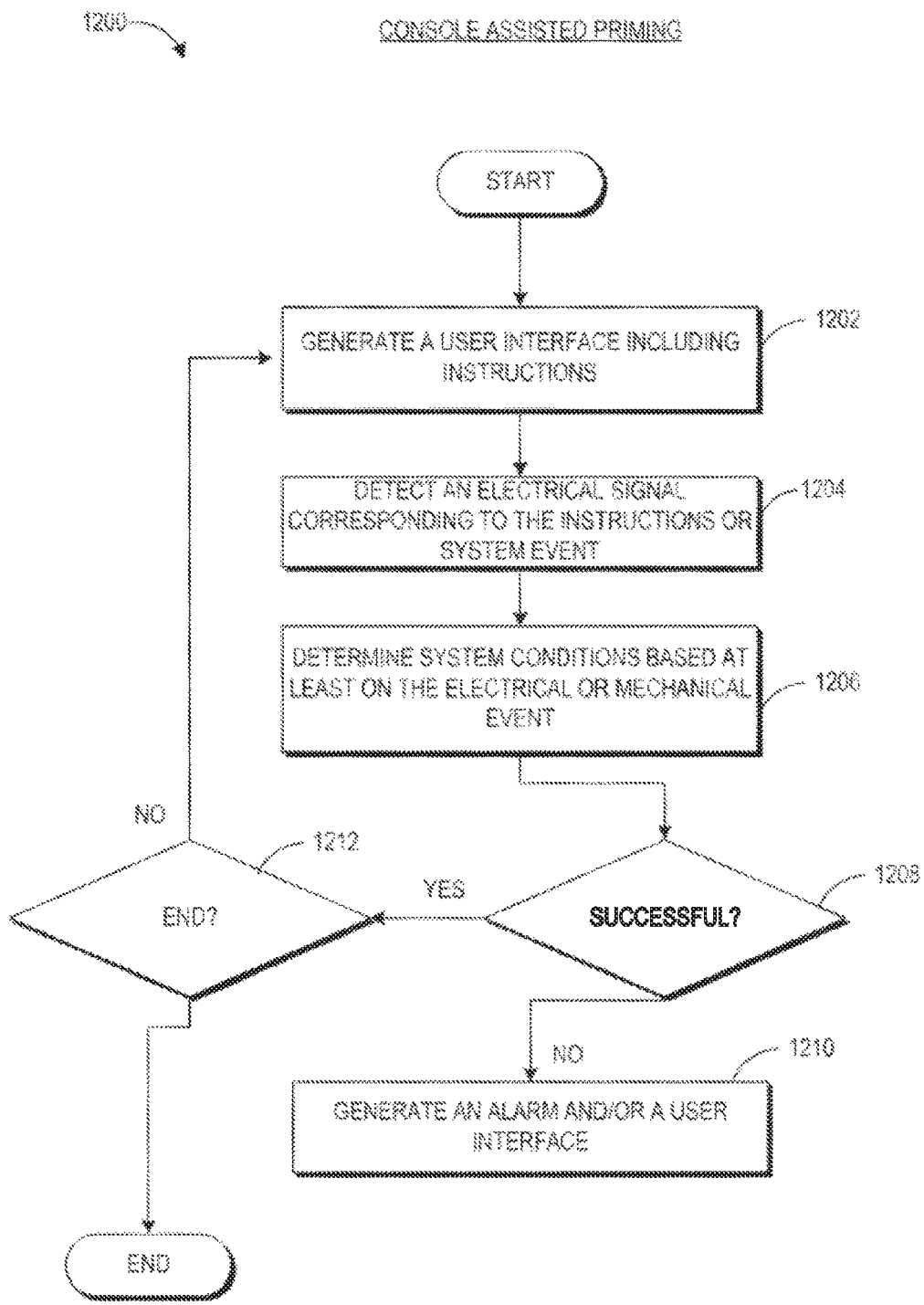
FIG. 12 illustrates a process 1200 for using the control system to assist with the priming process, according to one embodiment.

FIG. 12 illustrates an embodiment of a process 1200 for using the control system 1000 to assist with the priming process. The process 1200 can be implemented by any of the systems described herein. In an embodiment, the process 1200 is implemented by the control system 1000. The process can begin at block 1202 with the control system 1000 generating one or more user interfaces and sending the user interfaces to the display. The user interface can include instructions for a user to prepare for the priming process. Example user interfaces are described in detail below with respect to FIG. 14 to FIG. 51. The control system 1000 can also receive inputs from selection by a user on the generated user interfaces.

At block 1204, the control system 1000 can detect electrical signals from various hardware components of the fluid handling system in response to a user following a first set of instructions. For instance, the control system 1000 can monitor electrical signals from a combination of the pressure sensor(s) 904, temperature sensor(s) 908, Hall sensor(s) 902, and other components of the fluid handling system. In some embodiments, the control system 1000 can determine system parameters or conditions from the received electrical signals at block 1206. System parameters may include flow rate, pressure differences, bubble detection, motor speed, motor current, temperature of the motor, temperature inside the console, etc.

The control system 1000 can also monitor a connection state of the various components of the fluid handling system. For example, the control system 1000 can detect whether the cassette 300 is properly attached to the console 301. The control system 1000 can also determine if a saline bag is empty as discussed herein. The specific parameters and operation of the control system 1000 is described in more detail below with respect to the user interfaces.

At block 1208, the control system 1000 can determine whether the user can proceed to the next step or if there is a problem with the system conditions. For example, if the control system 1000 determines that the puck is not properly attached, the control system 1000 can generate an alarm at block 1210. The alarm can be generated as an audio alarm and/or displayed on the display. The control system 1000 can also detect other conditions, such as a bubble in the line, using an optical or acoustic sensor or the like. Some of these conditions may not be readily apparent to the users and may result in malfunction or improper therapeutic operation of the catheter pump system. Accordingly, the control system 1000 can improve the operation of the catheter pump system by determining system conditions based on electrical and mechanical events that may not have been detected in the absence of the control system 1000.

If at block 1208, the control system 1000 determines that the user was successful in following the instructions based on the determined system conditions, the control system 1000 can determine if all the steps of priming are completed at block 1212. If not completed, the control system 1000 can generate another user interface indicating a next set of instructions. The generated user interface can also indicate status of the system. For example, the generated user interface can indicate flow rate, motor current, motor speed, time remaining for priming, cassette connected. In some embodiments, the control system 1000 can automatically carry out some of the instructions based on successful completion of previous instructions. For example, when the control system 1000 determines that a cassette is detected and properly attached, the control system 1000 can automatically start pumping fluid to prime the system.

Accordingly, the control system 1000 can assist a user in completing the priming operation. The control system 1000 can maintain a system state in the memory throughout the operation of the process 1200. The system state can include parameters described herein including connection state of various components.

Figure 13:
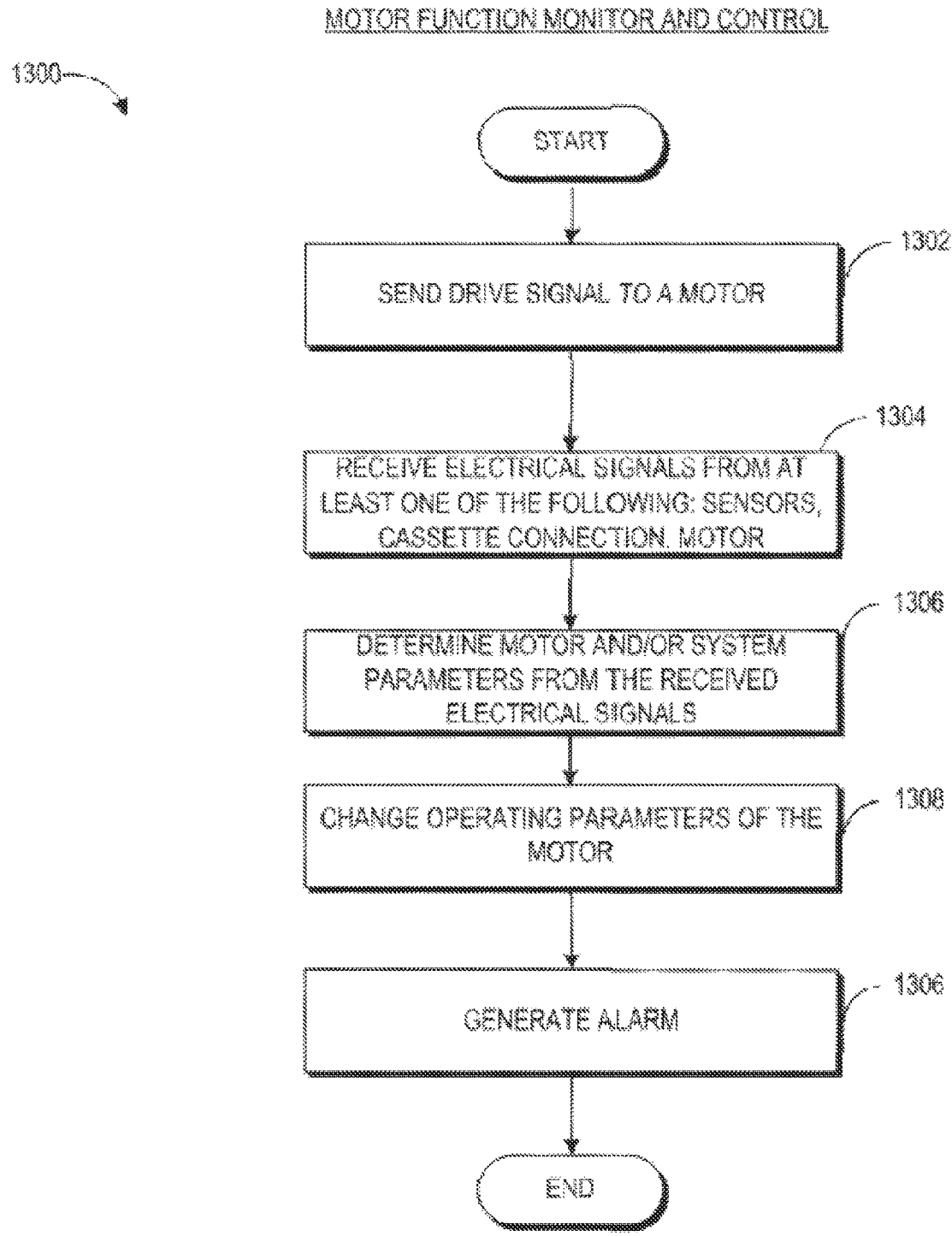
FIG. 13 illustrates a process 1300 for controlling operation of the motor using the control system, according to one embodiment.

FIG. 13 illustrates an embodiment of a process 1300 for controlling operation of the motor 906 using the control system 1000. In an embodiment, the motor 906 is the motor that drives the impeller. For example, in some embodiments, the motor 906 can be disposed outside the body of the patient, and can rotate a drive shaft extending through the catheter to drive the impeller. In other embodiments, the motor can be miniaturized and inserted into the body, with one or more wires extending through the catheter to connect the motor 906 with the control system 1000. In some embodiments, the control system 1000 can implement the process 1300 for other motors of the system such as the peristaltic pump motor that pumps saline solution for lubrication. Accordingly, the control system 1000 can use the process 1300 for controlling many motors of the catheter pump system.

The process can begin at block 1302 with the control system 1000 sending a drive signal to a motor. The drive signal can be a low power control signal to activate the motor 906. The motor 906 can receive power for its operation from another source. In response to receiving the drive signal, the motor can begin its operation. In some embodiments, it may be advantageous to monitor the operation of the motor 906 for protecting the motor 906. Monitoring the motor can also reveal system conditions as discussed above including, for example, detection of a blockage in a line.

Thus, at block 1304, the control system 1000 can monitor various electrical signals from the motor, sensors, and other components that can directly or indirectly provide indication of operation of the motor 906.

At block 1306, the control system 1000 can determine parameters corresponding to the received electrical signals. Parameters can include motor speed, motor current, peristaltic pump speeds, pressure sensor outputs, temperature sensor output, bubble detector status, battery voltage, battery charge level, and battery temperature. The control system 1000 can store these parameters over time to monitor change in the state of the catheter pump system over time.

Further, at block 1306, the control system 1000 can determine if any of the parameters discussed above exceeds a predetermined threshold. In an embodiment, the control system 1000 may prevent the motor current from exceeding a motor current threshold of 1.2 A. In some embodiments, the motor current threshold can be in a range of 0.5 A to 5 A, 0.5 A to 3 A, 0.5 A to 2.5 A, 1 A to 3 A, or 1 A to 2 A. The control system can also compare the measured motor speed with predetermined values stored in the memory. The thresholds may vary depending on the size of the motor and other motor characteristics. In some embodiments, the control system 1000 calculates flow rate based on the readings from the pressure sensor, such as the outer sheath pressure sensor (which may comprise a column of fluid that extends distally through the catheter body) and the catheter motor speed. The control system 1000 can use a lookup table for the relationships between the flow rate, motor speed, and pressure. Based on these stored parameters, the control system 1000 can correlate the flow rate, pressure, with motor speed to determine system conditions. For example, if the motor is drawing large current, but the large current is not translated into flow rate, the control system 1000 can determine an existence of a system condition, such as blockage or a bind in the impeller and/or drive shaft.

In some embodiments, when the parameters fall outside of predetermined operating parameters, the control system 1000 can modify the drive signal to the motor. For example, when the control system 1000 determines that the motor has stopped spinning based on a measured motor speed or if the motor 906 is drawing excessive current, the control system 1000 can generate an alarm and may switch to a backup motor or a secondary console.

The control system 1000 can also compare the motor current and motor speed, for example, in revolutions per minute with a lookup table. The lookup tables can be stored in the memory. If the motor current is below or above a certain predetermined range for a particular motor speed, the control system 1000 can generate an alarm.

In some embodiments, the control system 1000 can determine that the cassette 300 has been removed or connection with the cassette 300 has been lost. The control system 1000 can stop the motor 906 in response to the detection that connection with the cassette 300 has been lost. As discussed above, the motor 906 can be the impeller motor. Stopping the impeller motor when the connection with the cassette is lost may be advantageous in some embodiments to protect the components and therapeutic efficacy of the fluid handling system.

Alarm can be audio and/or visual. The control system 1000 can generate a user interface with the alarm and send it to the display. In some embodiments, at block 1308, the control system 1000 can reduce power or increase power supplied to the motor based on the determinations of at least one of the following: the flow rate, pressure, motor current. The control system 1000 can also stop sending the drive signal to the motor if the parameters exceed threshold.

Figure 14:
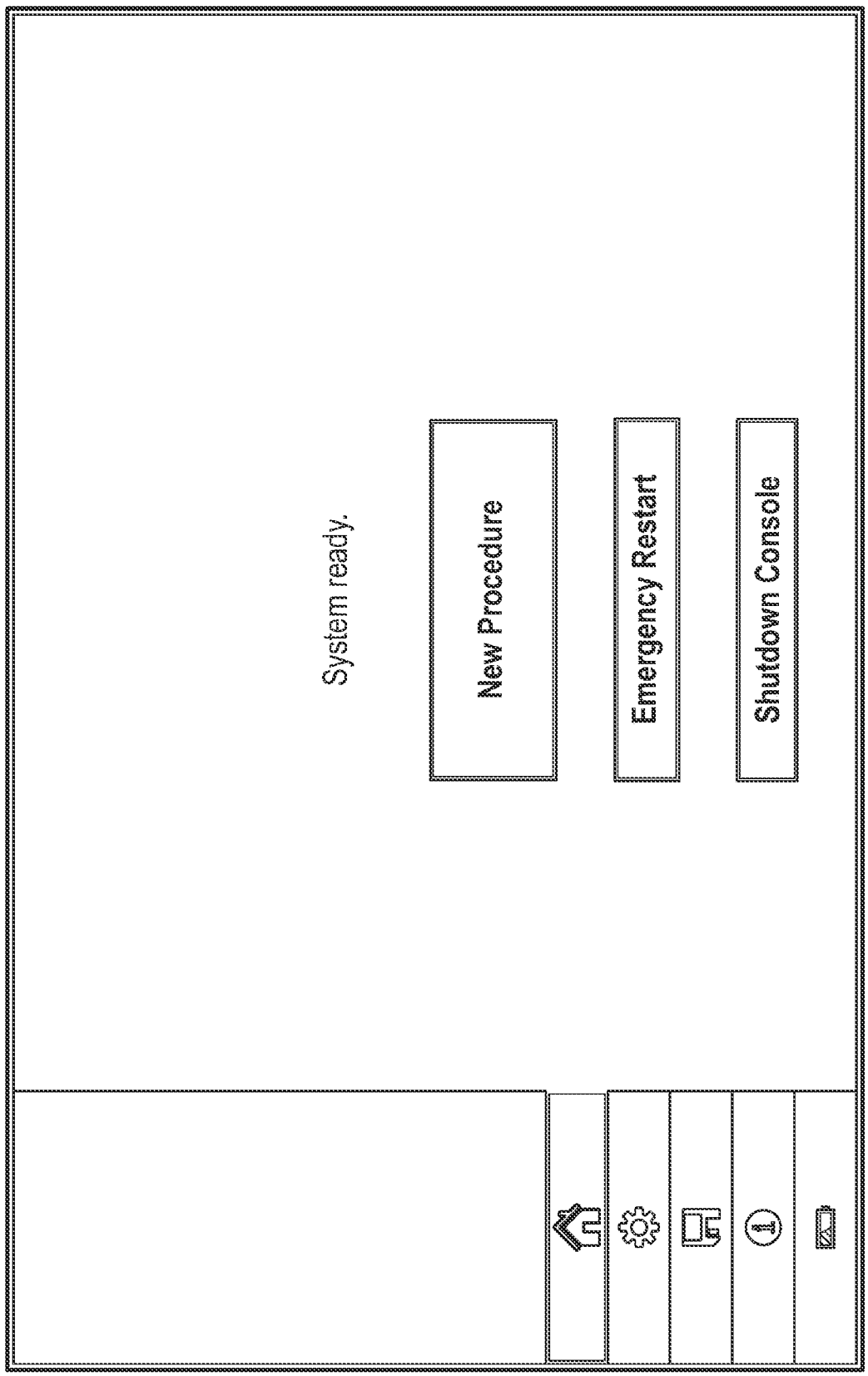
FIG. 14 illustrates an embodiment of a startup user interface, according to one embodiment.

FIG. 14 illustrates an embodiment of a startup user interface. The startup user interface can include multiple active links corresponding to operation of the catheter pump system and/or the fluid handling system. In the illustrated example, the startup user interface includes active links for performing a new procedure, emergency restart, and shut down. The startup user interface can also display system status. In the example, the startup user interface shows a text, "System ready." The text can be generated by the control system 1000 in response detecting that the cassette 300 is properly attached to the console 301. The control system 1000 can also generate the text based on determination of other system parameters discussed herein.

Figure 15:
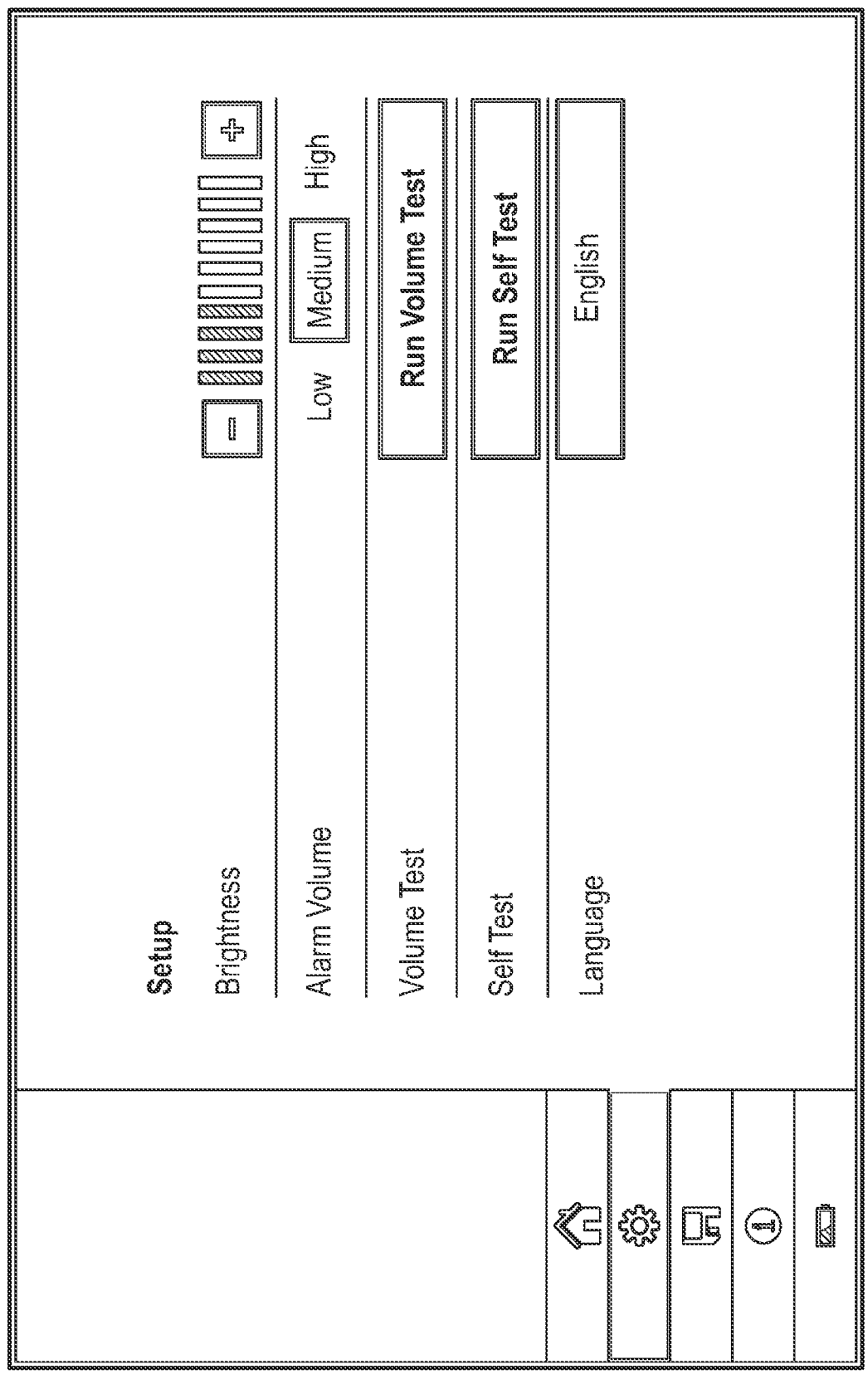
FIG. 15 illustrates system setup user interface for changing settings related to the console, according to one embodiment.

FIG. 15 illustrates an embodiment of a system setup user interface for changing settings related to the console. In an embodiment, the system setup user interface can be used by caretakers to change alarm conditions described herein. The setup user interface can also include an active link for testing the system. In the illustrated example, when a user selects the "Self Test" link, the control system 1000 can run multiple checks on the components of the fluid handling system including the console to determine any problems. For example, the control system 1000 can check for battery status, check motor(s) by doing a sample run and measuring motor parameters, such as speed, power, current drawn by the motor. In some embodiments, the control system 1000 can determine flow rate to determine if there are any occlusions. Flow rate can be calculated based on pressure differences measured by the pressure sensors.

Figure 16:
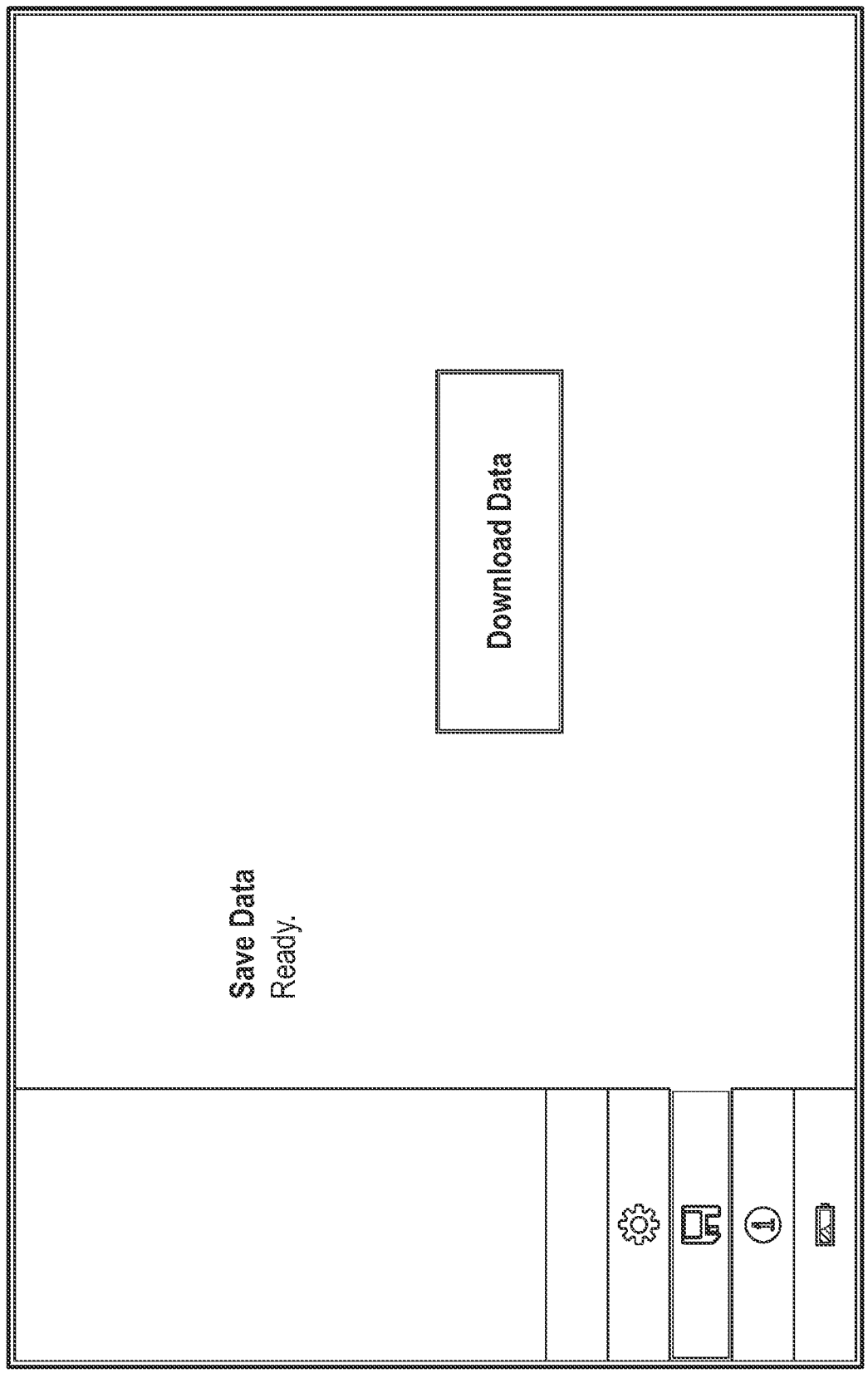
FIG. 16 illustrates a save data user interface generated by the control system, according to one embodiment.

FIG. 16 illustrates an embodiment of save data user interface generated by the control system 1000. The save data user interface can enable users to save the measurements from the console on to an external drive. In some embodiments, the control system 1000 can send stored data over a network to a computing device. The control system 1000 can also receive instructions for operation over the network. In an embodiment, the network includes local network or internet or a combination of local and wide area network.

Figure 17:
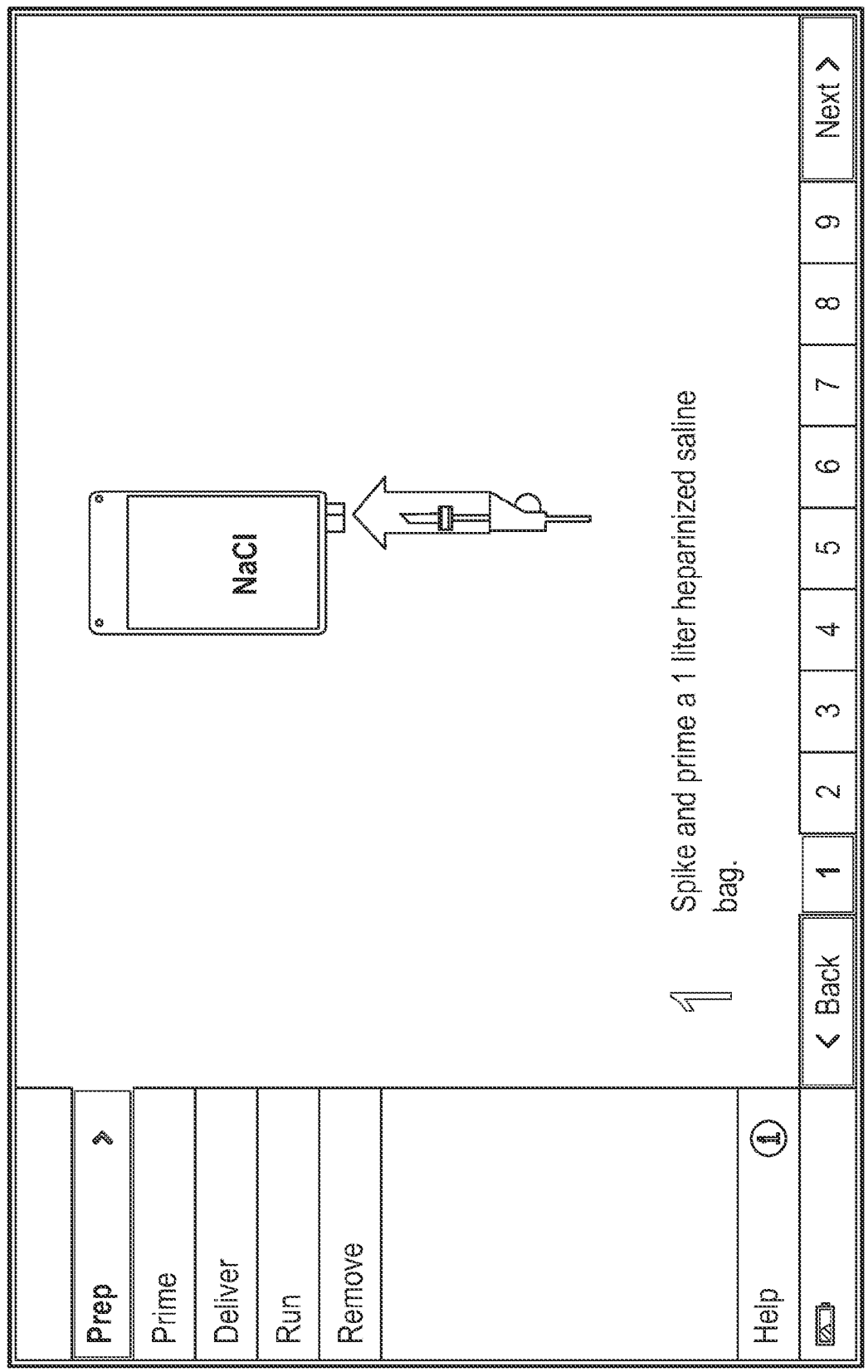
FIG. 17 illustrates a first prep screen user interface generated by the control system, according to one embodiment.

FIG. 17 illustrates an embodiment of a first prep screen user interface generated by the control system 1000. The first prep screen user interface can include instructions to enable a caretaker to prepare the fluid handling system. In the illustrated embodiment, the instructions relate to spiking and priming a 1 liter heparinized saline bag. In some embodiments, the control system 1000 may determine that instructions were successfully carried out by the caretaker. For example, the control system 1000 can run the pump and measure the pressure to determine whether the saline bag is connected properly. The control system 1000 can automatically move on to the next step in the process based on the successful completion of the current instructions. In some embodiments, the control system 1000 can request input from the caretaker to move to the next step of the process. The numeral (e.g. "1") shown in the prep user interface can indicate the current step or status.

Figure 18:
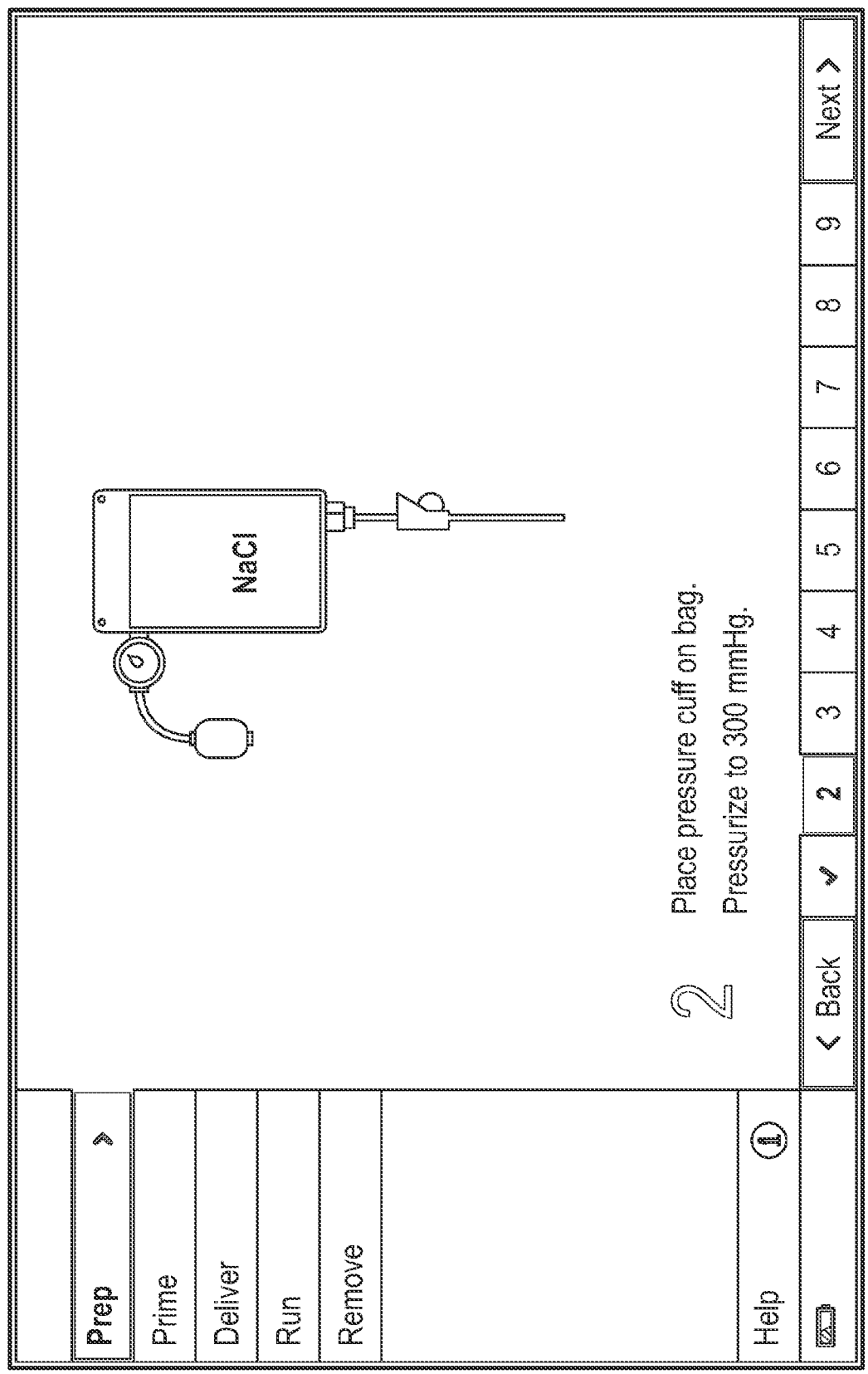
FIG. 18 illustrates a second prep screen user interface generated by the control system, according to one embodiment.
Figure 19:
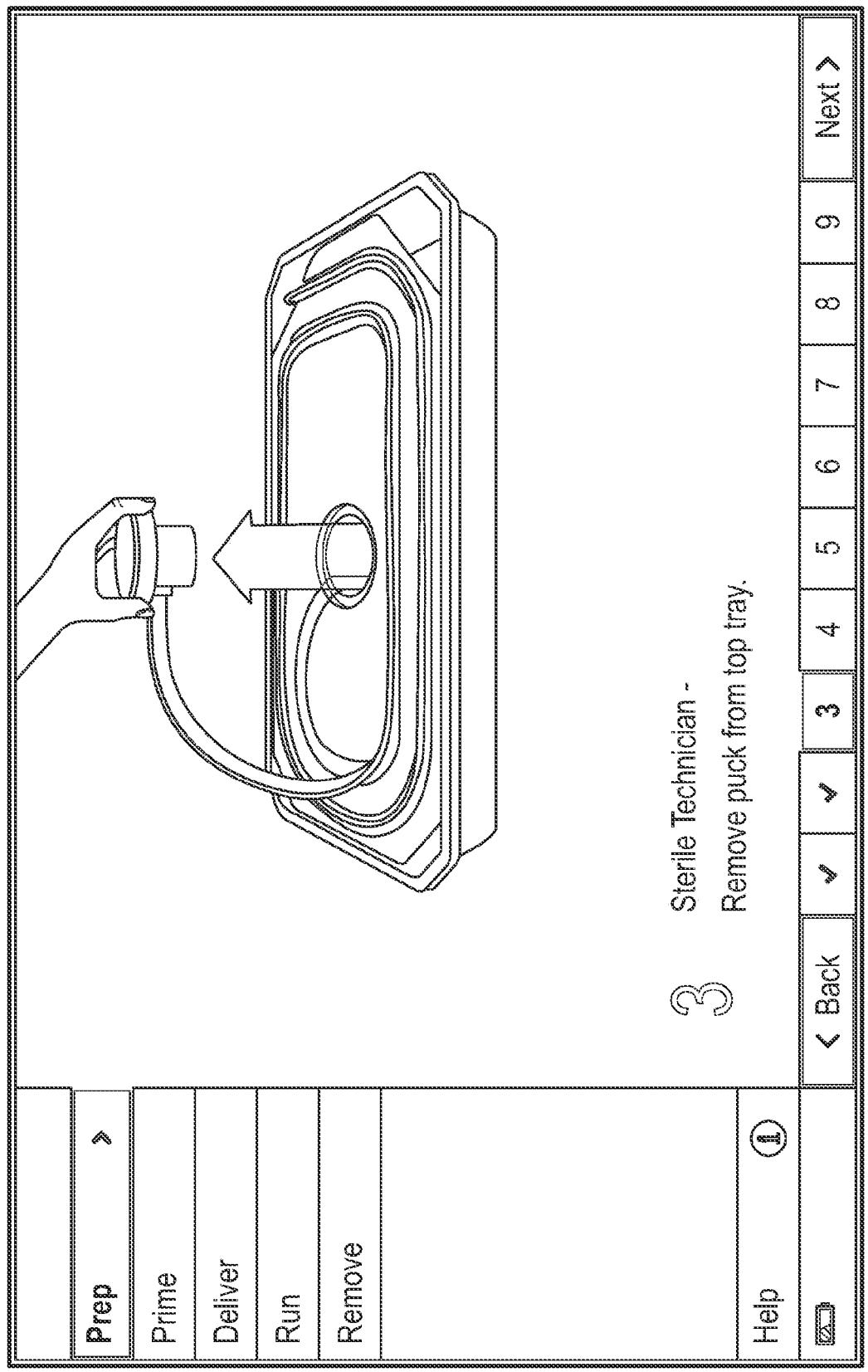
FIGS. 19 to 24 illustrate user interfaces corresponding to instructions relating to insertion of cassette (or puck), according to one embodiment.

FIG. 18 illustrates an embodiment of a second prep screen user interface generated by the control system 1000. The second prep screen user interface may correspond to a second set of instructions following the first set of instructions. As discussed above, the control system 1000 can generate the second prep screen user interface and send it to the display after a successful completion of the previous instructions as determined by the control system 1000. As illustrated, the user interfaces can also include a back and forward link to enable caretakers to navigate the instructions. In an embodiment, the control system 1000 can automatically navigate through the user interfaces based on the current system state, which can be stored in the memory. In the illustrated user interface, the instructions correspond to placing a pressure cuff on bag. The user interface can visually indicate the location of where the pressure cuff should go in relation to other components of the fluid handling system. In some embodiments, the control system 1000 can attempt to measure the pressure for detection of whether the pressure cuff was attached.

Figure 20:
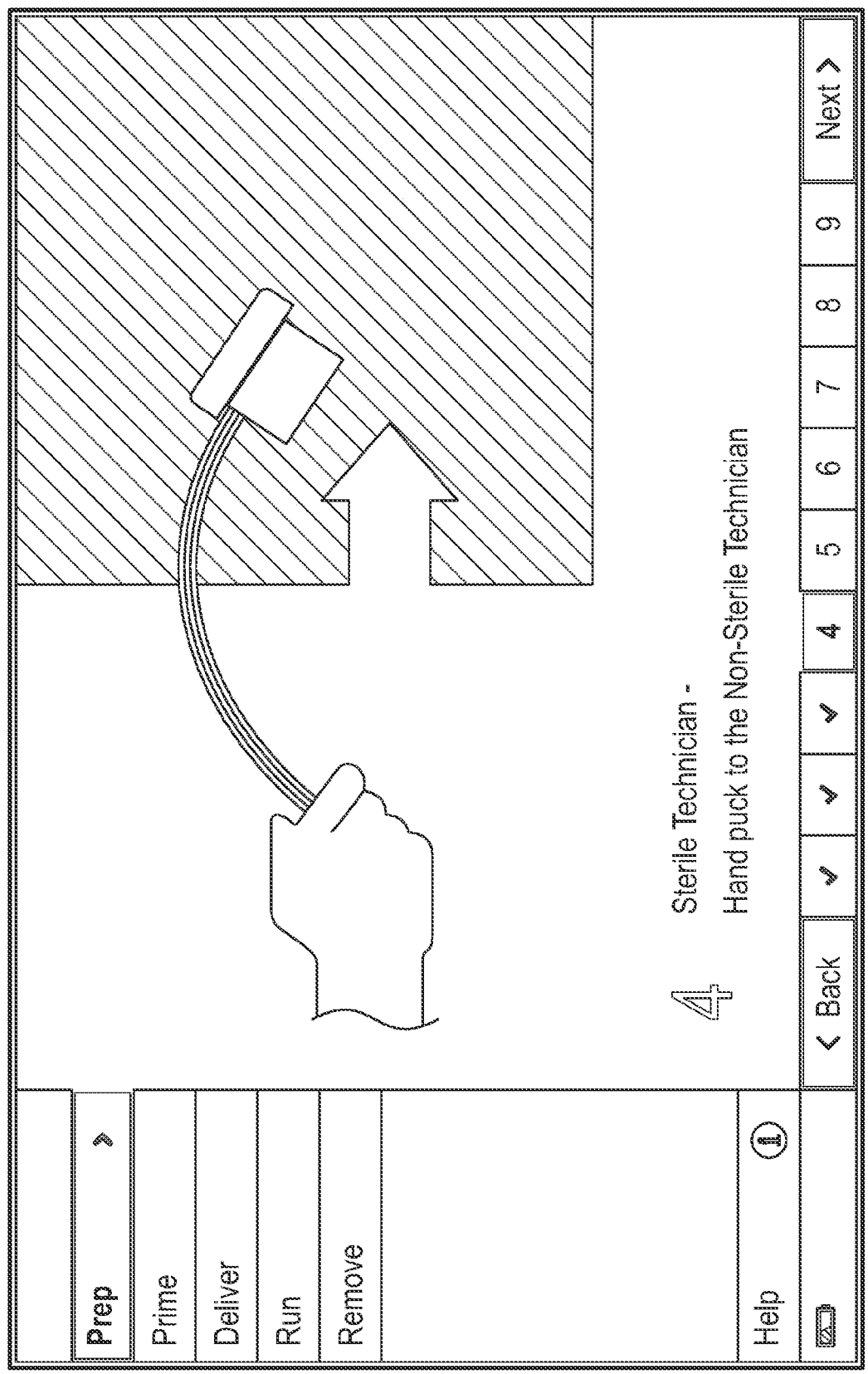

FIGS. 19 to 24 illustrate embodiments of user interfaces corresponding to instructions relating to insertion of cassette (or puck). As discussed above, the control system 1000 can monitor if the instructions are successfully followed based on received electrical signals. For example, in some embodiments, the control system 1000 can detect removal of puck from top tray based on a change in electrical connection between the puck and the top tray. The change may be a measurement of current, resistance, or voltage. In other embodiments, the user may advance to the next screen manually by engaging with the user interface. FIG. 20 illustrates an example where the control system 1000 may request a user to perform an instruction and manually select the next link. In some embodiments, the control system 1000 can run a timer for each instruction and optionally display it on the user interface so that the next task screen is automatically displayed.

Figure 21:
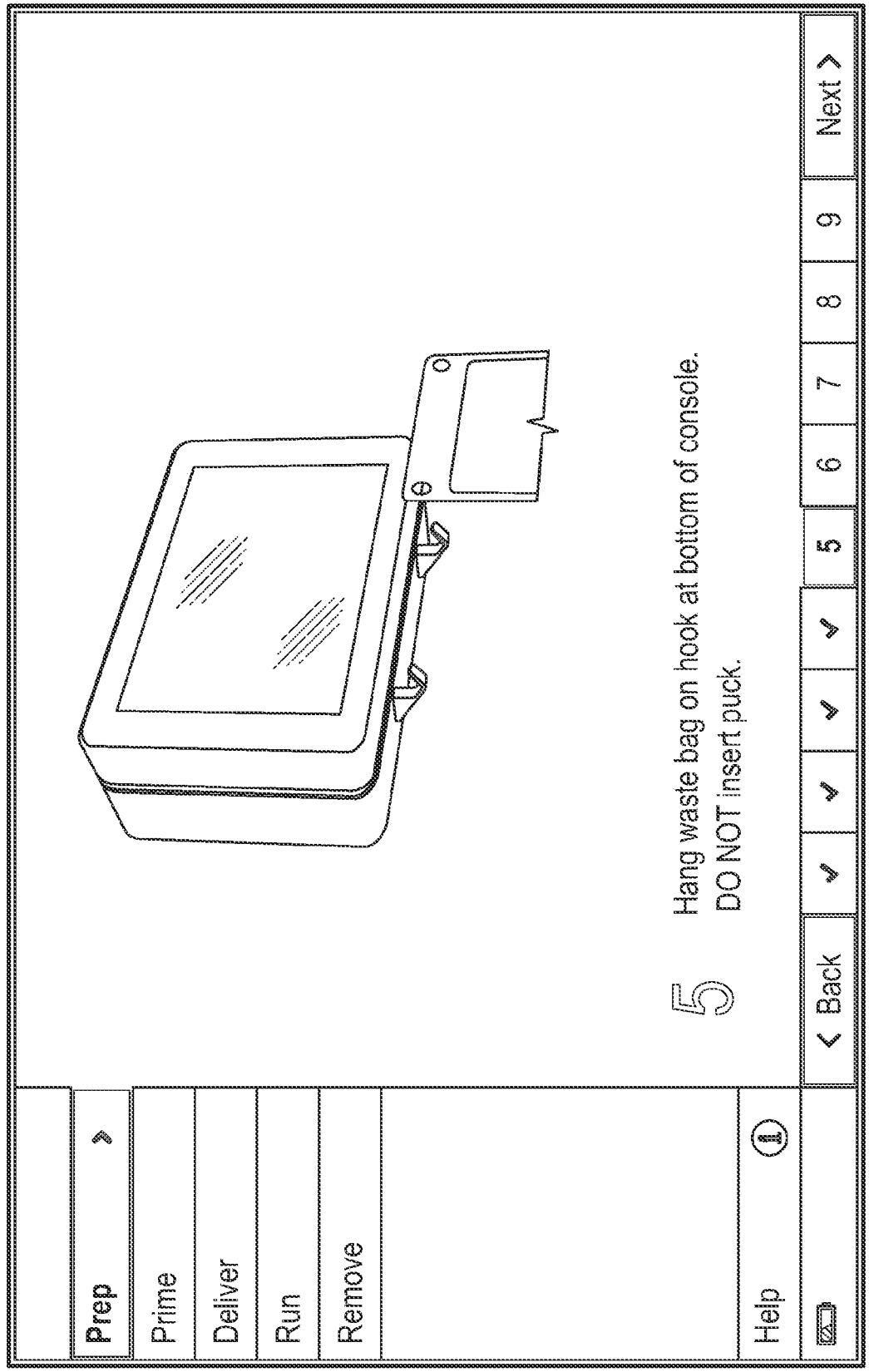
Figure 22:
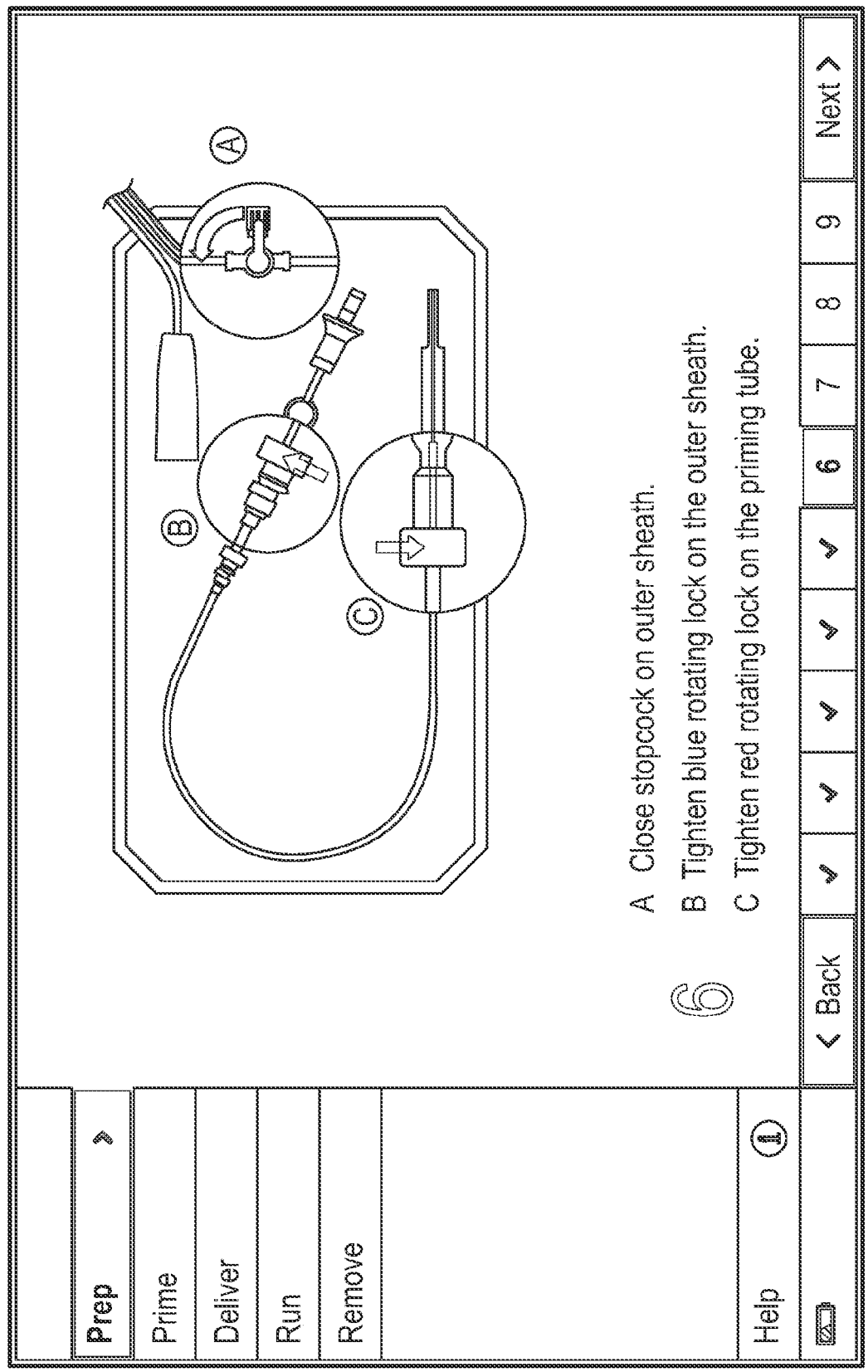

In FIG. 21, the user interface includes instructions corresponding to hanging waste bag on hook at bottom of console prior to attaching the cassette 300 with the console 301. The control system 1000 can monitor attachment of the cassette 300. If the user inserts the cassette 300 before completion of the instructions, the control system 1000 can generate an alert. Monitoring attachment of the cassette 300 can be performed via electrical signals. For example, when the cassette 300 is attached, an electrical circuit might close and cause current flow, which can be detected by the control system 1000. In some embodiments, attachment of the cassette 300 can be detected by measuring a fixed-value resistor in an electrical circuit of the puck. Different values of resistors can indicate different types of cassette connected. In some embodiments, the control system 1000 can change its operating parameters based on the electrical circuit configuration in the puck. FIG. 22 illustrates user interface for instructions corresponding to the sixth step in the prepping process. In some embodiments, the control system 1000 can selectively animate the instructions visually on the user interface when multiple instructions are displayed on a singles user interface as shown.

Figure 23:
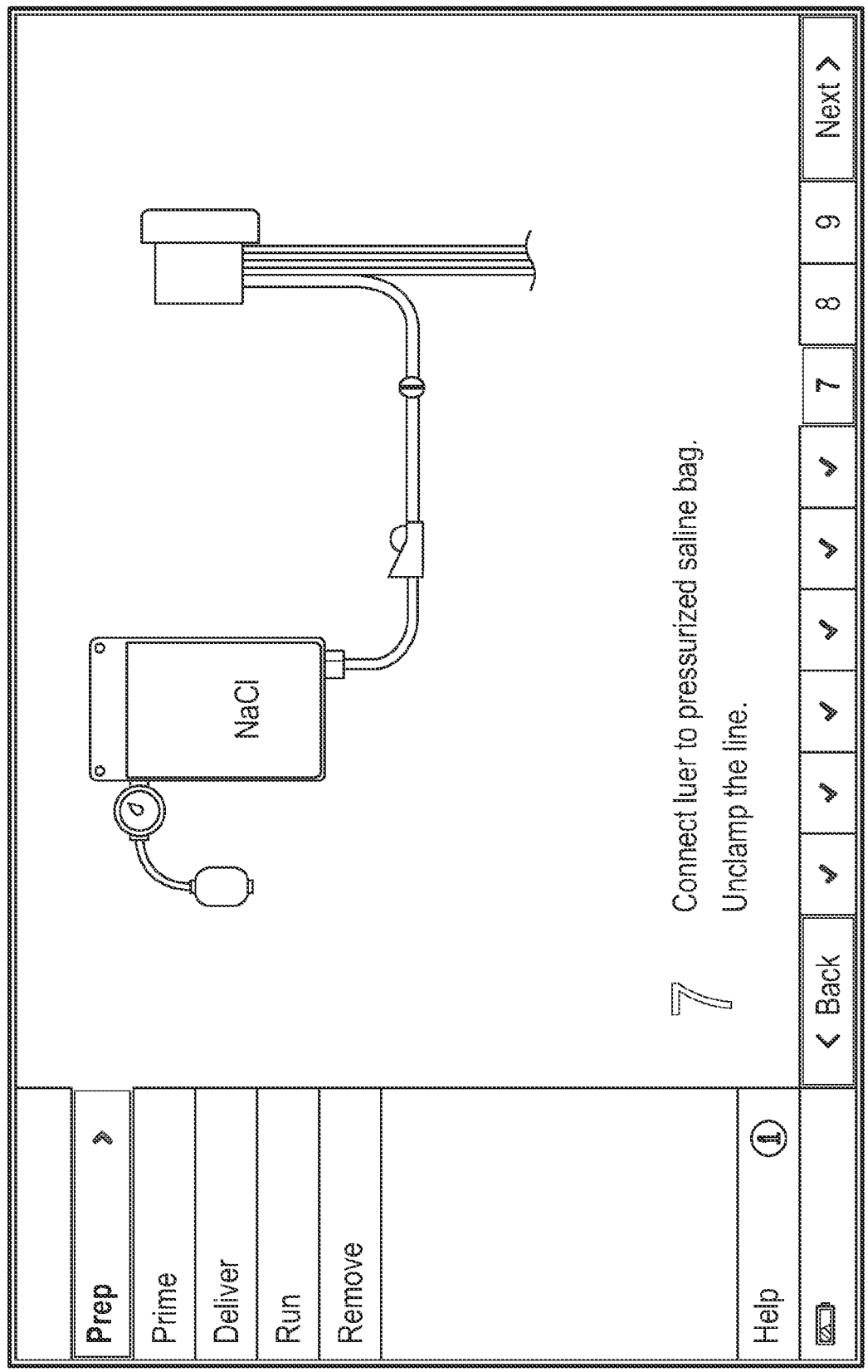

FIG. 23 illustrates an embodiment of a user interface generated by the control system 1000 including instruction to unclamp the line connecting to the pressurized saline bag. The control system 1000 can automatically determine if the caretaker has unclamped the line. For example, the control system 1000 can take pressure measurement from the pressure sensors discussed above and generate an alarm or an indication to unclamp the line before moving on to the next set of instructions.

Figure 24:
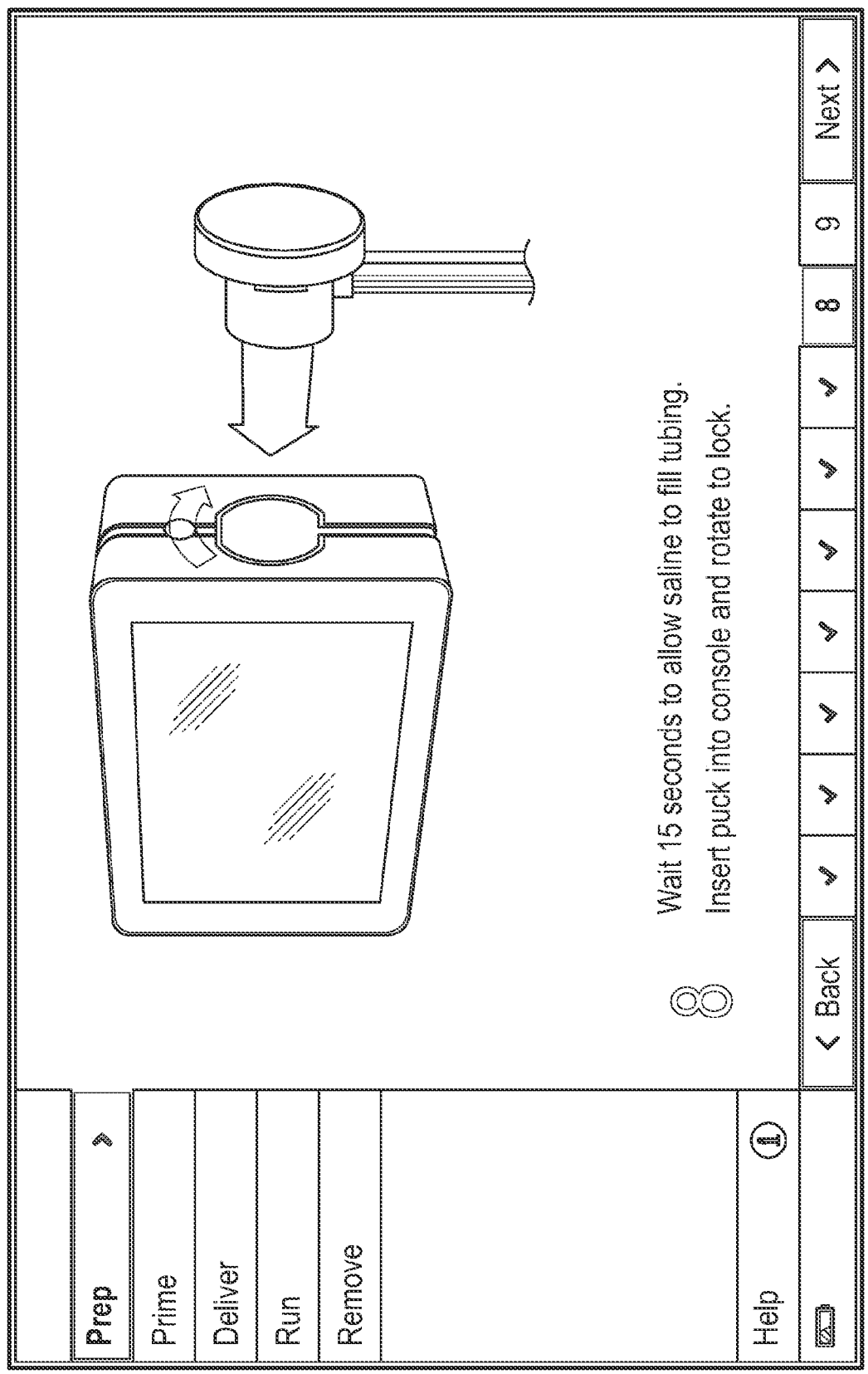

FIG. 24 illustrates an embodiment of a user interface generated by the control system 1000 including instructions to insert cassette 300 into the console 301. In some embodiments, the fluid handling system may require a certain amount of time to elapse after unclamping the line as instructed in FIG. 23. In the illustrated example, the elapsed time is 15 seconds. The control system 1000 can include a timer and display an indication when the cassette is ready to be attached. The control system 1000 can measure the pressure to determine if the saline has not filled the tubing and generate an alarm indicator.

Figure 25:
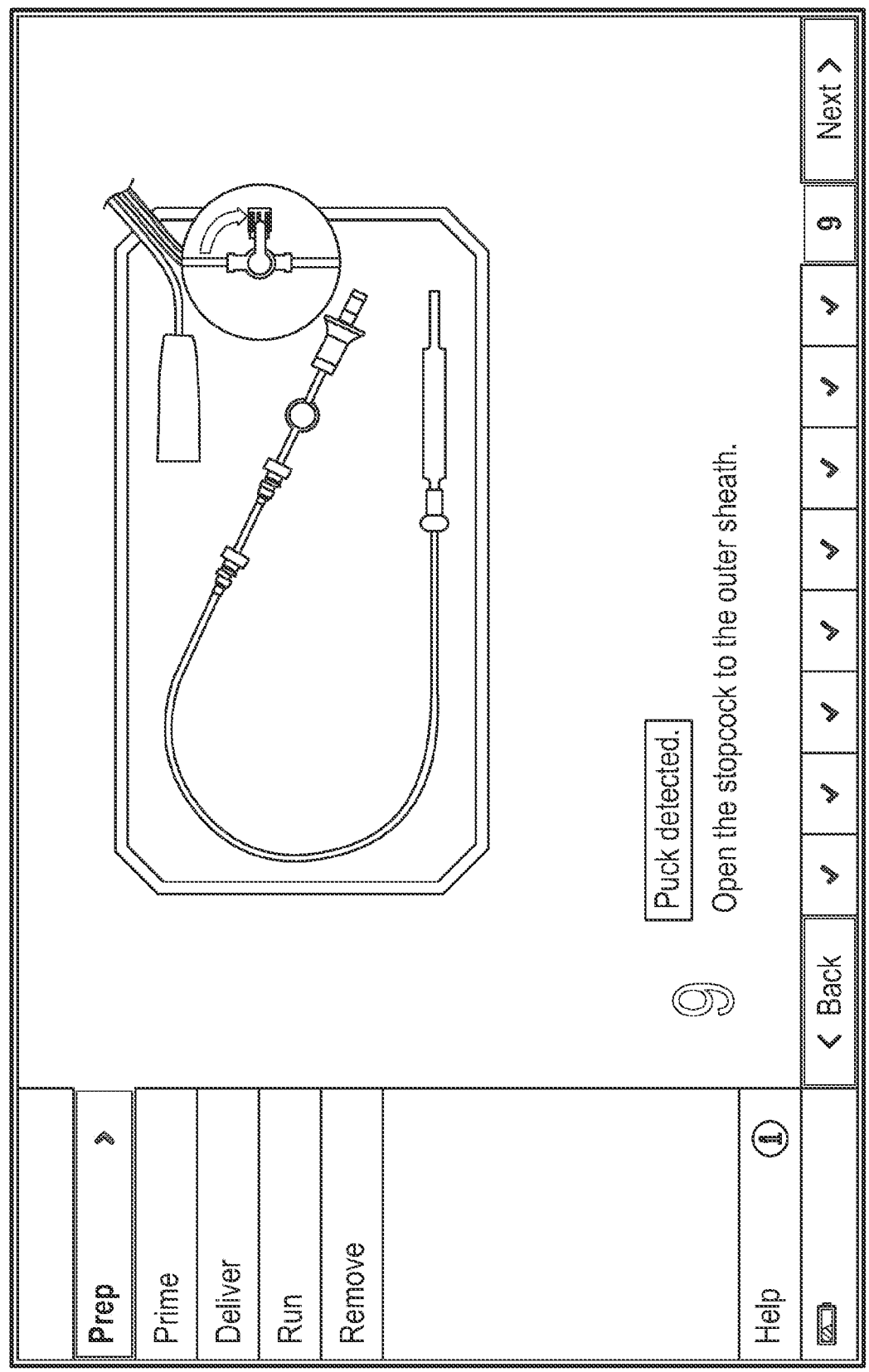
FIG. 25 illustrates a user interface generated by the control system indicating that the cassette was successfully connected with the console, according to one embodiment.
Figure 26:
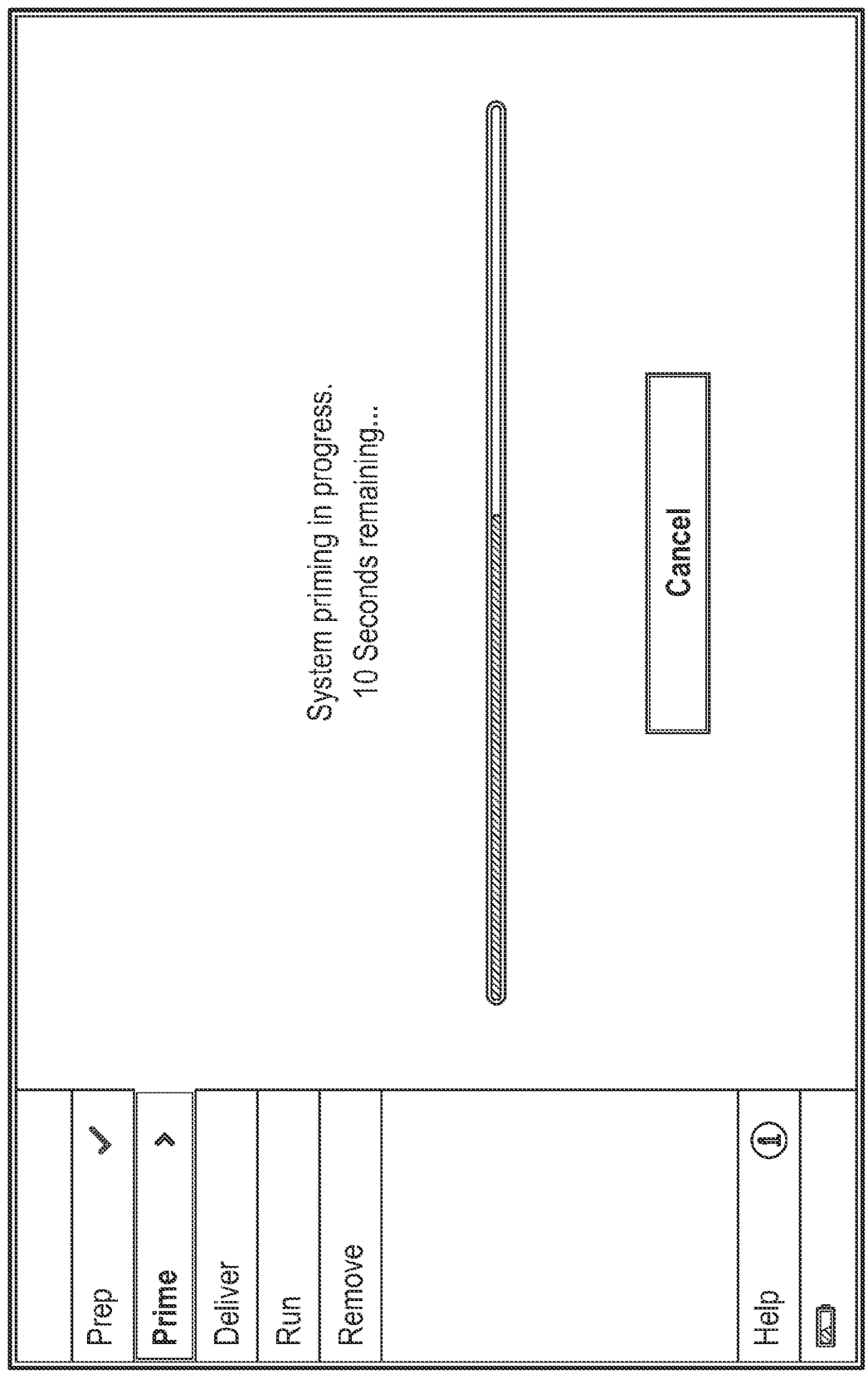
FIG. 26 illustrates a user interface displaying the indication of progress, according to one embodiment.

FIG. 25 illustrates an embodiment of a user interface generated by the control system 1000 indicating that the cassette 300 was successfully connected with the console 301. In some embodiments, the control system 1000 can automatically start the priming process responsive to detecting the puck and display the indication of progress as shown in FIG. 26. For example, the control system 1000 can send a signal to the peristaltic pump to operate at a particular rate for a period of time. In an embodiment, the speed is 30 rpm or less. The period of time can be two minutes or less. The control system 1000 can also detect whether the stopcock to the outer sheath is opened before beginning the priming process.

The following disclosure describes some of the other parameters monitored by the control system 1000 during the operations illustrated in the instructional user interfaces above. It further describes some of the system conditions identified based on the monitoring. For example, the control system 1000 can monitor waste pressure sensor. In one embodiment, if the waste supply pressure is less than 200 mm Hg, the control system 1000 can determine there is a blockage. In another embodiment, the waste supply pressure of less than 150 mm Hg may indicate blockage. Further, a waste supply pressure of less than 200 mm Hg may indicate blockage in the saline line. The control system 1000 can also monitor saline supply pressure sensor. A saline supply pressure of less than a leak threshold pressure value can suggest a leak or empty bag. The leak threshold pressure value can be 200 mm Hg. In some embodiments, the leak threshold pressure value is less than 200 mm Hg or greater than 200 mm Hg. Furthermore, a saline supply pressure of greater than block threshold value may indicate a blockage in the saline line. The block threshold value can be 600 mm Hg. In some embodiments, the block threshold pressure value is less than 600 mm Hg or greater than 600 mm Hg. A saline supply pressure of less than 150 mm Hg can indicate there is no saline flow to catheter. In some embodiments, the control system 1000 can use a combination of measurements from the saline supply pressure and the waste pressure sensor to determine if there is a leak (for example, saline supply pressure less than 200 mm Hg and waste pressure sensor less than 100 mm Hg) or blockage (for example, saline supply pressure>550 mmHg and waste pressure sensor<150 mmHg). Furthermore, in some embodiments, the control system 1000 can monitor outer sheath pressure during priming. An outer sheath pressure of less than 35 mm Hg during priming may be a result stopcock being closed or infusion set clamp closed off or blockage in saline line. The control system 1000 can indicate an alarm including particular problems based on the detected conditions. The control system 1000 can also stop the prime timer until the condition is resolved.

Figure 27:
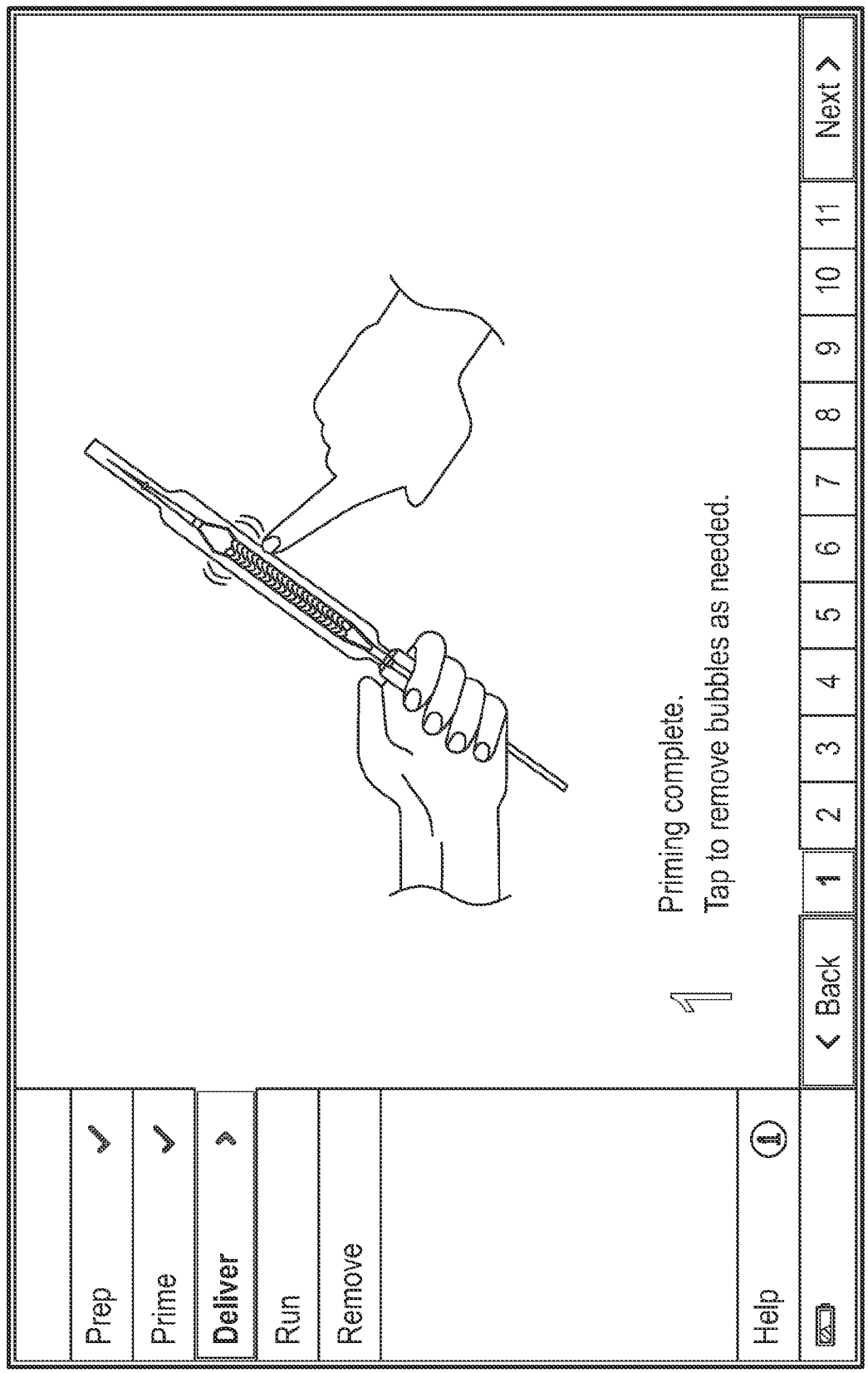
FIG. 27 illustrates a user interface generated by the control system indicating that the priming process has been completed, according to one embodiment.

FIG. 27 illustrates an embodiment of a user interface generated by the control system 1000 indicating that the priming process has been completed. In an embodiment, the control system 1000 can determine whether there are bubbles in the tube and indicate to the caretaker to remove the bubbles. In some arrangements, the caretaker can tap the distal end of the priming vessel to cause the bubbles to exit the distal end of the system. In other arrangements, the control system 1000 can automatically cause the fluid handling system to continue driving fluid through the catheter pump system, or to increase the pressure and/or flow rate of fluid through the system, in order to remove bubbles from the system prior to the treatment procedure.

As illustrated in the figures, the steps that require user input to carry out operations shown in FIG. 11 may be complex and also prone to errors. The errors can be caused by human operators or unforeseen system or environment conditions. Further, any error in the operation of the fluid handling system may negatively affect treatment outcomes. Accordingly, the control system 1000 can provide an automated support for operating the fluid handling system. While in the above embodiments, the control system 1000 is described with respect to the priming operation, the control system 1000 can also be programmed to provide support and control other functions of the fluid handling system described in FIG. 11, such as delivering the catheter to the patient, running the heart pump, and removing the catheter from the patient.

The control system 1000 can monitor multiple system parameters. For example, the control system can monitor motor speed, device motor current, peristaltic pump speeds, pressure sensor outputs, temperature output, bubble detector status, battery voltage, battery charge level, and battery temperature. Based on these parameters, the control system 1000 can verify system conditions and operation. Further, the control system 1000 can also use these parameters to control components, such as motors, of the fluid handling system.

In some embodiments, the control system 1000 continuously monitors the fluid handling system including console 301 by reading inputs or calculating parameters at a rate of greater than 1 Hz. In some embodiments, sampling frequency is greater than or equal to 10 Hz. The rate can also be less than 1 Hz. The control system 1000 can perform these measurements during any time or operation of the fluid handling system. These operations can be performed using parallel processing and/or software or hardware interrupts.

In some embodiments, the control system 1000 monitors several inputs simultaneously to ensure successful operation of the fluid handling system and for providing support during unexpected problems. The control system 1000 can generate alarms or send signals when the fluid handling system 100 deviates from its normal course of operation. The following examples illustrate how the control system 1000 generates alerts and/or control operations of the fluid handling system during deviation from operating range.

Figure 28:
FIG. 28 illustrates a user interface including an alert history during operation of fluid handling system, according to one embodiment.

FIG. 28 illustrates an embodiment of a user interface including an alert history during operation of fluid handling system. In an embodiment, the alert history user interface shown in FIG. 28 is generated by the control system 1000 for display after specific processes, such as priming, delivering, and the like are completed.

Figure 29:
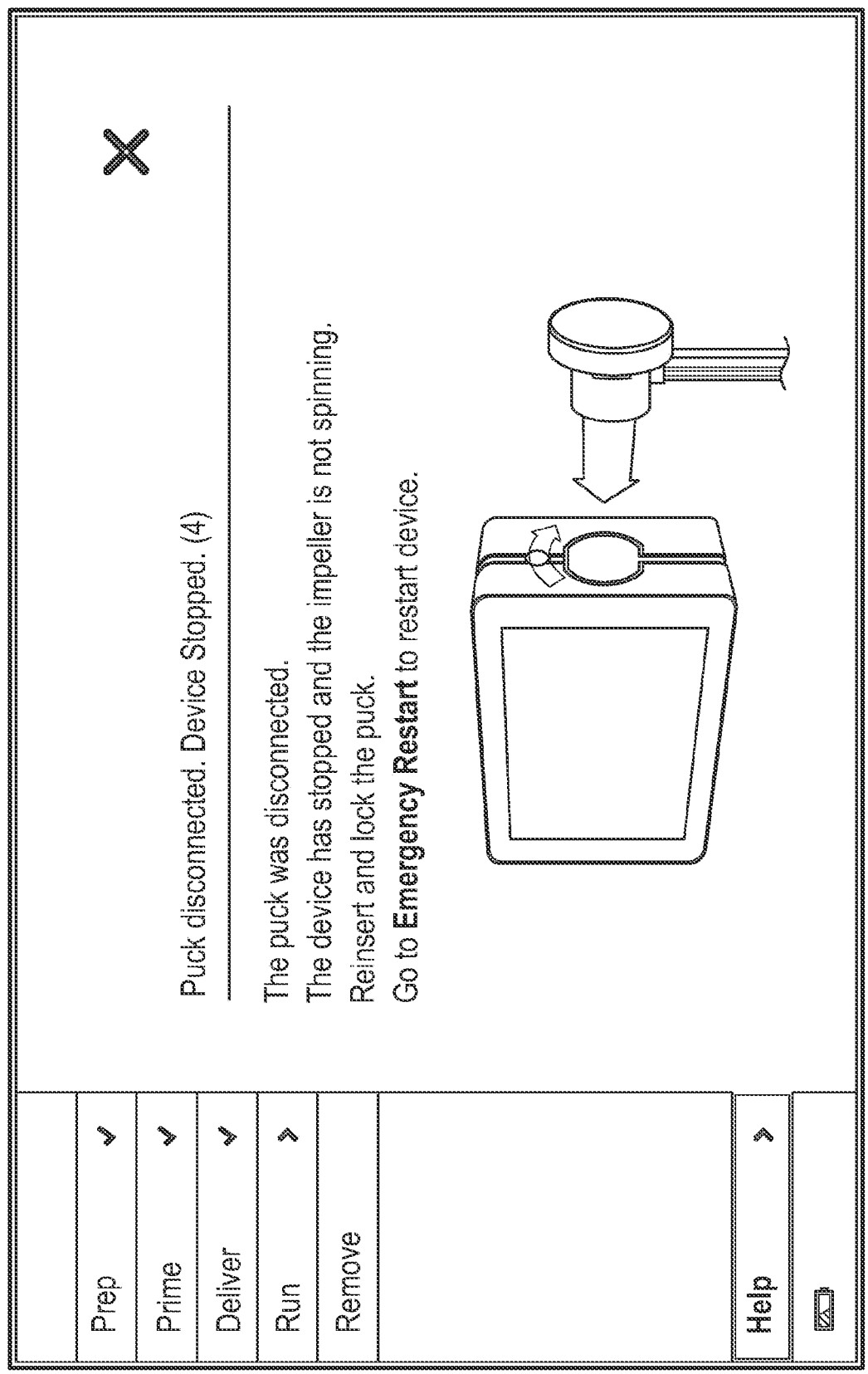
FIG. 29 illustrates a user interface for alerting the user when the puck is disconnected, according to one embodiment.

FIG. 29 illustrates an embodiment of a user interface for alerting the user when the puck is disconnected. The control system 1000 can detect if the puck gets disconnected based on received or loss of electrical signal as discussed above. The control system 1000 can generate a user interface notifying the user of the condition and to enable the user to restart the system. The control system 1000 can guide the users to emergency restart or prepare to connect a secondary console. In response to detection of puck disconnection, the control system 1000 can automatically cut off or clamp saline supply lines. The control system 1000 can also stop or maintain current to the motors depending on the process, such as, priming or delivering.

Figure 30:
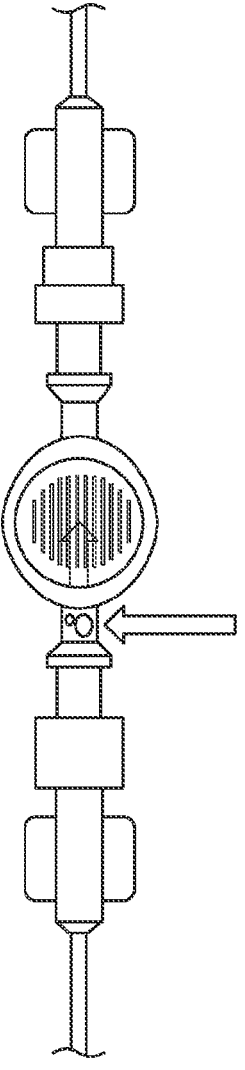
FIG. 30 illustrates a user interface generated by the control system indicating that there is air in the saline supply line, according to one embodiment.

FIG. 30 illustrates a user interface generated by the control system 1000 indicating that there is air in the saline supply line. The control system 1000 can detect for bubbles using a bubble detector based on for example, optical or sound wave sensors. Based on the detection of bubble, the control system 1000 can generate the user interface shown in FIG. 30. The control system 1000 can halt the operation of the fluid handling system until the bubble is removed. In an embodiment, the control system 1000 can automatically detect removal of bubble. The control system 1000 can also require user input for removal of bubble as shown in the illustrated figure.

Figure 31:
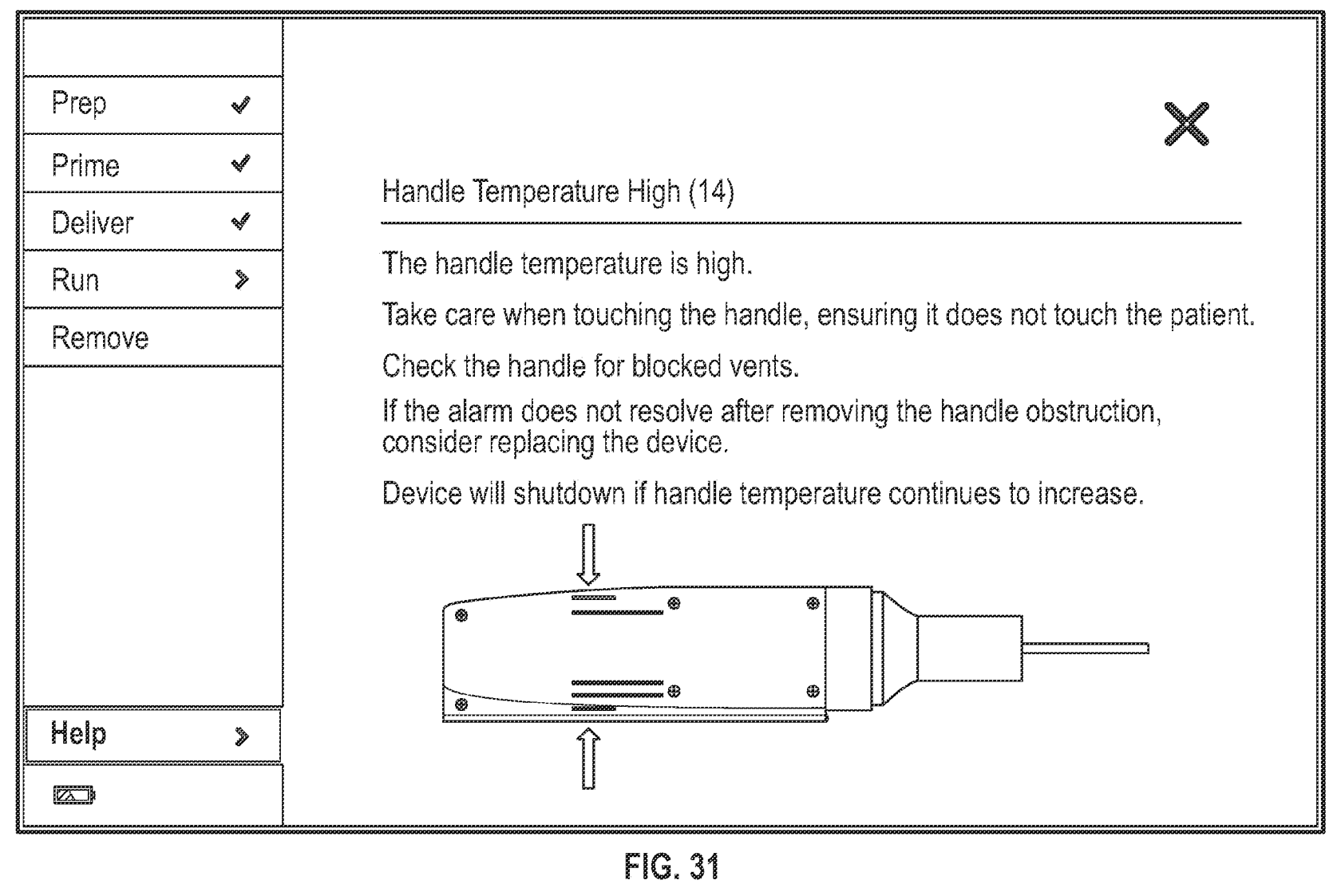

FIG. 31 illustrates a user interface generated by the control system 1000 based on a detection of temperature of the handle, in which the motor 906 may be disposed. Operation of the motor 906 within the handle can generate significant heat, which may cause the patient discomfort. The control system 1000 can monitor the temperature of the handle using one or more temperature sensors. In an embodiment, temperature sensor includes a thermocouple. The control system 1000 can compare the temperature with a predetermined threshold and generate the illustrated user interface when the temperature exceeds the threshold. The predetermined threshold can be in a range of 30° C. to 60° C., in a range of 35° C. to 50° C., or in a range of 38° C. to 45° C. The control system 1000 can provide instructions to the user based on the detected temperature. In an embodiment, the control system 1000 automatically shuts down some or all portions of fluid handling system (e.g., the motor 906) if the temperature continues to increase for a period of time or a higher threshold value.

Figure 32:
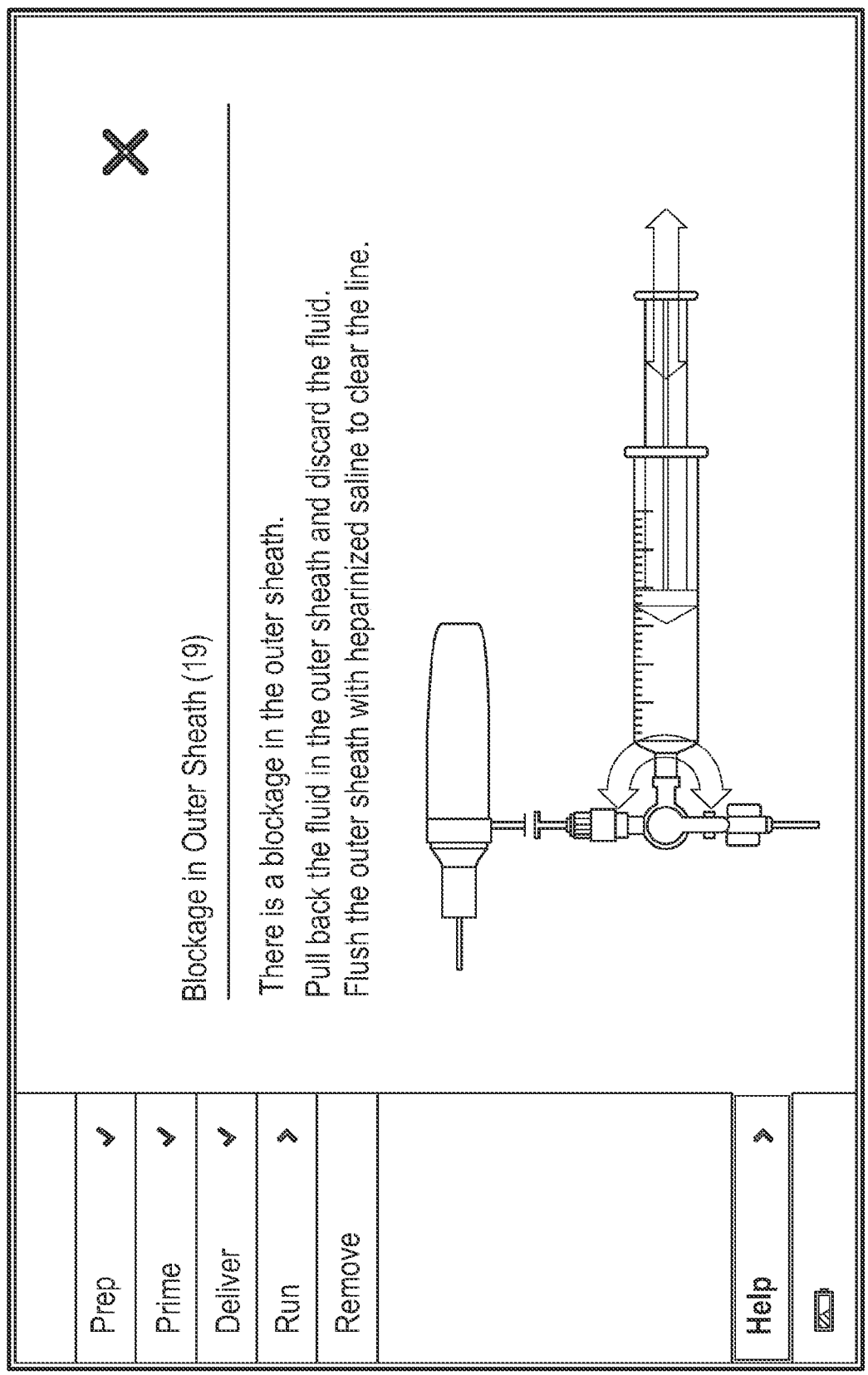
FIG. 32 illustrates a user interface generated by the control system in response to monitoring outer sheath pressure, according to one embodiment.

FIG. 32 illustrates an embodiment of a user interface generated by the control system 1000 in response to monitoring outer sheath pressure. In some embodiments, the control system 1000 can determine if there is a blockage in the outer sheath based on monitoring outer sheath pressure sensor. If the pressure is less than 50 mm Hg during operation, the control system 1000 can determine there is a blockage and generate an alert as shown in the illustrated figure. In some embodiments, if the pressure is less than 60 mm Hg, less than 45 mm HG, or less than 40 mmHg, the control system 1000 can determine there is a blockage and generate an alert. The control system 1000 can provide instructions and enable the user to flush the outer sheath with heparinized saline to clear the line. In other embodiments, in response to the alert, the system 1000 can automatically drive fluid down the outer sheath to remove the blockage.

Figure 33:
FIG. 33 illustrates a user interface generated by the control system in response to monitoring saline flow, according to one embodiment.

FIG. 33 illustrates an embodiment of a user interface generated by the control system 1000 in response to monitoring saline flow that passes distally to the impeller and cannula. The control system 1000 can monitor saline flow using direct flow measurements or indirect measurements using pressure sensors as discussed above. Based on the sensor measurements, the control system 1000 can determine that there is little or no saline flow to the catheter. Accordingly, the control system 1000 can generate the illustrated user interface to provide a user with instructions on resolving the error.

Figure 34:
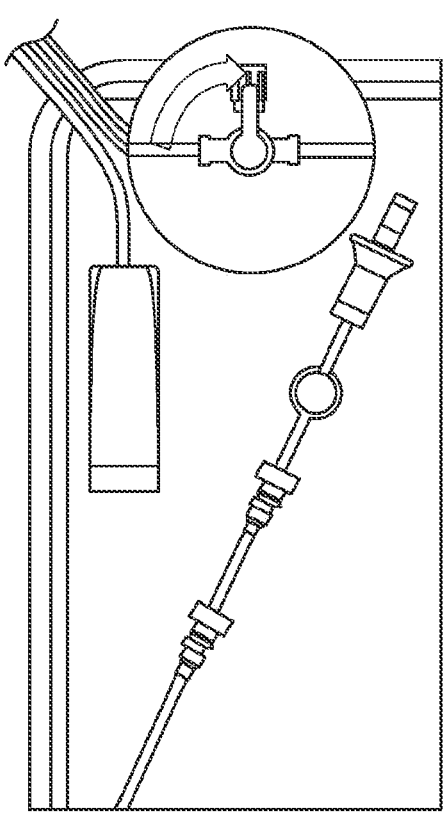
FIG. 34 illustrates a user interface generated by the control system in response to detecting outer sheath pressure, according to one embodiment.

FIG. 34 illustrates an embodiment of a user interface generated by the control system 1000 in response to detecting outer sheath pressure. As discussed above, the control system 1000 can monitor the outer sheath pressure from the pressure sensor. If the pressure is below a threshold, the control system 1000 can generate the illustrated user interface to provide instructions to the user on resolving the error.

Figure 35:
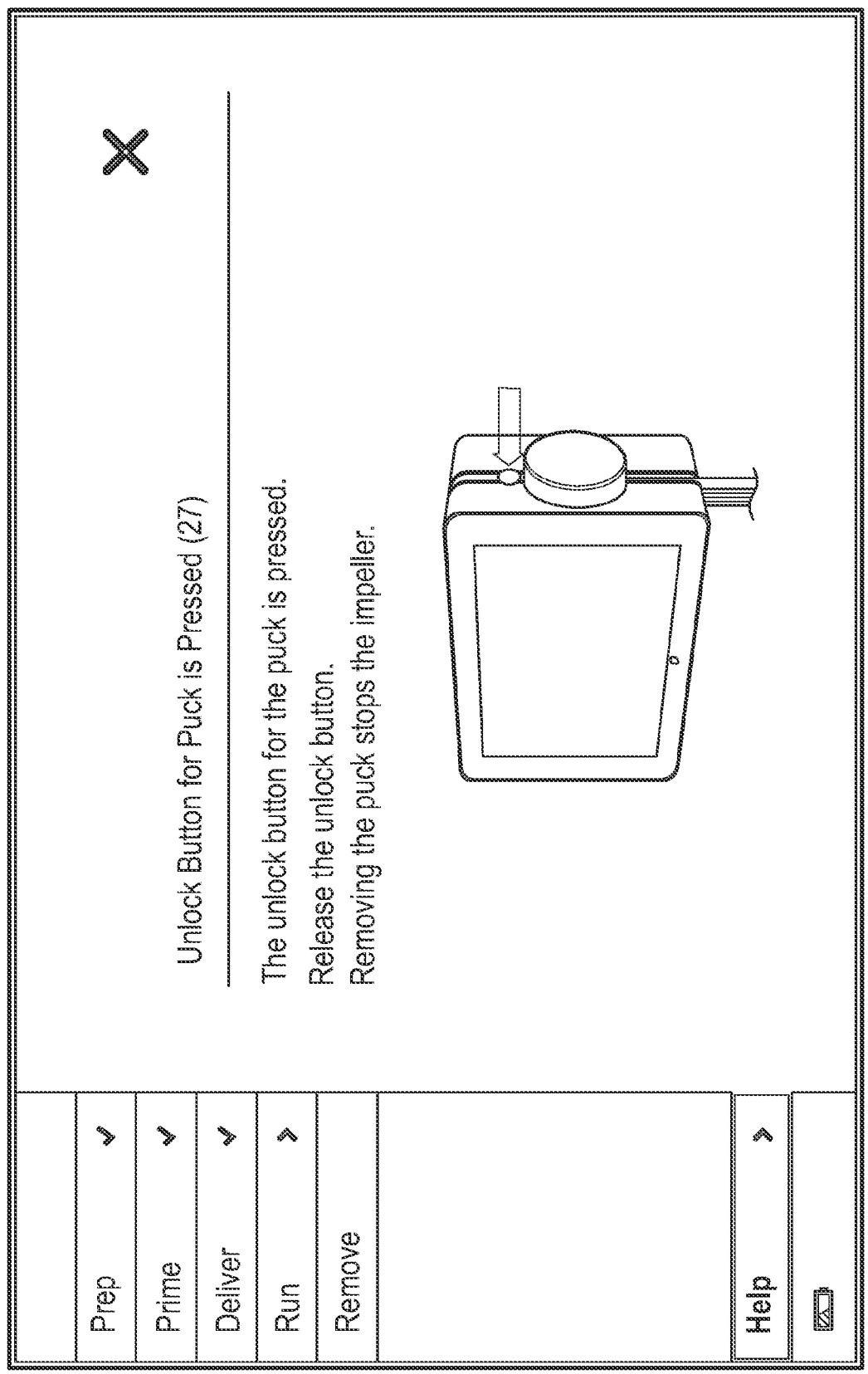
FIG. 35 illustrates a user interface generated by the control system in response to monitoring the unlock button, according to one embodiment.

FIG. 35 illustrates an embodiment of a user interface generated by the control system 1000 in response to monitoring the unlock button. The control system 1000 can monitor the unlock button using electrical connection and if the button is pressed during an operation, the control system 1000 can alert the user of the consequences.

Figure 36:
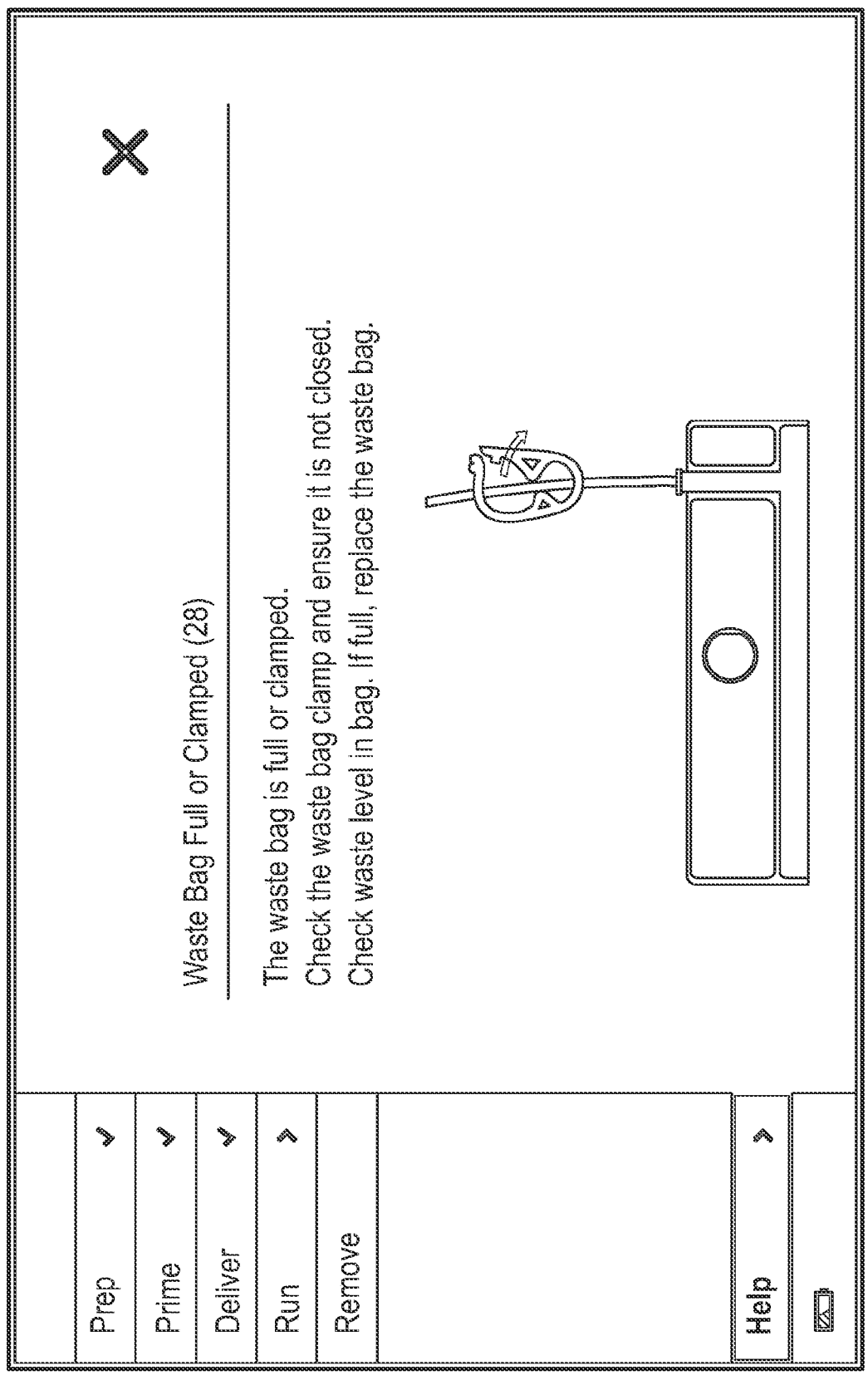
FIG. 36 illustrates a user interface generated by the control system based on monitoring of waste line pressure sensor, according to one embodiment.

FIG. 36 illustrates an embodiment of a user interface generated by the control system 1000 based on monitoring of waste line pressure sensor. For example, the control system 1000 can determine if the waste bag is full or clamped based on the readings of the waste pressure sensor. The control system 1000 can compare the waste pressure sensor with one or more thresholds or a range. Based on the comparison, the control system 1000 can determine that the waste bag is full or clamped. In some embodiments, the range is between 100 and 200 mm Hg. In other embodiments, the range is between 200 and 760 mmHg. Further, if the waste line pressure sensor goes below −30 mmHg or greater than 700 mmHg, the control system 1000 can determine that there might be a waste system failure. Accordingly, the control system 1000 can detect condition of the waste bag and generate the illustrated user interface, which can act as an alert or alarm to the user.

Figure 37:
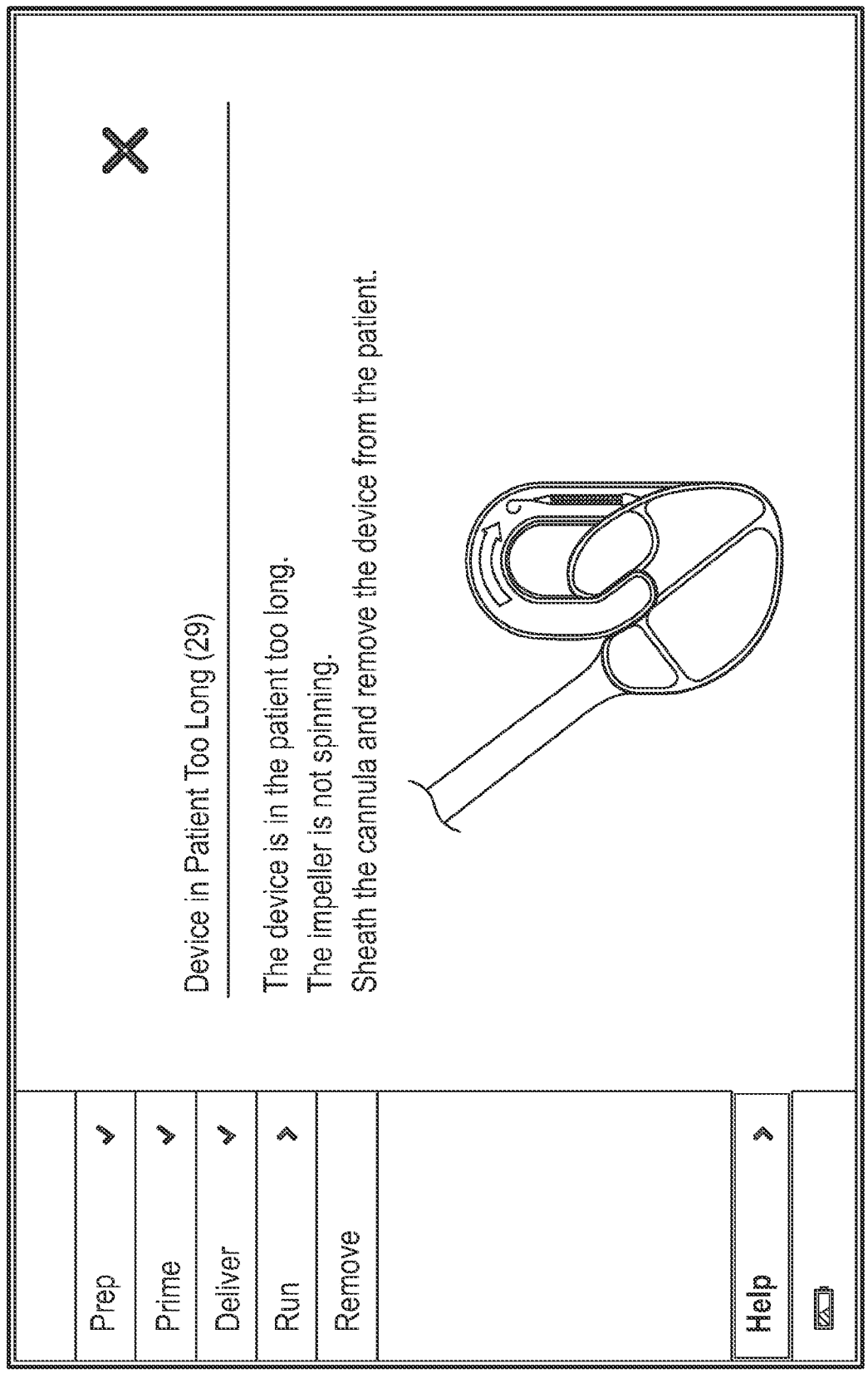
FIG. 37 illustrates a user interface generated by the control system based on monitoring device in the patient, according to one embodiment.

FIG. 37 illustrates an embodiment of a user interface generated by the control system 1000 based on monitoring device in the patient. In some embodiments, the control system 1000 can continue to monitor the arterial pressure sensor following deactivation of the motor. If the sensor indicates that the device has not been removed after a certain time has elapsed, the control system 1000 can generate the illustrated user interface. The control system 1000 can also generate an alert or the illustrated user interface based on the elapsed time after the impeller had stopped. In some embodiments, if the impeller has been running too long, the system 1000 can automatically shut off the impeller and notify the user that the impeller has been stopped. Beneficially, automatically monitoring the time of the treatment procedure can reduce the risk of hemolysis or other negative patient outcomes.

Figure 38:
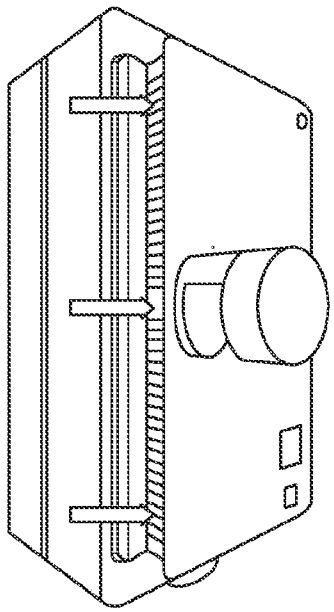
FIGS. 38, 39, and 40 illustrate user interfaces generated by the control system in response to monitoring temperature, according to one embodiment.
Figure 39:
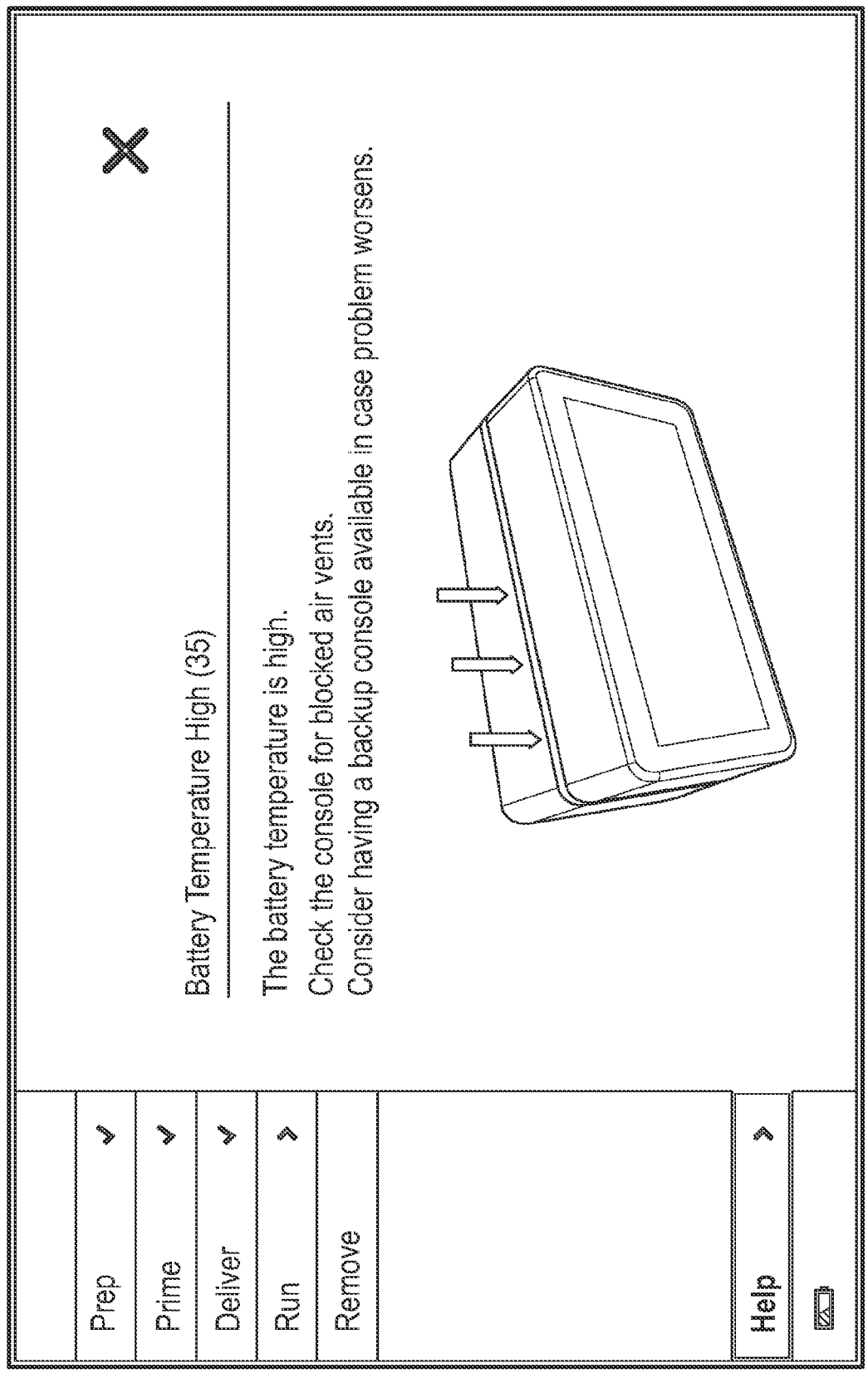
Figure 40:
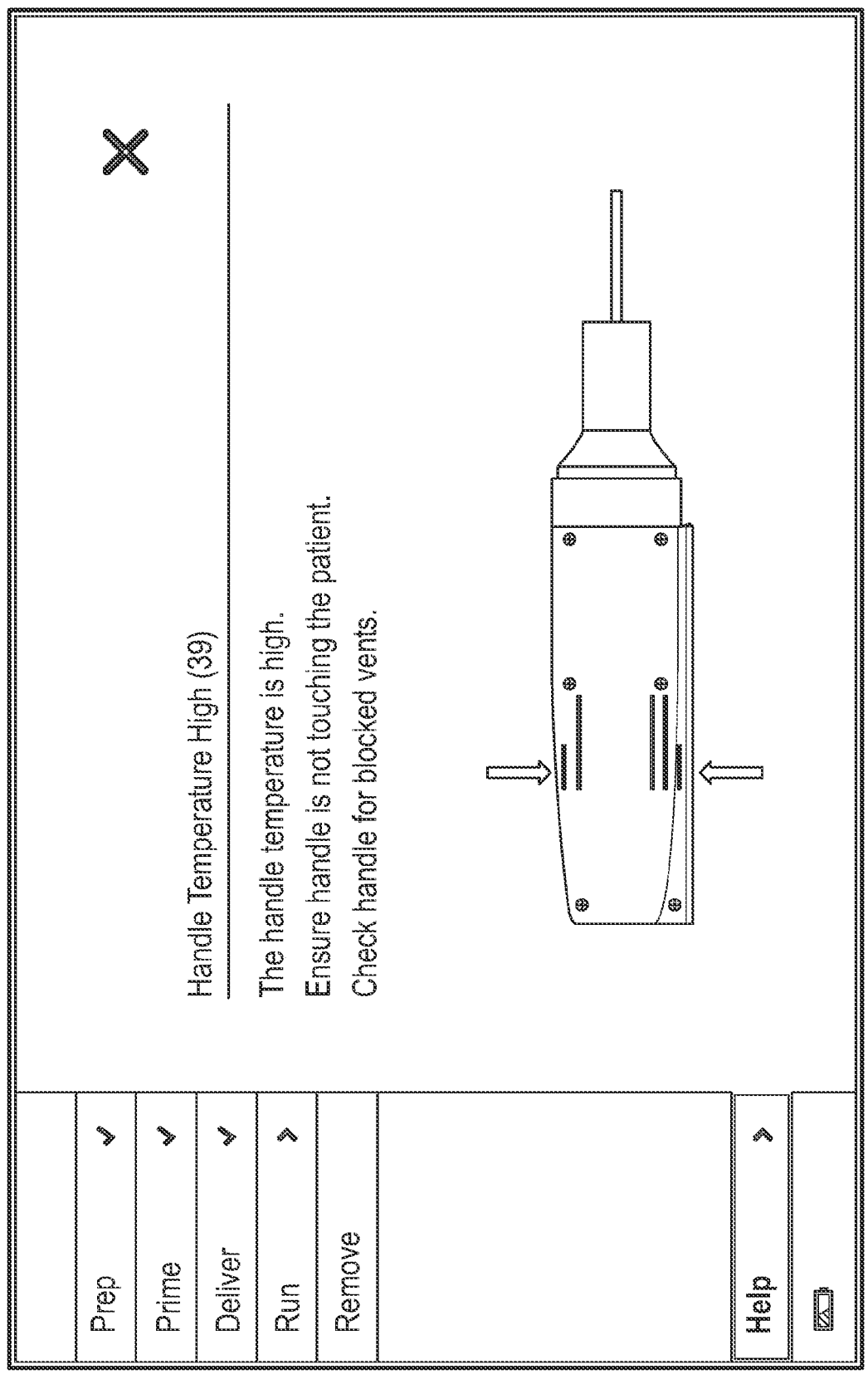

FIGS. 38, 39, and 40 illustrate embodiment of user interfaces generated by the control system 1000 in response to monitoring temperature. The handle temperature was discussed above with respect to FIG. 31. FIG. 40 shows another embodiment of the user interface corresponding to handle temperature. The control system 1000 can also monitor motor temperature, the control board temperature, and the battery board temperature. It may be advantageous to monitor temperature to ensure that it does not exceed safe ranges. The control system 1000 can monitor temperature using temperature sensors such as thermocouple or the like.

Figure 41:
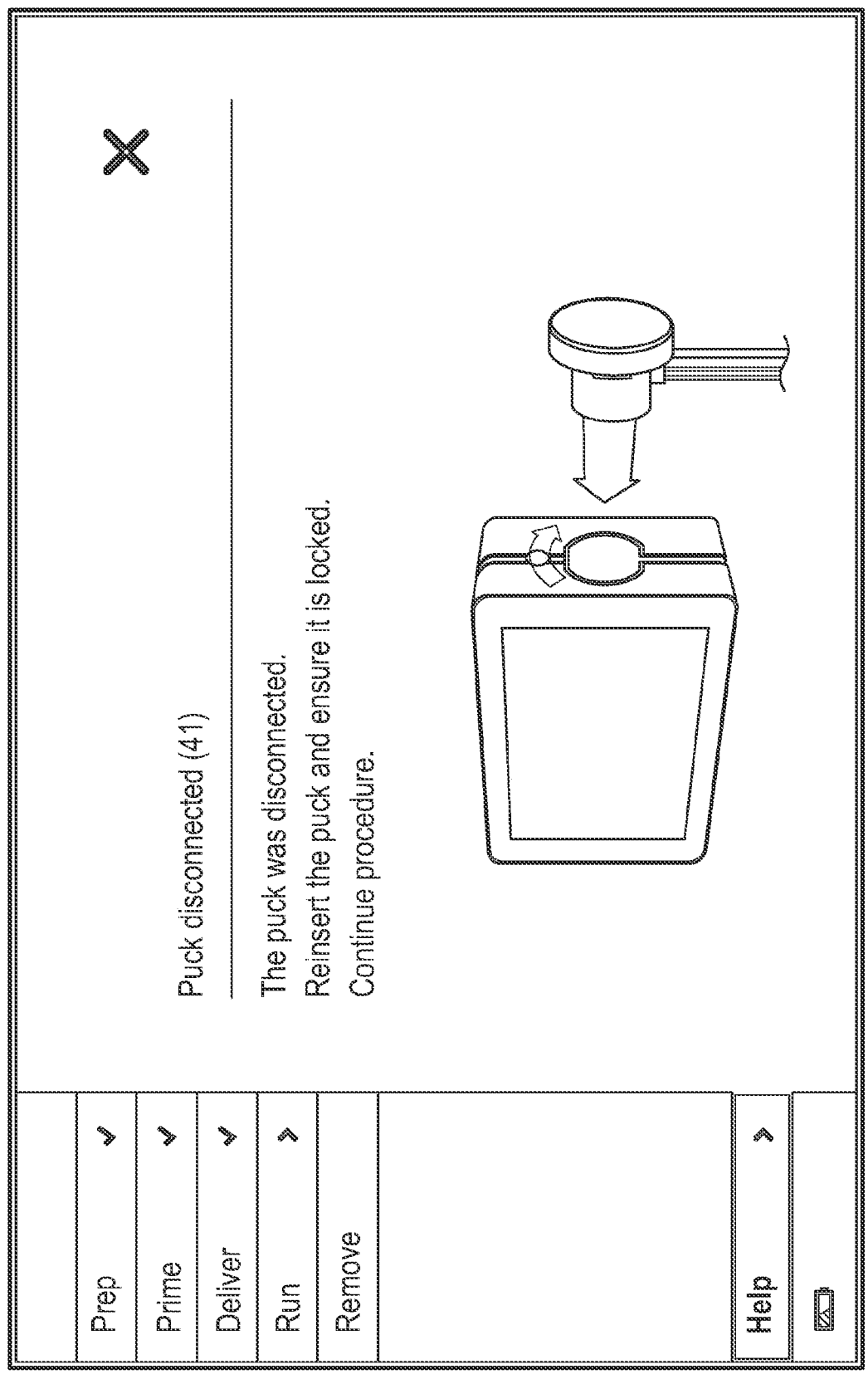
FIG. 41 illustrates a user interface generated by the control system in response to monitoring connection status of the puck, according to one embodiment.
Figure 42:
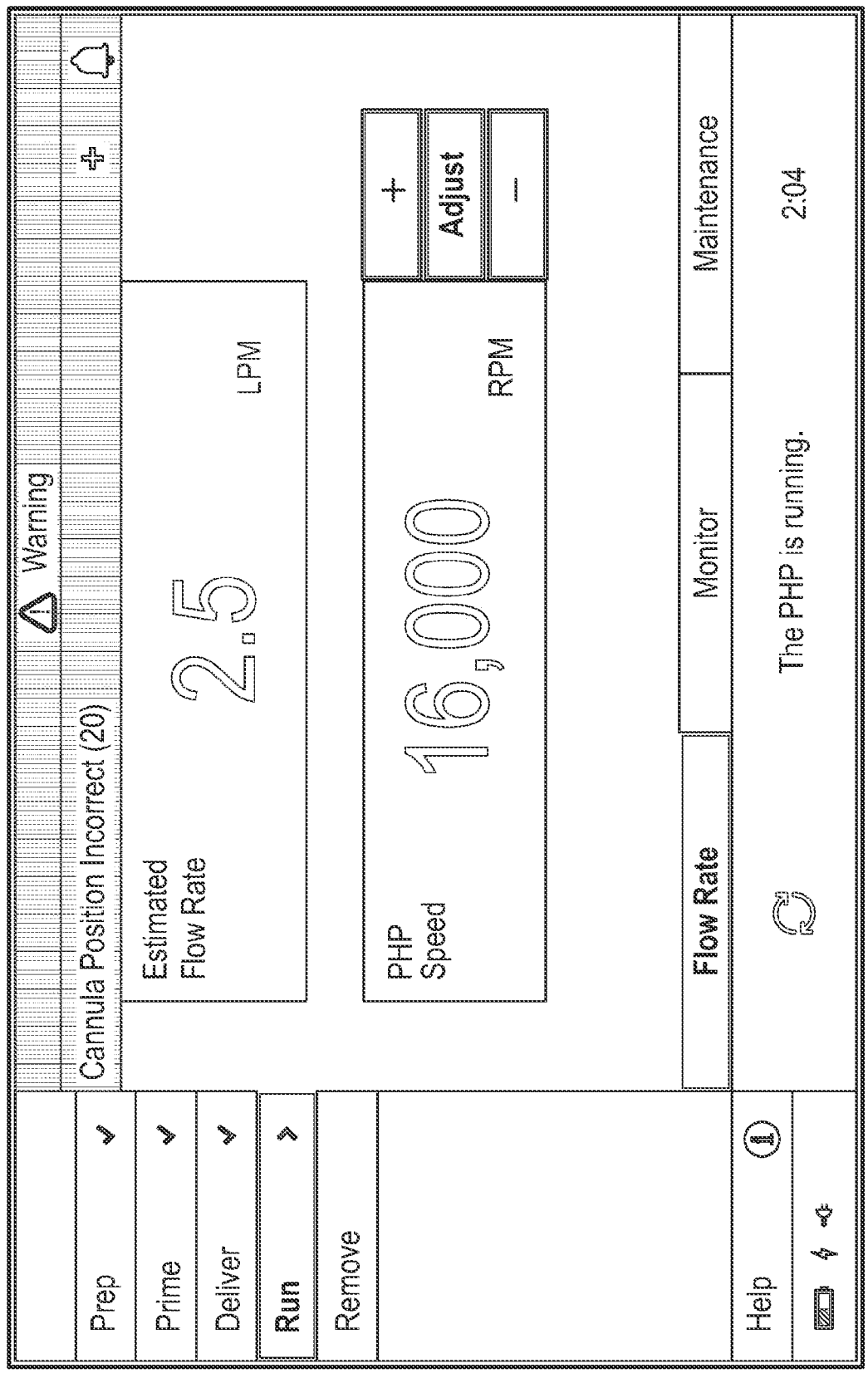
FIGS. 42 to 45 illustrate user interfaces generated by the control system in response to monitoring cannula position, according to one embodiment.
Figure 43:
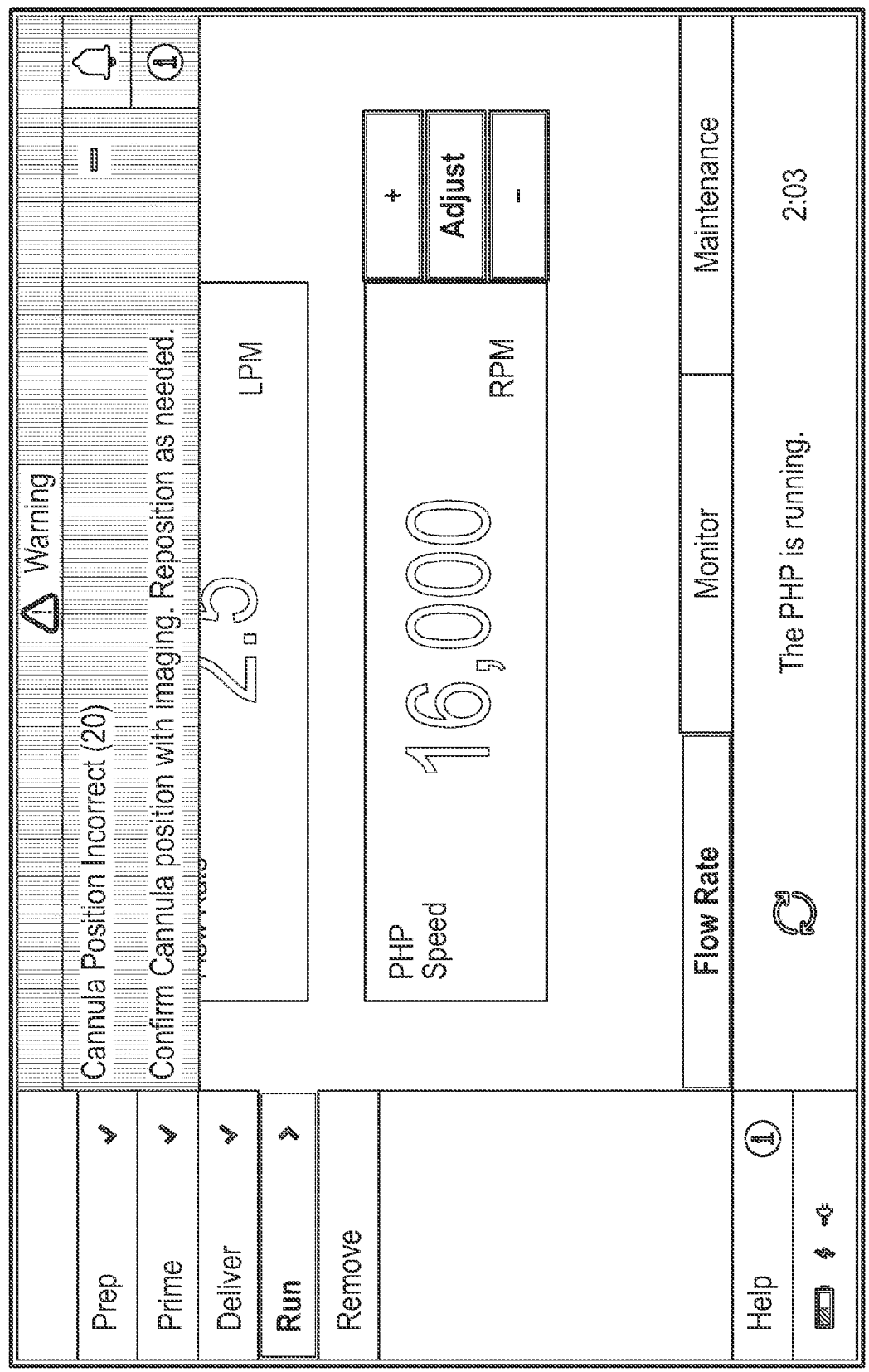
Figure 44:
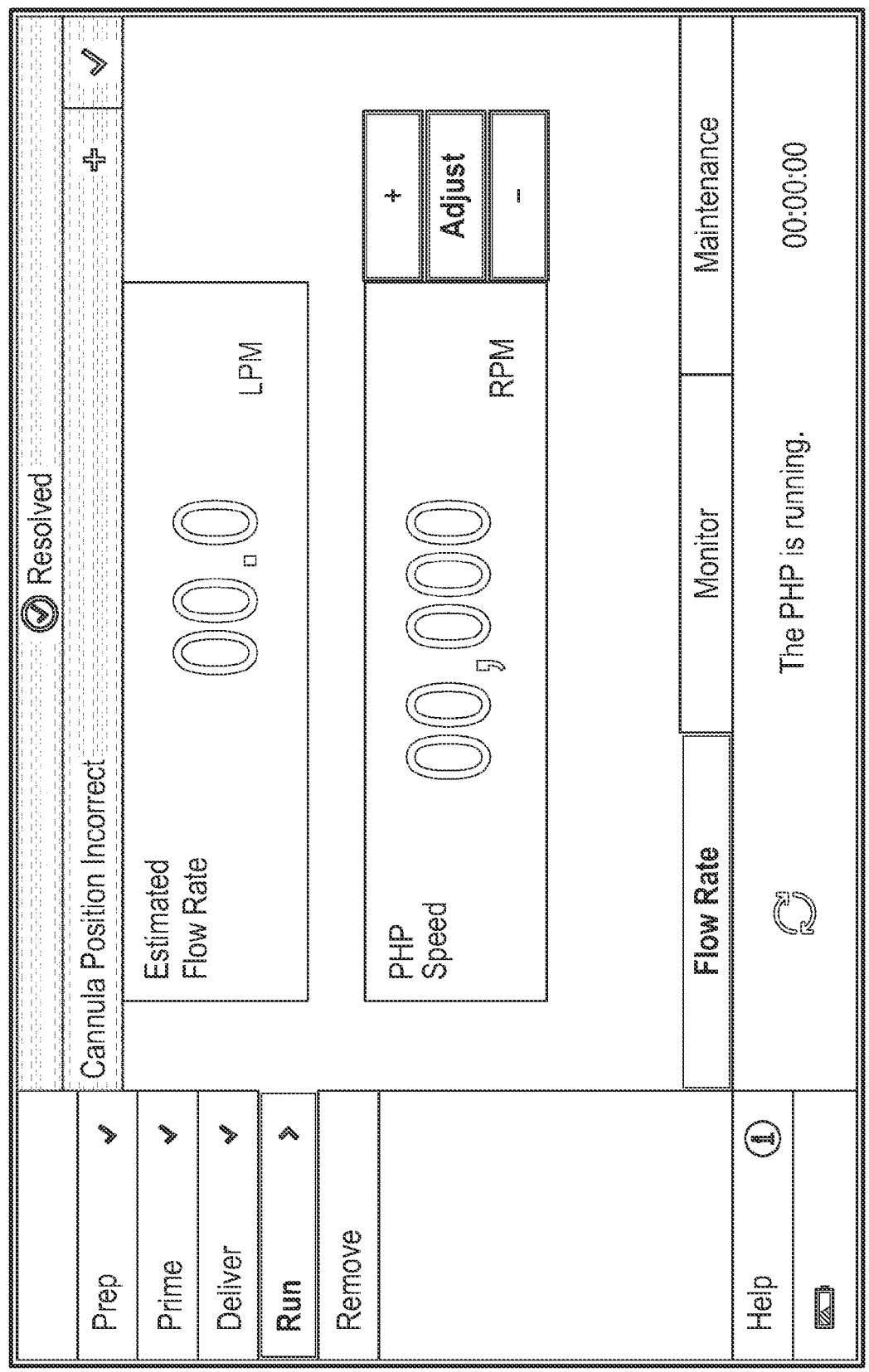
Figure 45:
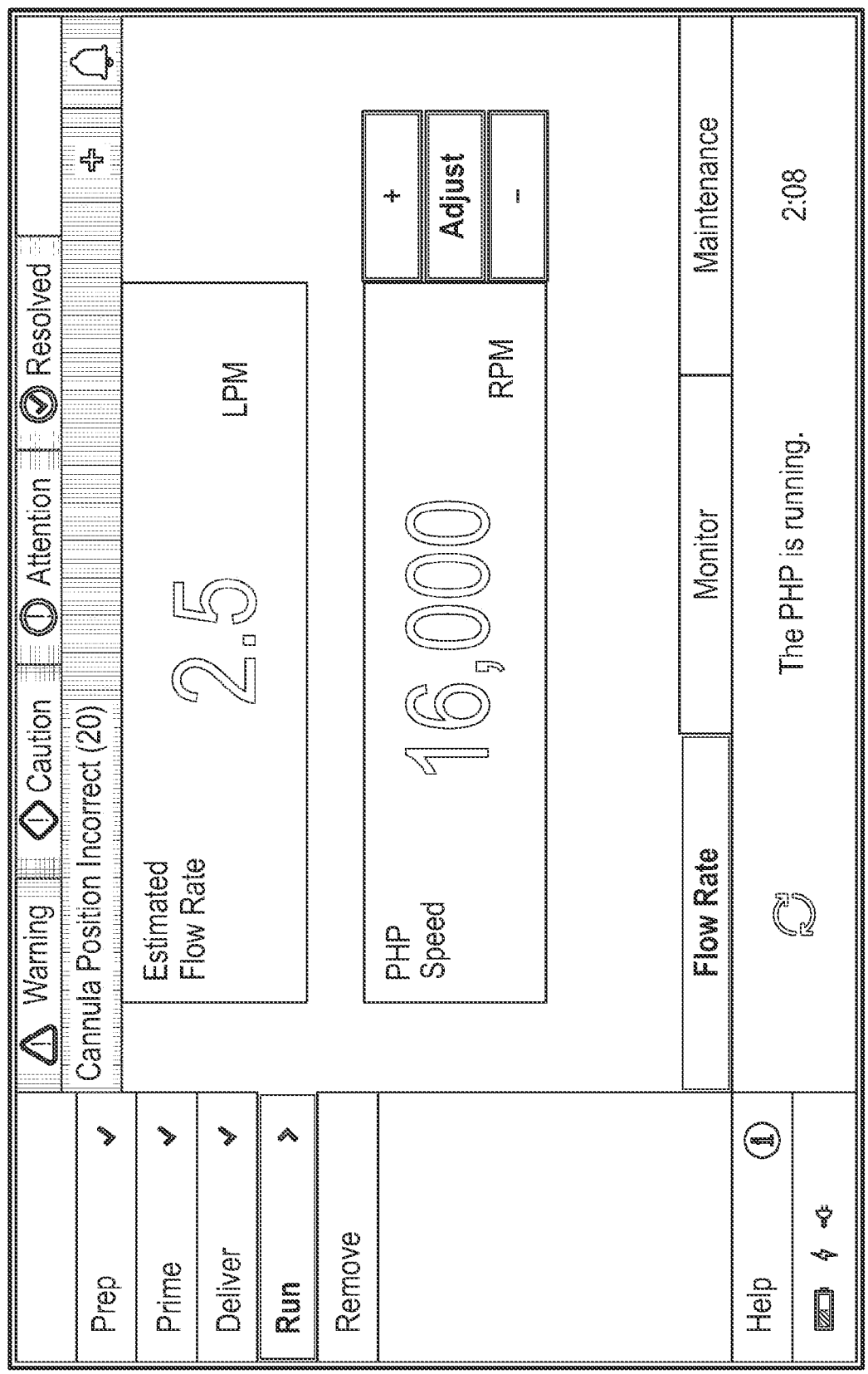

FIG. 41 illustrates an embodiment of a user interface generated by the control system 1000 in response to monitoring connection status of the puck as discussed above.

FIGS. 42 to 45 illustrate an embodiment of user interfaces generated by the control system 1000 in response to monitoring cannula position. It can be important to position the cannula accurately in order to provide adequate pumping support to the heart. For example, in left ventricular assist procedures, it can be important to place the cannula across the aortic valve such that the cannula inlet is disposed in the left ventricle and the cannula outlet is disposed in the aorta. The cannula position inside the patient may not be directly visible to the caregiver without an imager. Accordingly, the control system 1000 can indirectly through measurements determine if the position of the cannula is incorrect. For example, the control system 1000 can measure motor current. The high motor current may be a result of incorrect positioning or alignment of the cannula and impeller. It may also be a result of excessive bending of the catheter. The control system can accordingly alert the user when motor current is above a specific threshold to check positioning and alignment. Flow rate and/or pressure may also be affected by incorrect cannula position. For example, if the cannula is disposed completely within the left ventricle or completely within the aorta, then the flow profiles will be different from the flow profiles generated when the cannula is disposed across the aortic valve. Thus, the control system may also monitor flow rate based on flow rate and/or pressure measurements. Further, the frequency and/or amplitude modulation of motor parameters may also be used by the control system 1000 to determine cannula position. Similarly, the control system 1000 can also monitor the current drawn by a saline pump and/or waste pump and the corresponding output of the pumps. The control system 1000 can automatically stop the pumps if they exceed threshold values. The user interface can instruct the clinician to reposition the cannula. The system 1000 can continuously monitor the cannula position until the cannula is positioned correctly (e.g., across the aortic valve). The system 1000 can then indicate that the cannula is positioned correctly. In response to the indication, the system 1000 can automatically continue running, or the system 1000 can prompt the user to manually continue the procedure.

The control system 1000 can also determine if a component of the fluid handling system 100 has failed. For instance the control system 1000 can determine that a pressure sensor, such as an outer sheath pressure sensor has failed. The control system 1000 can acquire the pressure reading from the outer sheath pressure sensor and if it is less than −20 mmHg or greater than 300 mmHg, it is likely that the pressure sensor has failed.

The control system 1000 can measure flow rates based on pressure difference and/or motor speed. Further, in some embodiments, the control system 1000 can generate an alarm when the flow rate goes outside of a threshold range. A flow rate outside of the threshold range may indicate an issue with the patient condition, or with the positioning of the cannula. The control system 1000 can generate an alert to the caretaker or a secondary computer system to take a blood pressure measurement based on the flow rate. The control system 1000 can also measure motor current. The optimal range of motor currents and speed for particular processes of FIG. 11 may be stored in a lookup table. The control system 1000 can determine that the motor current is increasing, but the speed of the impeller is the same. Based on this determination, the control system 1000 can identify that the system may be operating outside of its optimal condition.

The ranges and numerical values discussed above may be a function of the fluid handling system, patient characteristics, among others. Accordingly, the numerical values can vary as will be understood by a person skilled in the art.

What is claimed is:
1. A fluid handling system comprising:
a console configured to connect with a first electrical interface that is configured to connect to a plurality of components of the fluid handling system, the console including a second electrical interface configured to connect with the first electrical interface, a display, and one or more hardware processors;
a catheter assembly;
a biocompatible fluid source;
a waste fluid line; and
a control system comprising the one or more hardware processors and a non-transitory memory storing instructions that, when executed, cause the control system to:

detect an electrical signal from a first component of the plurality of components of the fluid handling system responsive to a caretaker performing a first instruction;

determine a system state of the fluid handling system based at least in part on the electrical signal from the first component;

compare the system state with a predetermined state condition corresponding to said first instruction; and output an indication on the display of the system state.

2. The fluid handling system according to claim 1, wherein the instructions further cause the control system to generate on the display a first user interface including a visual indication of the first instruction.

3. The fluid handling system according to claim 2, wherein the instructions further cause the control system to generate on the display a second user interface including a visual indication of a second instruction based at least on the comparison indicating that the system state is within predetermined state condition and the first instruction is completed.

4. The fluid handling system according to claim 1, wherein the instructions further cause the control system to generate an alarm based at least on the comparison indicating that the system state is not within predetermined state condition.

5. The fluid handling system according to claim 1, further comprising a motor for driving a percutaneously insertable pump for bodily fluids, wherein the instructions further cause the control system to: determine a temperature of an impeller motor that rotates the impeller to pump blood and shut off the impeller motor responsive to the determination of the temperature of the impeller motor.

6. The fluid handling system according to claim 5, wherein the instructions further cause the control system to determine a current drawn by the motor and shut off the motor if the current drawn exceeds a predetermined threshold.

7. The fluid handling system according to claim 1, wherein the plurality of components comprises a catheter, and the instructions further cause the control system to: determine a flow state of fluid in the catheter and trigger an alarm based if the flow state is indicative of a blockage.

8. The fluid handling system according to claim 1, wherein the plurality of components comprises a priming pump and the catheter assembly, and wherein the instructions further cause the control system to cause the priming pump to use a positive pressure to prime the catheter assembly with a biocompatible fluid.

9. The fluid handling apparatus according to claim 8, wherein the instructions further cause the control system to monitor a back pressure or current draw of the priming pump and terminate the priming if the back pressure or current draw exceeds a predetermined threshold.

10. The fluid handling system according to claim 1, wherein the plurality of components comprises a priming pump and the catheter assembly, and wherein the instructions further cause the control system to cause the priming pump to use a negative pressure to prime the catheter assembly with a biocompatible fluid.

11. The fluid handling apparatus according to claim 10, wherein the instructions further cause the control system to monitor a back pressure or current draw of the priming pump and terminate the priming if the back pressure or current draw exceeds a predetermined threshold.

12. The fluid handling system according to claim 1, wherein the plurality of components comprises the catheter assembly and a primer housing for housing at least a portion of the catheter assembly during a priming operation.

13. The fluid handling system according to claim 12, wherein the primer housing comprises a tapered portion configured to compress at least a portion of the catheter assembly from an expanded configuration to a collapsed configuration, the collapsed configuration having a smaller diameter than the expanded configuration.

14. The fluid handling system according to claim 12, wherein the catheter assembly comprises an expandable impeller.

15. The fluid handling system according to claim 1, further comprising a sensor for detecting air bubbles and wherein the instructions further cause the control system to control the sensor to detect the presence of air bubbles in the catheter assembly.

16. The fluid handling system according to claim 1, wherein the instructions further cause the control system to automatically begin a priming operation upon the system state being a predetermined condition.

17. The fluid handling system according to claim 1, further comprising at least one sensor for detecting a condition of the waste fluid line.

18. The fluid handling system according to claim 1, wherein the instructions further cause the control system to generate on the display an alert history for showing a history of alert conditions of the fluid handling system.

19. A fluid handling system comprising:

a console configured to connect with a first electrical interface that is configured to connect to a plurality of components of the fluid handling system, the console including a second electrical interface configured to connect with the first electrical interface, a display, and one or more hardware processors;

a percutaneously insertable pump for bodily fluids; and a control system comprising the one or more hardware processors and a non-transitory memory storing instructions that, when executed, cause the control system to:

detect an electrical signal from a first component of the plurality of components of the fluid handling system responsive to a caretaker performing a first instruction;

determine a system state of the fluid handling system based at least in part on the electrical signal from the first component;

compare the system state with a predetermined state condition corresponding to said first instruction;

output an indication on the display of the system state;

detect a connection state between the first electrical interface and the console; and begin a priming the percutaneously insertable pump based on the detected connection state between the first electrical interface and the console and the determined system state.

20. A fluid handling system comprising:

a console configured to connect with a first electrical interface that is configured to connect to a plurality of components of the fluid handling system, the plurality of components including a catheter assembly and a primer housing for housing at least a portion of the catheter assembly during a priming operation, the console including a second electrical interface configured to connect with the first electrical interface, a display, and one or more hardware processors; and a control system comprising the one or more hardware processors and a non-transitory memory storing instructions that, when executed, cause the control system to:
detect an electrical signal from a first component of the plurality of components of the fluid handling system responsive to a caretaker performing a first instruction;
determine a system state of the fluid handling system based at least in part on the electrical signal from the first component;
compare the system state with a predetermined state condition corresponding to said first instruction; and
output an indication on the display of the system state.

* * * * *